(12) United States Patent
Ergüden et al.

(10) Patent No.: US 7,045,544 B2
(45) Date of Patent: May 16, 2006

(54) SUBSTITUTED 2,5-DIAMIDOINDOLES AS ECE INHIBITORS FOR THE TREATMENT OF CARDIOVASCULAR DISEASES

(75) Inventors: Jens-Kerim Ergüden, Wülfrath (DE); Thomas Krahn, Hagen (DE); Christian Schröder, Bergheim (DE); Johannes-Peter Stasch, Solingen (DE); Stefan Weigand, Wuppertal (DE); Hanno Wild, Wuppertal (DE); Michael Brands, Hamden, CT (US)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/490,821

(22) PCT Filed: Sep. 16, 2002

(86) PCT No.: PCT/EP02/10349

§ 371 (c)(1),
(2), (4) Date: Sep. 16, 2004

(87) PCT Pub. No.: WO03/028719

PCT Pub. Date: Apr. 10, 2003

(65) Prior Publication Data

US 2005/0038101 A1    Feb. 17, 2005

(30) Foreign Application Priority Data

Sep. 27, 2001    (DE) ................. 101 47 672

(51) Int. Cl.
*A61K 31/404* (2006.01)
*A61K 31/4439* (2006.01)
*A61K 31/433* (2006.01)
*C07D 209/40* (2006.01)
*C07D 405/12* (2006.01)

(52) U.S. Cl. ........... 514/419; 514/414; 514/339; 514/363; 514/365; 548/492; 548/465; 548/181; 548/139; 546/278.1

(58) Field of Classification Search ............ 548/492, 548/465, 181, 139; 546/278.1; 514/419, 514/414, 339, 363, 365
See application file for complete search history.

(56) References Cited

U.S. PATENT DOCUMENTS 6,337,344 B1 * 1/2002 Defossa et al. ............ 514/415

FOREIGN PATENT DOCUMENTS

| EP | 0563475 | 6/1993 |
|---|---|---|
| EP | 9933800 | 8/1999 |
| FR | 9732874 | 12/1997 |
| WO | 9414434 | 7/1994 |
| WO | WO 9933800 | * 7/1998 |
| WO | 9852925 | 11/1998 |

* cited by examiner

*Primary Examiner*—Golam M. M. Shameem
*Assistant Examiner*—Andrew Freistein

(57) ABSTRACT

The invention relates to compounds of formula (I), to a method for the production thereof, and to the use of the same as pharmaceuticals for the treatment of diseases in humans and/or animals

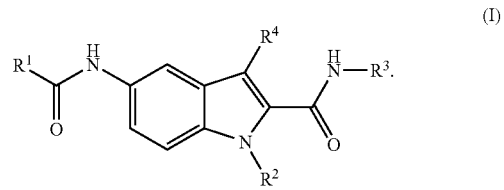

7 Claims, No Drawings

SUBSTITUTED 2,5-DIAMIDOINDOLES AS ECE INHIBITORS FOR THE TREATMENT OF CARDIOVASCULAR DISEASES

The present invention relates to 2,5-diamidoindole derivatives, to a process for their preparation and to their use as medicaments for treating disorders in humans and/or animals.

Endothelial cells and a large number of other cell types produce endothelin (ET), a polypeptide hormone having 21 amino acid residues. Endothelin is a potent vasoconstrictor formed from the prohormone "Big Endothelin" (bET, 38 amino acid residues) by cleavage of the peptide bond between Trp 21 and Val 22. The conversion of prohormone bET into the active form ET is effected by a metalloprotease, the endothelin-converting enzyme (ECE). Inhibition of ECE thus prevents the conversion of bET into biologically active ET.

ET is a potent constrictor of arterial and venous vessels. Accordingly, it has to be assumed that abnormal ET levels are directly involved in the pathophysiology of various disorders. Elevated endothelin levels are observed in cardiovascular disorders such as essential, pulmonary and malignant hypertension, in advanced atherosclerosis, myocardial infarction, heart and kidney failure (Miyauchi T, Masaki T.; Pathophysiology of endothelin in the cardiovascular system. Annu Rev Physiol. 1999; 61:391–415). Additional indications are obtained from the analysis of different animal models for ischaemic disorders such as angina pectoris, myocardial infarction and stroke and for cardiac arrhythmia and renal dysfunction. In these different syndromes, the reduction of ET levels results in a reduction of pathological parameters.

It is therefore to be assumed that the treatment of the disorders described above with ECE inhibitors leads to an improvement (Otter W., Kentsch M.; Endothelin converting enzyme inhibitors, Current Opinion in Cardiovascular, Pulmonary & Renal Investigational Drugs 2000 2(4):316–329).

It is an object of the present invention to provide medicaments for treating cardiovascular disorders, in particular the disorders described above.

The object of the present invention is achieved by compounds of the formula (I), which act as ECE inhibitors.

Compounds of a similar structure are known in other indications or for other mechanisms of action. Thus, for example, WO 99/33800 describes indole derivatives as factor Xa inhibitors, WO 94/14434 describes indole derivatives as endothelin receptor antagonists and EP-A 0 655 439 describes glycoprotein IIB/IIIA antagonists for inhibiting platelet aggregation.

The present invention provides compounds of the formula (I)

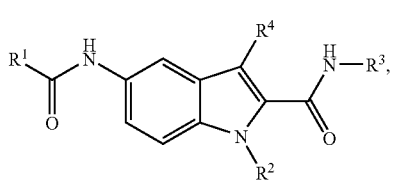

(I)

in which
R$^1$ represents (C$_5$–C$_{15}$)-alkyl, (C$_5$–C$_{15}$)-alkenyl or (CH$_2$)$_n$G,
in which G represents cycloalkyl or represents a 5- or 6-membered heterocycle having one or two oxygen atoms,
n represents 0 to 4 and
alkyl, alkenyl and G are optionally substituted by 1 to 3 substituents, independently of one another selected from the group consisting of halogen, hydroxyl, trifluoromethyl, trifluoromethoxy, cyano, nitro, alkyl, alkoxy, alkylthio, carboxyl, alkoxycarbonyl, amino, alkylamino, alkylcarbonylamino and alkylaminocarbonyl, R$^2$ represents (C$_1$–C$_8$)-alkyl, (CH$_2$)$_m$cycloalkyl, (CH$_2$)$_m$heterocyclyl, (CH$_2$)$_m$aryl or (CH$_2$)$_m$heteroaryl,
in which
m represents 0 to 4 and
alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethoxy, cyano, nitro, alkyl, alkoxy, alkylthio, alkoxycarbonyl, amino, alkylamino, alkylcarbonylamino, alkylaminocarbonyl, alkylaminosulphonyl and alkylsulphonylamino, R$^3$ represents (CH$_2$)$_o$cycloalkyl, (CH$_2$)$_o$heterocyclyl, (CH$_2$)$_o$aryl or (CH$_2$)$_o$heteroaryl,
in which
o represents 0 to 4 and
cycloalkyl, heterocyclyl, aryl and heteroaryl are optionally substituted by 1 to 3 substituents, independently of one another selected from the group consisting of halogen, hydroxyl, trifluoromethyl, trifluoromethoxy, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino, R$^4$ represents hydrogen, (C$_1$–C$_4$)-alkyl, (CH$_2$)$_p$cycloalkyl, (CH$_2$)$_p$heterocyclyl, (CH$_2$)$_p$aryl or (CH$_2$)$_p$heteroaryl,
in which
p represents 0 to 4 and
alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethoxy, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino, and their salts, hydrates, hydrates of the salts and solvates.

Depending on the substitution pattern, the compounds of the formula (I) can exist in stereoisomeric forms which either relate to each other as image and mirror image (enantiomers) or, do not relate to each other as image and mirror image (diastereomers). The invention relates both to the enantiomers or diastereomers and to their respective mixtures. The racemic forms can be separated, in a known manner, in exactly the same way as the diastereomers, into the stereoisomerically uniform constituents. Equally, the present invention also relates to the other tautomers of the compounds of the formula (I) and their salts.

Salts of the compounds of the formula (I) can be physiologically acceptable salts of the compounds according to the invention with mineral acids, carboxylic acids or sulphonic acids. Particular preference is given, for example, to salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, trifluoroacetic acid, acetic acid, propionic acid, lactic acid, tartaric acid, citric acid, fumaric acid, maleic acid or benzoic acid.

Salts which may-also be mentioned are salts with customary bases, for example alkali metal salts (e.g. sodium salts or potassium salts), alkaline earth metal salts (e.g. calcium salts or magnesium salts) or ammonium salts which are derived from ammonia or organic amines such as diethylamine, triethylamine, ethyldiisopropylamine, procaine, dibenzylamine, N-methylmorpholine, dihydroabietylamine, 1-ephenamine or methylpiperidine.

According to the invention, those forms of the compounds of the formula (I) which, in the solid or liquid state, form a molecule compound or a complex by hydration with water or coordination with solvent molecules are termed hydrates and solvates, respectively. Examples of hydrates are sesquihydrates, monohydrates, dihydrates and trihydrates. In precisely the same way, the hydrates or solvates of salts of the compounds according to the invention also come into consideration.

In addition, the invention also encompasses prodrugs of the compounds according to the invention. According to the invention, those forms of the compounds of the formula (I) which may themselves be biologically active or inactive but which can be converted (for example metabolically or solvolytically) into the corresponding biologically active form under physiological conditions are termed prodrugs.

Within the context of the present invention, the substituents have, unless otherwise indicated, the following meaning:

Alkyl represents straight-chain or branched alkyl and comprises, unless indicated otherwise, $C_1$–$C_6$-alkyl, in particular methyl, ethyl, propyl, isopropyl, butyl, isobutyl.

$C_5$–$C_{15}$)-Alkyl, ($C_1$–$C_8$)-alkyl, ($C_1$–$C_4$)-alkyl represents straight-chain or branched alkyl having 5 to 15, 1 to 8 and 1 to 4 carbon atoms, respectively. The following radicals may be mentioned by way of example and by way of preference: neopentyl, isoamyl.

Cycloalkyl comprises saturated hydrocarbon radicals having up to 14 carbon atoms, i.e. monocyclic $C_3$–$C_{12}$-cycloalkyl, preferably $C_3$–$C_8$-cycloalkyl, such as, for example, cyclopropyl, cyclobutyl, cyclopentyl, cyclohexyl, cycloheptyl, cyclooctyl, cyclononyl, and polycyclic alkyl, i.e. preferably bicyclic and tricyclic, optionally spirocyclic $C_7$–$C_{14}$-cycloalkyl, such as, for example, bicyclo[2.2.1]-hept-1-yl, bicyclo[2.2.1]-hept-2-yl, bicyclo[2.2.1]-hept-7-yl, bicyclo [2.2.2]-oct-2-yl, bicyclo-[3.2.1]-oct-2-yl, bicyclo[3.2.2]-non-2-yl and adamantyl.

Aryl represents an aromatic radical having 6 to 10 carbon atoms. Preferred aryl radicals are phenyl and naphthyl.

Alkoxy represents a straight-chain or branched alkyl radical having in particular 1 to 6, 1 to 4 or 1 to 3 carbon atoms which is attached via an oxygen atom. Preference is given to a straight-chain or branched alkoxy radical having 1 to 3 carbon atoms. The following radicals may be mentioned by way of example and by way of preference: methoxy, ethoxy, n-propoxy, isopropoxy, t-butoxy, n-pentoxy and n-hexoxy.

Alkylthio represents a straight-chain or branched alkyl radical having in particular 1 to 6, 1 to 4 or 1 to 3 carbon atoms which is attached via a sulphur atom. Preference is given to a straight-chain or branched alkylthio radical having 1 to 3 carbon atoms. The following radicals may be mentioned by way of example and by way of preference: methylthio, ethylthio, n-propylthio, isopropylthio, t-butylthio, n-pentylthio and n-hexylthio.

Alkoxycarbonyl represents a straight-chain or branched alkoxy radical having 1 to 6 or 1 to 4 carbon atoms which is attached via a carbonyl group. Preference is given to a straight-chain or branched alkoxycarbonyl radical having 1 to 4 carbon atoms. The following radicals may be mentioned by way of example and by way of preference: methoxycarbonyl, ethoxycarbonyl, n-propoxycarbonyl, isopropoxycarbonyl and t-butoxycarbonyl.

Alkylamino represents an amino group which has one straight-chain or branched or two identical or different straight-chain or branched alkyl substituents having preferably in each case 1 to 6, 1 to 4 or 1 to 2 carbon atoms. Preference is given to straight-chain or branched alkylamino radicals having in each case 1 to 4 carbon atoms. The following radicals may be mentioned by way of example and by way of preference: methylamino, ethyl amino, n-propylamino, isopropyl amino, t-butyl amino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkylcarbonylamino (acylamino) represents, in the context of the invention, an amino group having a straight-chain or branched alkyl radical which is attached via a carbonyl group and has preferably 1 to 6, 1 to 4 or 1 to 2 carbon atoms. Preference is given to a monoacylamino radical having 1 to 2 carbon atoms. The following radicals may be mentioned by way of example and by way of preference: acetamido, propionamido, n-butyramido and pivaloylamido.

Alkylaminocarbonyl represents an amino group which is attached via a carbonyl group and has one straight-chain or branched or two identical or different straight-chain or branched alkyl substituents having preferably in each case 1 to 4 or 1 to 2 carbon atoms. The following radicals may be mentioned by way of example and by way of preference: methylaminocarbonyl, ethylaminocarbonyl, isopropyl aminocarbonyl, t-butylaminocarbonyl, N,N-dimethylaminocarbonyl, N,N-diethylaminocarbonyl, N-ethyl-N-methylaminocarbonyl and N-t-butyl-N-methylaminocarbonyl.

Heteroaryl represents a 5- to 10-membered aromatic heterocycle having up to 3 heteroatoms from the group consisting of S, O and/or N. The following radicals may be mentioned by way of example and by way of preference: pyridyl, pyrimidyl, thienyl, furyl, pyrrolyl, thiazolyl, N-triazolyl, oxazolyl or imidazolyl. Preference is given to pyridyl, furyl, thiazolyl and N-triazolyl.

Heterocyclyl represents a 3- to 8-membered saturated or partially unsaturated heterocycle which may contain up to 3 heteroatoms from the group consisting of S, O and N and which may be attached via a nitrogen atom. The following radicals may be mentioned by way of example and by way of preference: morpholinyl, piperidinyl, piperazinyl, methylpiperazinyl, thiomorpholinyl, pyrrolidinyl, and also 3-, 7- and 8-membered heterocycles, such as, for example, aziridines (for example 1-azacyclopropan-1-yl), azetidines (for example 1-azacyclobutan-1-yl) and azepines (for example 1-azepan-1-yl). The unsaturated representatives may contain 1 or 2 double bonds in the ring.

Halogen represents fluorine, chlorine, bromine or iodine, with fluorine and chlorine being preferred, unless indicated otherwise.

Alkylaminosulphonyl represents an amino group which is attached via a sulphonyl group and which has one straight-chain or branched or two identical or different straight-chain or branched alkyl substituents having preferably 1 to 4 or 1 to 2 carbon atoms. The following radicals may be mentioned by way of example and by way of preference: methylaminosulphonyl, ethylaminosulphonyl, isopropylaminosulphonyl, t-butylaminosulphonyl, N,N-dimethylaminosulphonyl, N,N-diethylaminosulphonyl, N-ethyl-N-methylaminosulphonyl and N-t-butyl-N-methylaminosulphonyl.

Alkylsulphonylamino represents a sulphonyl group which is attached via an amino group and which has one straight-chain or branched alkyl substituent having preferably 1 to 4 or 1 to 2 carbon atoms. The following radicals may be mentioned by way of example and by way of preference: methylsulphonylamino, ethylsulphonylamino, isopropylsulphonylamino, t-butylsulphonylamino.

The abovementioned general or preferred radical definitions apply both to the end products of the formula (I) and, correspondingly, to the starting materials or intermediates required in each case for the preparation.

Preference is given to compounds of the formula (I) in which $R^1$ represents $(C_5–C_{15})$-alkyl or $(CH_2)_n$cycloalkyl, in which n represents 0 to 4 and alkyl and cycloalkyl are optionally substituted by 1 to 3 substituents, independently of one another selected from the group consisting of halogen, hydroxyl, trifluoromethyl, trifluoromethoxy, cyano, nitro, alkyl, alkoxy, alkylthio, carboxyl, alkoxycarbonyl, alkyl carbonylamino and alkylaminocarbonyl, $R^2$ represents $(C1–C_8)$-alkyl, $(CH_2)_m$cycloalkyl, $(CH_2)_m$heterocyclyl, $(CH_2)_m$aryl or $(CH_2)_m$heteroaryl, in which m represents 0 to 4 and alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethoxy, cyano, nitro, alkyl, alkoxy, alkylthio, alkoxycarbonyl, amino, alkylamino, alkylcarbonylamino, alkylaminocarbonyl, alkylaminosulphonyl and alkylsulphonylamino, $R^3$ represents $(CH_2)_o$cycloalkyl, $(CH_2)_o$heterocyclyl, $(CH_2)_o$aryl or $(CH_2)_o$heteroaryl, in which o represents 0 to 4 and cycloalkyl, heterocyclyl, aryl and heteroaryl are optionally substituted by 1 to 3 substituents, independently of one another selected from the group consisting of halogen, hydroxyl, trifluoromethyl, trifluoromethoxy, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino, $R^4$ represents hydrogen, $(C_1–C_4)$-alkyl, $(CH_2)_p$cycloalkyl, $(CH_2)_p$heterocyclyl, $(CH_2)_p$aryl or $(CH_2)_p$heteroaryl, in which p represents 0 to 4 and alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethoxy, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino, and their salts, hydrates, hydrates of the salts and solvates.

Particular preference is given to compounds of the formula (I) in which $R^1$ represents neopentyl, (bicyclo[2.2.1]heptyl)methyl, cyclohexylmethyl, cyclobutylmethyl, cyclopentylmethyl, 2,2-dimethyl-1-butyl, 2-ethyl-2-methyl-1-butyl, (1-methylcyclopentyl)methyl, 1-methylcyclohexyl, 4-hydroxy-2,2-dimethyl-1-butyl or 2,2-dimethyl-1-but-3-enyl, $R^2$ represents $(C_1–C_4)$-alkyl which may be substituted by hydroxyl or fluorine or represents benzyl which is optionally substituted by 1 or 2 substituents, independently of one another selected from the group consisting of fluorine, chlorine, bromine, methyl and trifluoromethyl, $R^3$ represents phenyl, pyridyl or pyrimidyl which for their part are optionally substituted by a substituent selected from the group consisting of fluorine, chlorine, trifluoromethyl, methyl, ethyl, methoxy, ethoxy, n-propoxy, isopropoxy, amino, hydroxyl, hydroxycarbonyl, $(C_1–C_3)$-alkylcarbonyl amino and mono-$(C_1–C_4)$-alkylaminocarbonyl, $R^4$ represents hydrogen and their salts, hydrates, hydrates of the salts and solvates.

Preference is given to compounds of the formula (I) in which $R^1$ represents neopentyl.

Preference is also given to compounds of the formula (I) in which $R^2$ represents benzyl which may be substituted up to two times, independently of one another, by alkyl or halogen, preferably fluorine.

Preference is also given to compounds of the formula (I) in which $R^3$ represents phenyl which may be substituted up to two times, independently of one another, by alkyl or alkoxy.

Preference is also given to compounds of the formula (I) in which $R^3$ represents phenyl, pyridyl or pyrimidyl, which for their part are optionally substituted by a substituent selected from the group consisting of fluorine, chlorine, trifluoromethyl, methyl, ethyl, methoxy, ethoxy, n-propoxy, isopropoxy, amino, hydroxyl, hydroxycarbonyl, $(C_1–C_3)$-alkylcarbonylamino and mono-$(C_1–C_4)$-alkylaminocarbonyl.

Preference is also given to compounds of the formula (I) in which $R^4$ represents hydrogen.

Preference is also given to compounds of the formula (I) in which $R^1$ represents $(C_5–C_{10})$-alkyl or $(CH_2)_n(C_4–C_7)$-cycloalkyl, preferably $(CH_2)_n$cyclobutyl, $(CH_2)_n$cyclopentyl, $(CH_2)_n$cyclohexyl or $(CH_2)_n$bicyclo-[2.2.1]-heptyl, in which n represents 1 to 3 and alkyl and cycloalkyl are optionally substituted by 1 to 3 substituents, independently of one another selected from the group consisting of halogen, hydroxyl, trifluoromethyl, trifluoromethoxy, cyano, nitro, alkyl, alkoxy, alkylthio, carboxyl, alkoxycarbonyl, alkylcarbonylamino and alkylaminocarbonyl, $R^2$ represents $(C_1–C_4)$-alkyl, $(CH_2)_m$cycloalkyl or $(CH_2)_m$aryl, in which m represents 0 to 4 and alkyl, cycloalkyl and aryl are optionally substituted by 1 to 3 substituents, independently of one another selected from the group consisting of halogen, trifluoromethyl, cyano, nitro, alkyl, alkoxy, amino, alkylamino, alkylcarbonylamino and alkylaminocarbonyl, $R^3$ represents $(CH_2)_o$aryl or $(CH_2)_o$heteroaryl,
in which
o represents 0 to 3 and
aryl and heteroaryl are optionally substituted by 1 to 3 substituents, independently of one another selected from the group consisting of halogen, trifluoromethyl, cyano, nitro, alkyl, alkoxy, amino, alkylamino, alkylcarbonylamino and alkylaminocarbonyl,
$R^4$ represents hydrogen, $(C_1-C_4)$-alkyl or $(CH_2)_p$aryl,
in which
p represents 1 to 4 and
alkyl and aryl are optionally substituted by 1 to 3 substituents, independently of one another selected from the group consisting of halogen, trifluoromethyl, cyano, nitro, alkyl, alkoxy, alkylcarbonylamino and alkylaminocarbonyl, and their salts, hydrates, hydrates of the salts and solvates.

Particular preference is given to compounds of the formula (I)
in which
$R^1$ represents neopentyl, bicyclo[2.2.1]heptyl, cyclohexylmethyl, cyclobutylmethyl, cyclopentylmethyl, 2,2-dimethyl-4-butyl, 2,2-dimethyl-1-butyl or 2-ethyl-2-methyl-1-butyl, which for their part are optionally substituted by 1 to 2 substituents, independently of one another selected from the group consisting of halogen, cyano, alkyl, alkoxy, alkylcarbonylamino and alkylaminocarbonyl,
$R^2$ represents $(C_1-C_4)$-alkyl or $(CH_2)_m$phenyl,
in which
m represents 0 to 4 and
alkyl and phenyl are optionally substituted by 1 to 2 substituents, independently of one another selected from the group consisting of halogen, trifluoromethyl, cyano, alkyl, alkoxy, alkylcarbonylamino and alkylaminocarbonyl,
$R^3$ represents $(CH_2)_o$phenyl, $(CH_2)_o$pyridyl, $(CH_2)_o$thienyl or $(CH_2)_o$pyrimidyl,
in which
o represents 0 to 3 and
phenyl, pyridyl, thienyl and pyrimidyl for their part are optionally substituted by 1 to 3 substituents, independently of one another selected from the group consisting of halogen, trifluoromethyl, cyano, nitro, alkyl, alkoxy, alkylcarbonylamino and alkylaminocarbonyl,
$R^4$ represents hydrogen or $(C_1-C_4)$-alkyl,
in which alkyl is optionally substituted by 1 to 3 substituents, independently of one another selected from the group consisting of halogen and trifluoromethyl, and their salts, hydrates, hydrates of the salts and solvates.

Particular preference is also given to combinations of two or more of the preferred ranges mentioned above.

The present invention also provides a process for preparing the compounds of the formula (I), characterized in that either

[A] compounds of the formula (II)

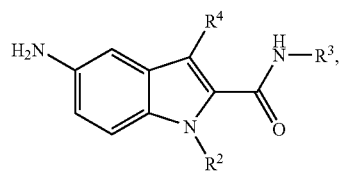

in which
$R^2$, $R^3$ and $R^4$ are as defined above, are reacted with compounds of the formula (III)

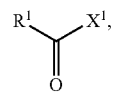

in which
$R^1$ is as defined above and
$X^1$ represents halogen, preferably bromine or chlorine, or hydroxyl, or

[B] compounds of the formula (XI)

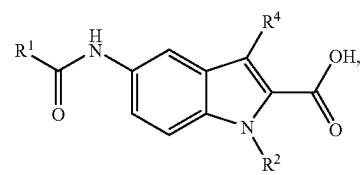

in which
$R^1$, $R^2$ and $R^4$ are as defined above, are reacted with compounds of the formula (VI)

in which
$R^3$ is as defined above, to give compounds of the formula (I).

If $X^1$ represents halogen, the reaction in process A is carried out in inert solvents, if appropriate in the presence of a base, preferably in the temperature range of from 0° C. to 50° C. at atmospheric pressure.

Suitable inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as nitromethane, ethyl acetate, acetone, dimethylformamide, dimethylacetamide, 1,2-dimethoxyethane, 2-butanone, dimethyl sulphoxide, acetonitrile, pyridine or hexamethylphosphoric triamide; preference is given to dioxane or methylene chloride.

Suitable bases are, for example, alkali metal hydroxides, such as sodium hydroxide or potassium hydroxide, or alkali metal carbonates, such as caesium carbonate, sodium carbonate or potassium carbonate, or amides, such as, lithium diisopropylamide, or other bases, such as DBU, triethylamine or diisopropylethylamine; preference is given to diisopropylethylamine or triethylamine.

In process step A (if $X^1$ represents hydroxyl) and in process B, the reaction of compound (II) with compound (III) and of compound (XI) with compound (VI), respectively, to give compounds of the formula (I) are carried out in inert solvents, in the presence of customary condensing agents, if appropriate in the presence of a base, preferably in a temperature range of from room temperature to 50° C. at atmospheric pressure.

Suitable inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as nitromethane, ethyl acetate, acetone, dimethylformamide, dimethylacetamide, 1,2-dimethoxyethane, dimethyl sulphoxide, acetonitrile or pyridine; preference is given to tetrahydrofuran, dimethylformamide, 1,2-dichloroethane or methylene chloride.

Customary condensing agents are, for example, carbodiimides, such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl polystyrene (PS-carbodiimide) or carbonyl compounds, such as carbonyldiimidazole, or 1,2-oxazolium compounds, such as 2-ethyl-5-phenyl-1,2-oxazolium 3-sulphate or 2-tert-butyl-5-methylisoxazolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures of these.

Suitable bases are, for example, alkali metal carbonates, such as, for example, sodium carbonate or potassium carbonate or sodium bicarbonate or potassium bicarbonate, or organic bases, such as trialkylamines, for example triethylamine, N-methylmorpholine, N-methylpiperidine, 4-dimethylaminopyridine or diisopropylethylamine.

Preference is given to the combination of N-(3-dimethylaminoisopropyl)-N'-ethylcarbodiimide hydrochloride (EDC), 1-hydroxybenzotriazole (HOBt) and triethylamine; O-(7-azabenzotriazol-1-yl)-N,N,N',N'-tetramethyluronium hexafluorophosphate (HATU) and triethylamine or N-(3-dimethylaminoisopropyl)-N'-ethylcarbodiimide hydrochloride (EDC) and 4-dimethylaminopyridine in dimethylformamide or carbonyldiimidazole in 1,2-dichloroethane.

To prepare compounds of the formula (II) for [A], compounds of the formula (IV) (IV), (IV)

[structure: O$_2$N-indole with R$^4$ at 3-position, C(=O)NH-R$^3$ at 2-position, R$^2$ on N]

in which

R$^2$, R$^3$ and R$^4$ are as defined above, are reacted with reducing agents in inert solvents.

Compounds of the formula (IV) can be prepared by two different routes.

[A 1] Firstly, compounds of the formula (V)

(V)

[structure: O$_2$N-indole with R$^4$ at 3-position, COOH at 2-position, R$^2$ on N]

in which

R$^2$ and R$^4$ are as defined above, are reacted either with compounds of the formula (VI)

$$R^3\text{—}NH_2 \quad (VI)$$

in which

R$^3$ is as defined above, under the reaction conditions described for the reaction of compounds of the formula (II) with compounds of the formula (III) to give compounds of the formula (I) (if X$^1$ represents hydroxyl), or compounds of the formula (V) are initially reacted with thionyl chloride and then with compounds of the formula (VI), in inert solvents, if appropriate in the presence of a base.

To prepare the compounds of the formula (V), compounds of the formula (VII)

(VII)

[structure: O$_2$N-indole with R$^4$ at 3-position, C(=O)OR$^5$ at 2-position, NH]

in which

R$^4$ is as defined above an

R$^5$ represents alkyl, preferably methyl or ethyl, are reacted, in a one-step or two-step process, with compounds of the formula (VIII)

$$R^2\text{—}X^2 \quad (VIII)$$

in which

R$^2$ is as defined above and

X$^2$ represents halogen, preferably bromine or chlorine, in the presence of a base, in inert solvents. In the two-step process, in the first step, the indole nitrogen atom is alkylated and, in a second step, after a change of base, the ester is hydrolysed to the acid.

[A 2] It is also possible to prepare compounds of the formula (IV) by reacting compounds of the formula (IX)

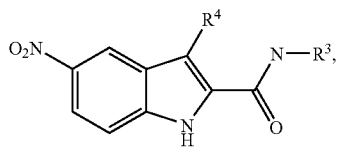
(IX)

in which
R³ and R⁴ are as defined above, with compounds of the formula (VIII)

R²—X²     (VIII)

in which
R² and X² are as defined above, in the presence of a base, in inert solvents.

To prepare compounds of the formula (IX), compounds of the formula (X)

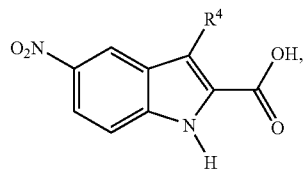
(X)

in which
R⁴ is as defined above, are reacted either with compounds of the formula (VI)

R³—NH₂     (VI)

in which
R³ is as defined above, under the reaction conditions described for the reaction of compounds of the formula (II) with compounds of the formula (III) to give compounds of the formula (I) (if X¹ represents hydroxyl), or compounds of the formula (X) are initially reacted with thionyl chloride and then with compounds of the formula (VI) in inert solvents, if appropriate in the presence of a base.

To prepare the compounds of the formula (X), the ester function of compounds of the formula (VII)

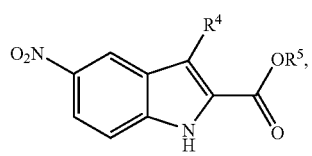
(VII)

in which
R⁴ and R⁵ are as defined above, is hydrolysed.

To prepare the compounds of the formula (XI) for [B], the ester function of compounds of the formula (XI)

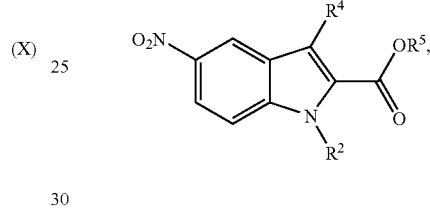
(XII)

in which
R¹, R², R⁴ and R⁵ are as defined above, is hydrolysed.

Compounds of the formula (XII) can be prepared by two different routes.

[B 1] Firstly, the nitro group in compounds of the formula (XIII)

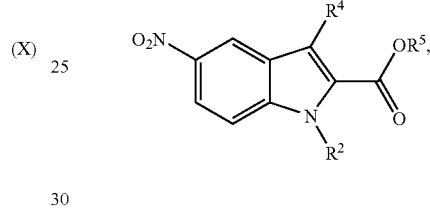
(XIII)

in which
R², R⁴ and R⁵ are as defined above is reduced and the product is then reacted with compounds of the formula (XIII)

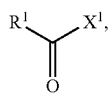
(III)

in which
R¹ and X¹ are as defined above.

To prepare compounds of the formula (XIII), compounds of the formula (VII)

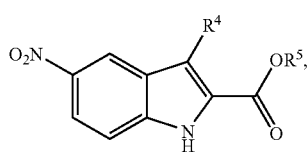
(VII)

in which
R⁴ and R⁵ are as defined above are reacted with compounds of the formula (VIII)

R²—X²     (VIII)

in which
R² and X² are as defined above in the presence of a base in inert solvents.

[B 2] It is also possible to prepare compounds of the formula (XII) by reacting compounds of the formula (XIV)

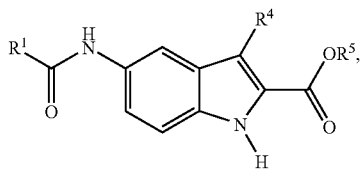

in which

R$^1$, R$^4$ and R$^5$ are as defined above with compounds of the formula (VIII)

                                                        (VIII)

in which

R$^2$ and X$^2$ are as defined above, in the presence of a base in inert solvents.

To prepare compounds of the formula (XIV), the nitro group in compounds of the formula (VII)

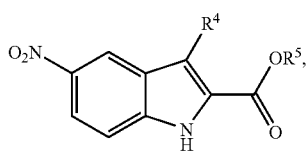

in which

R$^4$ and R$^5$ are as defined above is reduced, and the product is then reacted with compounds of the formula (III)

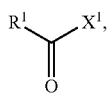

in which

R$^1$ and X$^1$ are as defined above.

Suitable inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, dioxane, tetrahydrofuran, glycol dimethyl ether or diethylene glycol dimethyl ether, alcohols, such as methanol, ethanol, propanol, isopropanol or butanol, hydrocarbons, such as benzene, xylene, toluene, hexane, cyclohexane or mineral oil fractions, or other solvents, such as nitromethane, ethyl acetate, acetone, dimethylformamide, dimethylacetamide, 1,2-dimethoxyethane, dimethyl sulphoxide, acetonitrile or pyridine.

Suitable bases are the customary inorganic or organic bases. These preferably include alkali metal and alkaline earth metal hydroxides, such as, for example, lithium hydroxide, sodium hydroxide or potassium hydroxide, or alkali metal and alkaline earth metal carbonates, such as caesium carbonate, sodium carbonate or potassium carbonate, or sodium methoxide or potassium methoxide or sodium ethoxide or potassium ethoxide or potassium tert-butoxide, or amides, such as sodium amide, lithium bis(trimethylsilyl)amide or lithium diisopropylamide, or organometallic compounds, such as butyllithium or phenyllithium, or amines, such as triethylamine, diisopropylethylamine, diisopropylamine, N-methylmorpholine, 4-dimethylaminopyridine or pyridine, or other bases such as sodium hydride or DBU. If appropriate, in addition to the bases, additives such as crown ethers (for example 18-crown-6), or inorganic salts, such as, for example, sodium iodide or copper(I) bromide are employed.

Suitable reducing agents are, for example, tin dichloride, titanium trichloride or palladium on activated carbon and hydrogen, where palladium on activated carbon is, if appropriate, employed with added ammonium acetate and/or acetic acid.

The reaction step (IV)→(II) and the first step (reduction) in reaction steps (XIII)+(III)→(XII) and (VII)+(III)→(XIV) is preferably carried out using tin dichloride in ethanol, methanol or dimethylformamide or using palladium on carbon in the presence of ammonium formate in ethyl acetate/ethanol, preferably in a temperature range of from room temperature to the reflux temperature of the solvents, at from atmospheric pressure to 3 bar.

The first step of reaction steps (V)+(VI)→(IV) and (X)+(VI)→(IX) is preferably carried out using an excess of thionyl chloride as solvent, preferably in a temperature range of from 50° C. to the reflux temperature of the reactants at atmospheric pressure. In the second step, the reaction is preferably carried out in methylene chloride using the base triethylamine, preferably in a temperature range of from 0° C. to 40° C. at atmospheric pressure.

In the one-step process, the reaction step (VII)+(VIII)→(V) is preferably carried out in dimethyl sulphoxide using the base potassium hydroxide or sodium hydroxide, preferably in a temperature range of from 0° C. to 40° C. at atmospheric pressure.

The alkylation in the first step of the two-step process and in reaction steps (XI)+(VIII)→(IV); (VII)+(VIII)→(XIII); (XIV)+(VIII)→(XII) is preferably carried out in dimethyl sulphoxide using the base sodium hydride or in THF using the base potassium tert-butoxide and with addition of crown ether, preferably in a temperature range of from room temperature to 50° C. at atmospheric pressure. If R$^2$ in the compounds (VIII) represents an aromatic radical, the reaction (VII)+(VIII)→(XIII) is carried out in the presence of the base potassium carbonate, with added copper(I) bromide.

The hydrolysis in the second step of reaction step (VII)+(VIII)→(V) is preferably carried out in dimethyl sulphoxide using the base potassium hydroxide or sodium hydroxide, preferably in a temperature range of from 0° C. to 40° C. at atmospheric pressure.

The reaction steps (VII)→(X) and (XII)→(XI) are preferably carried out in methanol and THF using, as base, aqueous lithium hydroxide solution, preferably in a temperature range of from RT to 90° C. at atmospheric pressure.

The second step (acylation) in reaction steps (XIII)+(III)→(XII) and (VII)+(III)→(XIV) is preferably carried out in the solvent dichloromethane or THF in the presence of the base triethylamine in a temperature range of from 0° C. to 40° C. at atmospheric pressure.

The compounds of the formulae (III), (VI) and (VIII) are known per se to the person skilled in the art or can be prepared by customary processes known from the literature.

The compounds of the formula (VII) are known per se to the person skilled in the art or can be prepared by customary processes known from the literature (cf.: A. Guy, J.-P. Guetté, *Synthesis* 1980, 222–223).

The processes described above can be illustrated in an exemplary manner by the formula schemes below:
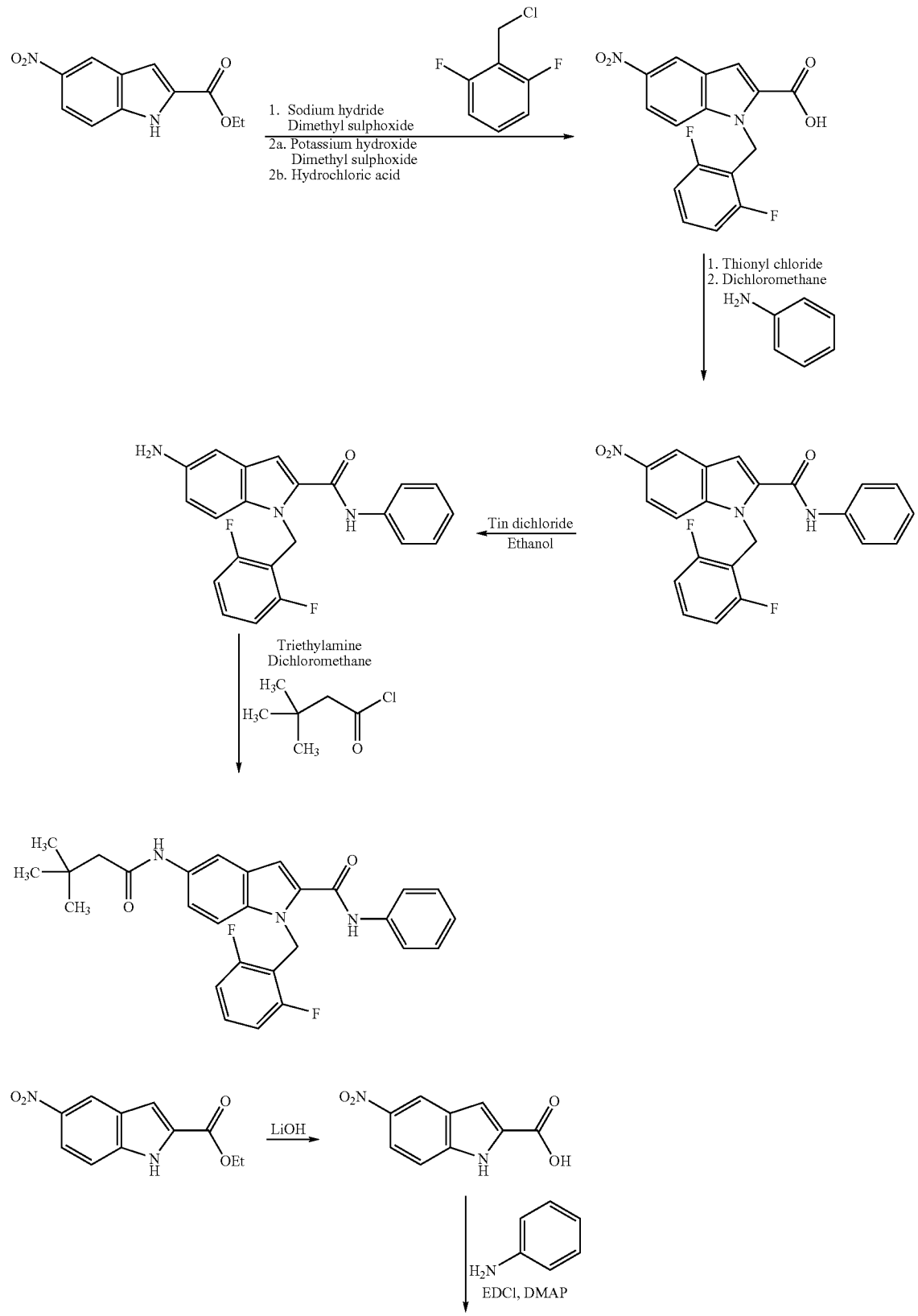

-continued
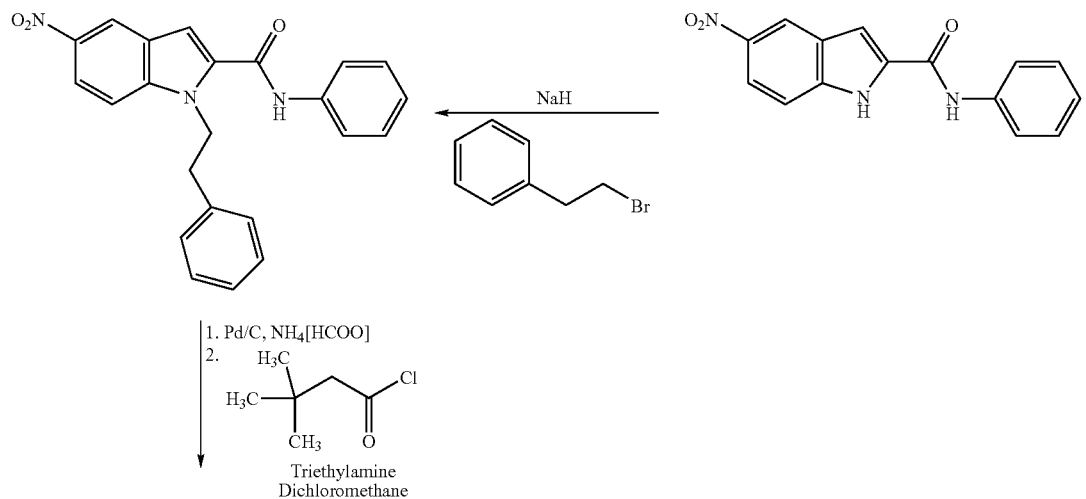
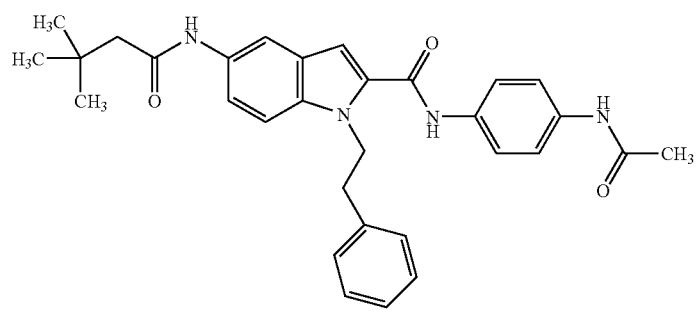
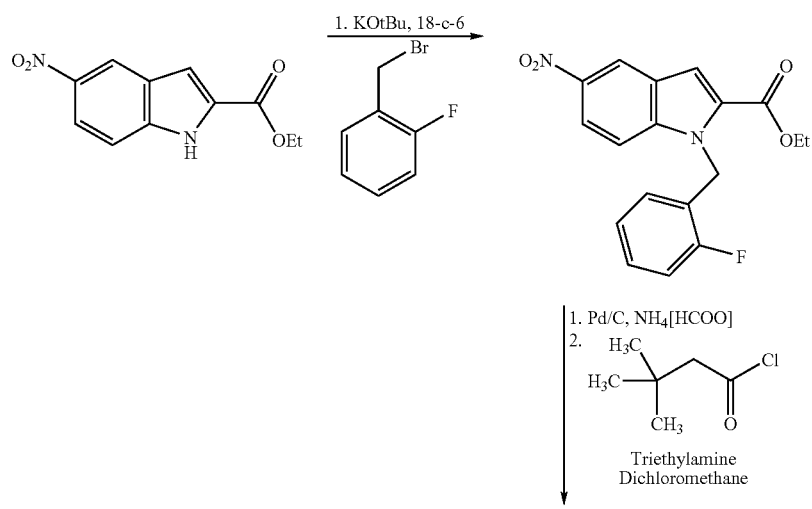

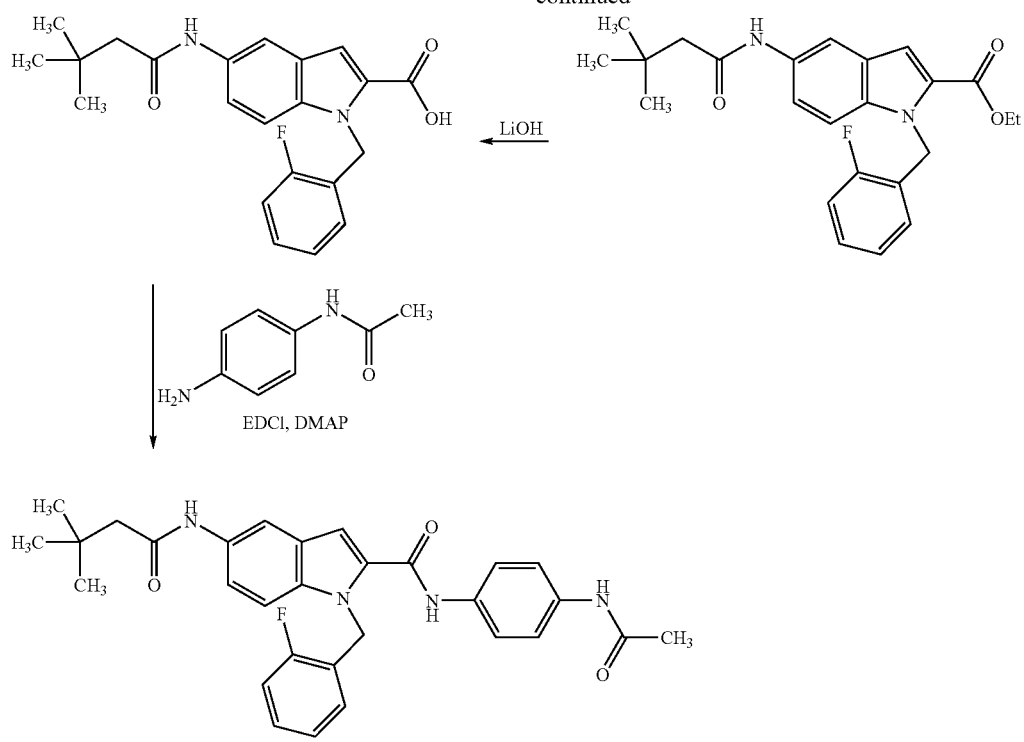
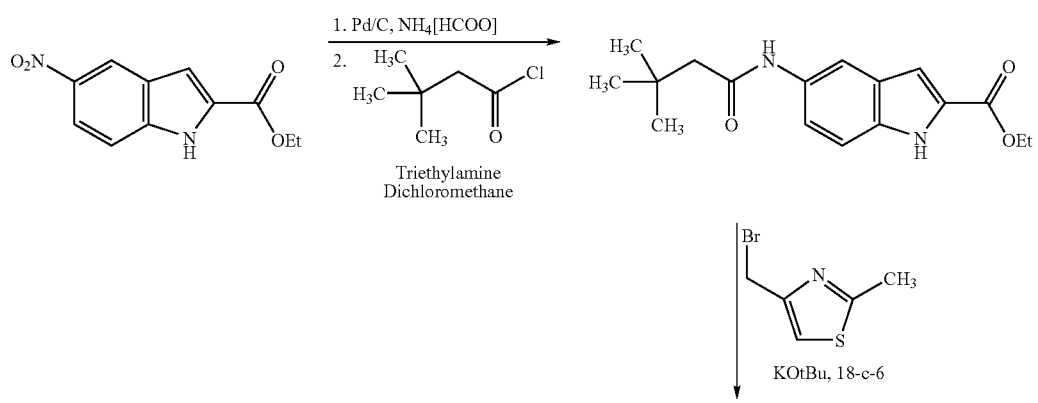
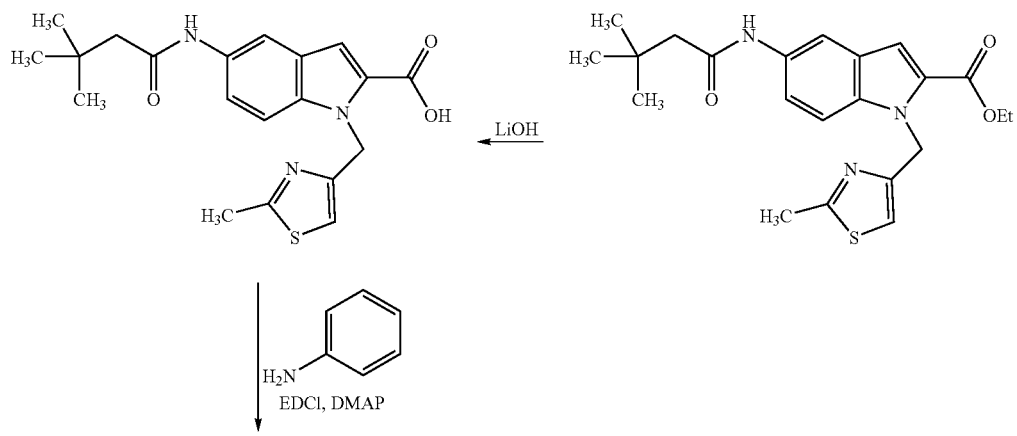

-continued
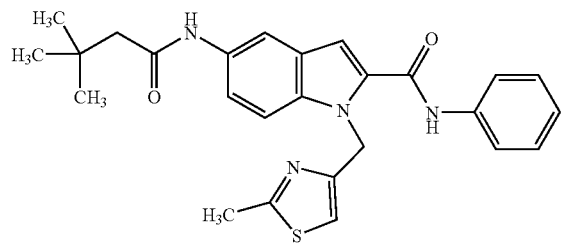
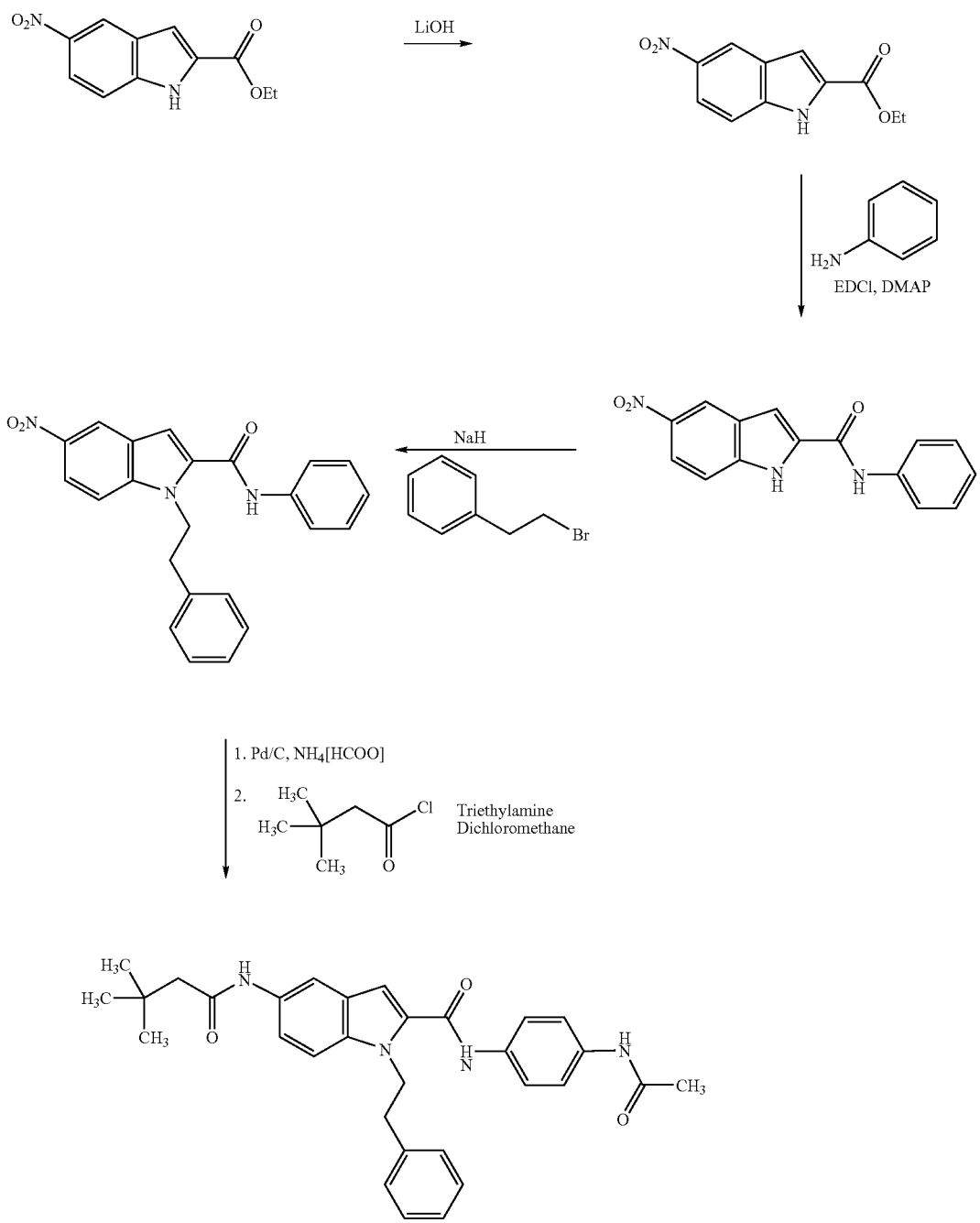

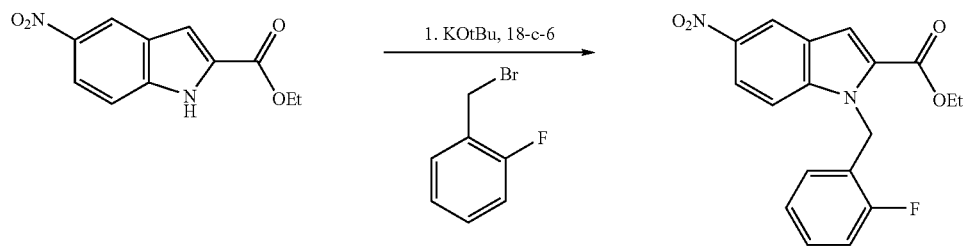
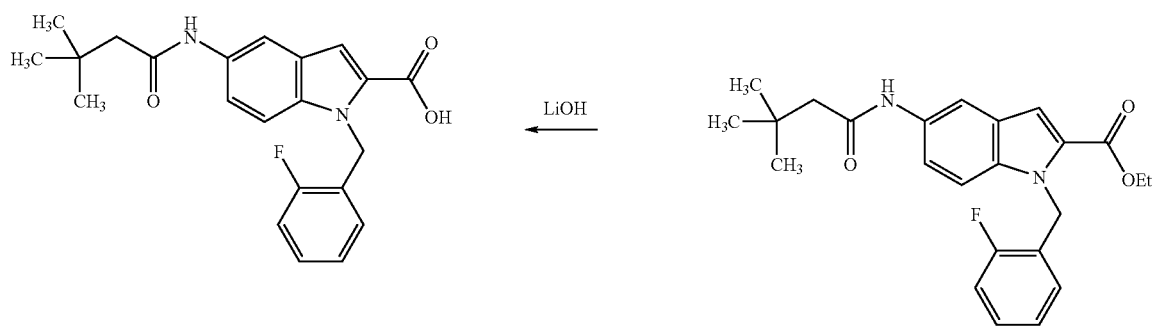
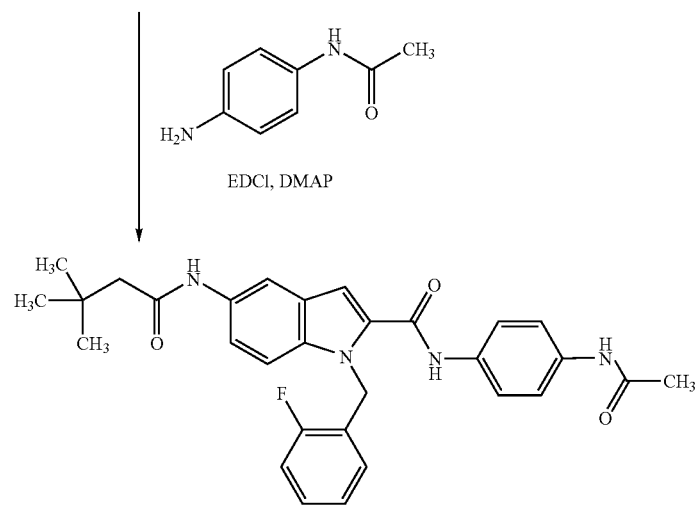

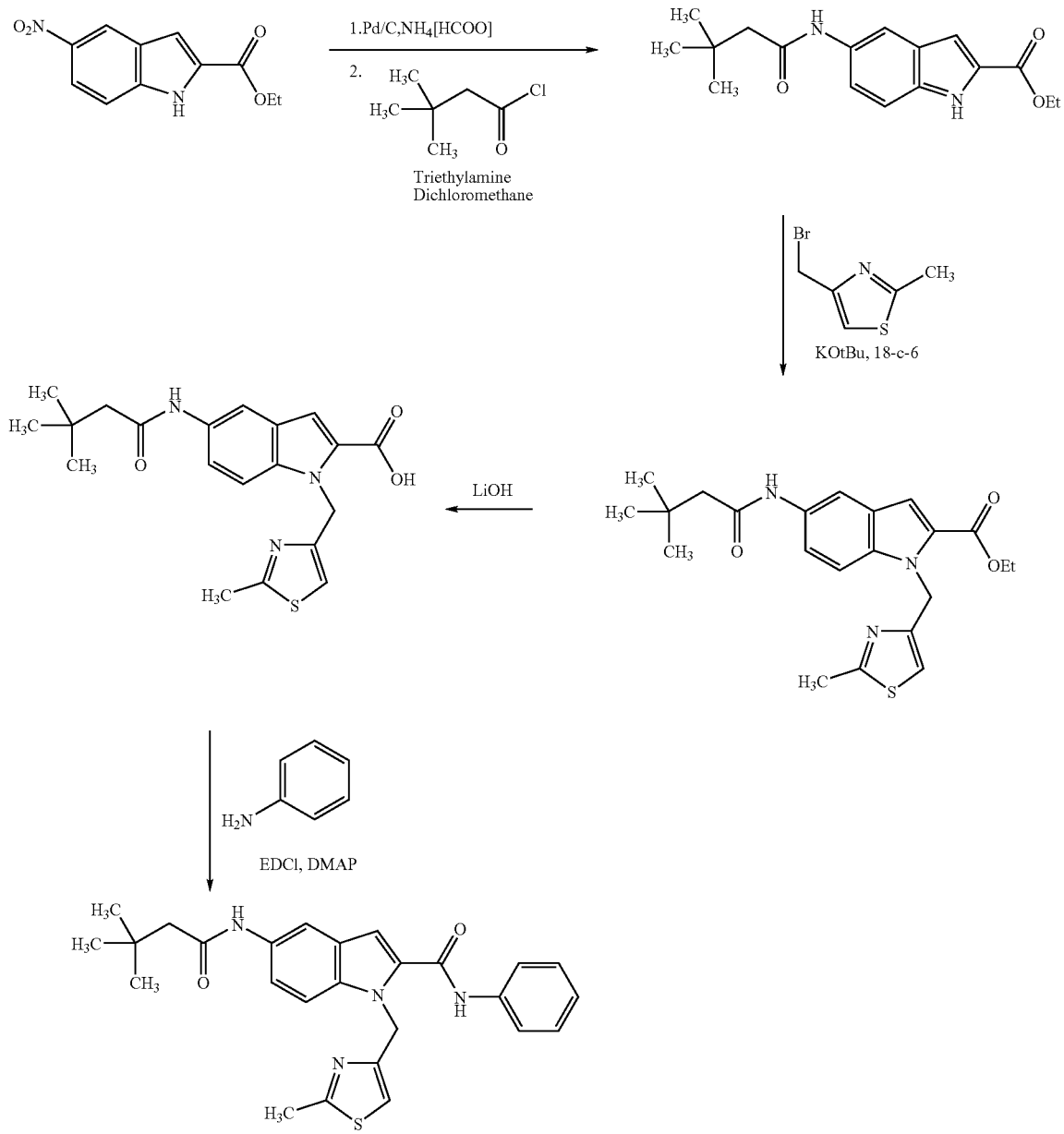

Surprisingly, the compounds of the formula (I) have an unforeseeable useful spectrum of pharmacological activity and are therefore suitable in particular for the prophylaxis and/or treatment of disorders in humans and animals.

The pharmaceutical activity of the compounds of the formula (I) can be explained by their action as ECE inhibitors.

Owing to their pharmacological properties, the compounds of the formula (I) can be used on their own or in combination with one or more other active compounds for the prophylaxis and/or treatment of disorders in human and veterinary medicine, in particular of cardiovascular disorders.

The compounds of the formula (I) are suitable for the prophylaxis and/or treatment of essential, pulmonary and malignant hypertension, of advanced atherosclerosis, myocardial infarction, cardiac insufficiency, heart and kidney failure, of ischaemic disorders such as angina pectoris, myocardial infarction and stroke and of cardial arrhythmia and renal dysfunction.

The present invention also relates to the use of the compounds of the formula (I) for preparing medicaments for the prophylaxis and/or treatment of the syndromes mentioned above.

The present invention furthermore relates to a process for the prophylaxis and/or treatment of the syndromes mentioned above using the compounds of the formula (I).

The present invention furthermore provides medicaments comprising at least one compound of the formula (I), preferably together with one or more pharmacologically acceptable auxiliaries or carriers, and their use for the purposes mentioned above.

The active compound can act systemically and/or locally. For this purpose, it can be administered in a suitable manner, such as, for example, orally, parenterally, pulmonarily, nasally, sublingually, lingually, buccally, rectally, transdermally, conjunctivally, otically, as stents or as an implant.

For these administration routes, the active compound can be administered in suitable administration forms, oral administration being preferred.

For oral administration, known administration forms delivering the active compound rapidly and/or in modified form, such as, for example, tablets (uncoated and coated tablets, for example tablets provided with enteric coatings or film-coated tablets), capsules, sugar-coated tablets, granules, pellets, powders, emulsions, suspensions and solutions, are suitable.

Parenteral administration can be carried out with avoidance of an absorption step (intravenous, intra-arterial, intracardiac, intraspinal or intralumbal) or with involvement of an absorption (intramuscular, subcutaneous, intracutaneous, percutaneous, or intraperitoneal). Suitable administration forms for parenteral administration are, inter alia, injection and infusion preparations in the form of solutions, suspensions, emulsions, lyophilisates and sterile powders.

For the other administration routes, for example, pharmaceutical forms for inhalation (inter alia powder inhalers, nebulizers), nasal drops/solutions, sprays; tablets or capsules to be administered lingually, sublingually or buccally or capsules, suppositories, aural and ophthalmic preparations, vaginal capsules, aqueous suspensions (lotions, shake mixtures), lipophilic suspensions, ointments, creams, milk, pastes, dusting powders or implants are suitable.

The active compounds can be converted in a manner known per se into the application forms mentioned. This is carried out using inert non-toxic, pharmaceutically suitable excipients. These include, inter alia, vehicles (for example microcrystalline cellulose), solvents (for example liquid polyethylene glycols), emulsifiers (for example sodium dodecyl sulphate), dispersing agents (for example polyvinylpyrrolidone), synthetic and natural biopolymers (for example albumin), stabilizers (for example antioxidants such as ascorbic acid), colorants (for example inorganic pigments such as iron oxides) or taste and/or odour corrigents.

In general, it has proved advantageous to administer amounts of approximately 0.001 to 50 mg/kg, preferably approximately 1 to 50 mg/kg, of body weight, in the case of oral administration approximately 0.01 to 25 mg/kg, preferably approximately 0.5 to 5 mg/kg, of body weight, to achieve effective results.

In spite of this, it may be necessary to depart from the amounts mentioned, namely depending on the body weight or the type of administration route, on the individual response towards the medicament, the manner of its formulation and the time or interval at which administration takes place. Thus, in some cases it may be sufficient to manage with less than the abovementioned minimum amount, while in other cases the upper limit mentioned has to be exceeded. In the case of administration of relatively large amounts, it may be advisable to divide these into a number of individual doses over the course of the day.

The present invention is illustrated using the non-limiting preferred examples below; however, the invention is not in any way restricted by these examples.

Unless indicated otherwise, the percentages in the examples below are in each case based on weight; parts are parts by weight.

A. Evaluation of the Physiological Activity

To examine the in vitro action of the compounds according to the invention, the following biological assays may be used:

Functional in Vitro Assay

The ECE activity for identifying the substances described herein originates from the endothelial cell line EA.hy926. The ECE-inhibitory action of the compounds in this invention is tested as described below:

For 12–48 h, EA.hy296 cells are cultivated in a 384-well cell culture dish in 80 µl of cell culture medium (DMEM supplemented with 10% FCS, 2 mM glutamine, 10 mM HEPES, 1 mM sodium pyruvate and 1×HAT (Gibco 21060-017)) in a humid atmosphere (100% atmospheric humidity) enriched with 7% v/v of $CO_2$ at 37° C. After confluence has been reached, and immediately prior to the actual beginning of measurement, the supernatant of the cell culture is pipetted off and replaced by 40 or 80 µl of the same medium to which 1–100 nM bET has been added. After 30–120 minutes under otherwise identical cell culture conditions, the supernatant is pipetted off. Cellular components are removed by centrifugation in a customary bench-top centrifuge (10 000 rpm; 2 minutes). The resulting clear supernatant is either used directly as described below or shock-frozen in dry ice and then stored at −20° C. Directly removed supernatant or thawed, stored supernatant are measured in an enzyme immunoassay (EIA).

To determine the inhibitory activity of ECE inhibitors, EA.hy296 cells are incubated with the test substance in a concentration between 0.001–5 µM under the conditions described above. To minimize possible interference by neutral endopeptidase (NEP24.11), 100 µM of thiophane are added during the bET incubation of the EA.hy926 cells.

The proportion of the ET-1 formed by ECE cleavage is measured as follows: depending on the amount of converted bET, the samples are, prior to use, diluted 2–100-fold with EIA. An appropriate dilution of the cell supernatant is incubated in 100 µl portions for 14–18 hours in the sample tubes of the EIA kit Biomedica B1-20052.

The experimental data are compiled in the table below.

| Example No. | $IC_{50}$ (µM) |
|---|---|
| 7 | 1 |
| 57 | 1.5 |
| 58 | 1.6 |
| 60 | 0.7 |
| 62 | 0.7 |

Big hET-1 Pressor Response in Anaesthetized Rats

Male Wistar rats having a body weight of 300–350 g are anaesthetized using 100 mg/kg i.p. of thiopental. Following tracheotomy, a catheter for monitoring blood pressure and heart frequency is introduced into the femoral artery, and a catheter for substance administration is introduced into the femoral vein. The animals are ventilated with normal air and their body temperature is checked. Ganglia blockade is initiated by intravenous administration of 5 mg/kg of pentolinium in a volume of 1 ml/kg. After 2 minutes, the test substance is administered intravenously in a solution of Transcutol/Cremophor EIJPBS 0.9% (10/10/80=w/w/w) in a volume of 1 ml/kg. Big hET-1 is administered as a dose of 9 µg/kg as intravenous bolus injection in a volume of 1 ml/kg 1 minute after substance administration. The haemodynamic parameters are monitored for 30 minutes.

B. EXAMPLES

| Abbreviations: | |
|---|---|
| aq. | aqueous |
| CDCl$_3$ | deuterochloroform |
| CH | cyclohexane |
| DCI | direct chemical ionization (in MS) |
| DCM | dichloromethane |
| DMAP | 4-dimethylaminopyridine |
| DMF | dimethylformamide |
| DMSO | dimethyl sulphoxide |
| EDC | N-(3-dimethylaminoisopropyl)-N'-ethylcarbodiimide hydrochloride |
| EA | ethyl acetate (acetic acid ethyl ester) |
| EI | electron-impact ionization (in MS) |
| eq | equivalent(s) |
| ESI | electrospray ionization (in MS) |
| m.p. | melting point |
| sat. | saturated |
| h | hour |
| HATU | O-(7-azabenzotriazol-1-yl)-N,N,N',N'-tetramethyluronium hexafluorophosphate |
| HPLC | high-pressure, high-performance liquid chromatography |
| LC-MS | liquid-chromatograph-coupled mass spectroscopy |
| lit. | literature (reference) |
| sol. | solution |
| MW | molecular weight |
| ml | millilitre |
| MS | mass spectroscopy |
| NMR | nuclear magnetic resonance |
| o | ortho |
| p | para |
| p.a. | pro analysi |
| prep. | preparative |
| RF | reflux |
| RP | reverse phase (in HPLC) |
| RT | room temperature |
| R$_t$ | retention time (in HPLC) |
| THF | tetrahydrofuran |
| dil. | dilute |
| cf. | compare |
| vol. | volume |
| decomp. | decomposition |

LC/MS and HPLC Methods:

MHZ2Q=Method 4

| MS unit: | Micromass Quattro LCZ | | | |
|---|---|---|---|---|
| | Ionization: | ESI positive/negative | | |
| HPLC unit: | HP 1100 | | | |
| | UV detector DAD: | 208–400 nm | | |
| | Oven temp.: | 40° C. | | |
| Column: | Symmetry C 18 | | | |
| | 50 mm × 2.1 mm | 3.5 μm | | |
| Gradient | Time (min) | A: % | B: % | Flow rate (ml/min) |
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |

A: acetonitrile + 0.1% formic acid
B: water + 0.1% formic acid

Method 1 (LCMS)=Method MHZ2P01

Instrument: Micromass Platform LCZ, HP1100; column: symmetry C18, 50 mm×2.1 mm, 3.5 μm; eluent A: water+0.05% formic acid, eluent B: acetonitrile+0.05% formic acid; gradient: 0.0 min 90% A→4.0 min 10% A→6.0 min 10% A; oven: 40° C.; flow rate: 0.5 ml/min; UV detection: 208–400 nm.

Method 2 (LCMS)=Method SMKL-ZQ-2

Instrument: Waters Alliance 2790 LC; column: symmetry C18, 50 mm×2.1 mm, 3.5 μm; eluent A: water+0.1% formic acid, eluent B: acetonitrile+0.1% formic acid; gradient: 0.0 min 5% B→5.0 min 10% B→6.0 min 10% B; temperature: 50° C.; flow rate: 1.0 ml/min; UV detection: 210 nm.

Method 3 (LCMS)=Method SMKL__03042001-acid-210

Instrument: Finnigan MAT 900S, TSP: P4000,AS3000, UV3000HR; column: symmetry C18, 150 mm×2.1 mm, 5.0 μm; eluent C: water, eluent B: water+0.3 g 35% strength HCl, eluent A: acetonitrile; gradient: 0.0 min 2% A→2.5 min 95% A→5 min 95% A; oven: 70° C.; flow rate: 1.2 ml/min; UV detection: 210 nm.

Method 4 (LCMS)=Method MHZ2Q

Method 5 (LCMS)=Method SMKL_ZQ-5-CS

MS unit: Micromass ZQ; HPLC unit: Waters Alliance 2790; column: symmetry C18, 50 mm×2.1 mm, 3.5 μm; eluent B: acetonitrile+0.05% formic acid, eluent A: water+0.05% formic acid; gradient: 0.0 min 10% B→3.5 min 90% B→5.5 min 90% B; oven: 50° C.; flow rate: 0.8 ml/min; UV detection: 210 nm.

Method 6 (HPLC)=Method SYA-HPPSK2

Instrument: BP 1100 with DAD detection; column: Kromasil RP-18, 60 mm×2 mm, 3.5 μm; eluent: A=5 ml HClO4/l H$_2$O, B=ACN; gradient: 0 min 2% B, 0.5 min 2% B, 4.5 min 90% B, 6.5 min 90% B; flow rate: 0.75 ml/min; temp.: 0° C.; detection UV210 nm.

Method 7 (HPLC)=Method SMKL-N-1-1-Low Vol ACN-HCl-210.met

Instrument: 1 column: symmetry C18 2.1×150 mm; eluent: A=ACN, B=0.6 g 30% strength HCl/water; gradient: 0 min 10% A flow rate 0.60 ml/min, 4 min 90% A flow rate 0.60 ml/min, 9 min 90% A flow rate 0.80 ml/min; temp.: 50° C.; UV detection 210 nm.

Starting materials

Example I

Ethyl 5-nitro-1-propyl-1H-indole-2-carboxylate

Under argon, 937 mg (4.00 mmol) of ethyl 5-nitro-1H-indole-2-carboxylate (A. Guy, J.-P. Guetté, *Synthesis* 1980, 222–223) are initially charged in 12 ml of dimethyl sulphoxide. 4.40 mmol of sodium hydride (176 mg of a 60% dispersion in paraffin) are added a little at a time, and the mixture is stirred at 50° C. for 30 min. After cooling to RT, 170 mg (4.40 mmol) of propyl iodide are added, and the mixture is stirred at RT for another 3 h. The reaction mixture is poured into 30 ml of water and extracted with ethyl acetate (6×30 ml). The combined organic phases are washed with 50 ml of sat. sodium chloride sol., dried over sodium sulphate and freed from the solvent using a rotary evaporator. The resulting brown crude product is purified by column chromatography (silica gel 60, mobile phase gradient cyclohexane→cyclohexane-ethyl acetate 3:1), giving the product as second fraction.

Yield: 958 mg (3.48 mmol, 77% of theory).

MS (DCI): m/z=294 (M+NH$_4$)$^+$.

$^1$H-NMR (500 MHz, DMSO-d$_6$): δ=8.76 (d, 1H), 8.17 (dd, 1H), 7.89 (d, 1H), 7.58 (s, 1H), 4.60 (dd, 2H), 4.36 (q, 2H), 1.74 (sextet, 2H), 1.35 (t, 3H), 0.84 (t, 3H).

Example II

Ethyl 1-(2-fluorobenzyl)-5-nitro-1H-indole-2-carboxylate

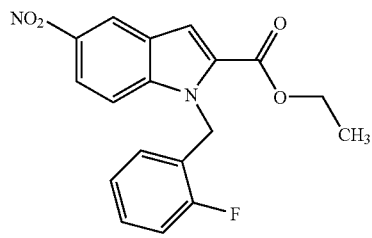

The preparation is carried out as described for Example I using 940 mg (4.00 mmol) of ethyl 5-nitro-1H-indole-2-carboxylate and 780 mg (4.15 mmol) of 2-fluorobenzyl bromide, reaction time 6 h.

Yield: 980 mg (72% of theory).

MS (DCI): m/z=360 (M+NH$_4$)$^+$.

$^1$H-NMR (300 MHz, DMSO-d$_6$): δ=8.80 (d, 1H), 8.17 (dd, 1H), 7.82 (d, 1H), 7.68 (d, 1H), 7.35–7.18 (m, 2H), 7.03 (dt, 1H), 6.56 (dt, 1H), 5.98 (s, 2H), 4.29 (q, 2H), 1.27 (t, 3H).

Example III

5-Nitro-1-propyl-1H-indole-2-carboxylic acid

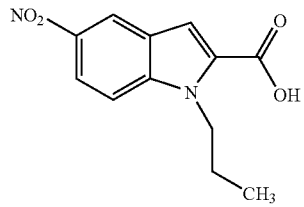

236 mg (3.68 mmol, 85% pure) of potassium hydroxide (powder) are initially charged in 10 ml of dimethyl sulphoxide, 961 mg (3.48 mmol) of the compound from Example I are added and the reaction mixture is stirred at RT for half an hour. The reaction mixture is poured into about 100 ml of water and with cooling, 10% strength hydrochloric acid is added a little at a time to the solution until no more precipitate is formed. The precipitated solid is filtered off with suction and dried in a desiccator under reduced pressure overnight.

Yield: 812 mg (94% of theory)

m.p.: 197° C.

$^1$H-NMR (300 MHz, DMSO-d$_6$): δ=13.33 (br. S, 1H), 8.73 (d, 1H), 8.15 (dd, 1H), 7.85 (d, 1H), 7.53 (s, 1H), 4.61 (t, 2H), 1.74 (sextet, 2H), 0.83 (t, 3H).

Example IV 1-(2,6-Difluorobenzyl)-5-nitro-1H-indole-2-carboxylic acid

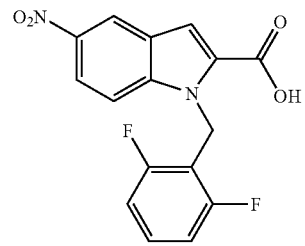

Under an atmosphere of argon, 5.49 g (83.2 mmol, 85% pure) of potassium hydroxide (powder) are initially charged in 110 ml of dimethyl sulphoxide, 6.43 g (27.5 mmol) of ethyl 5-nitro-1H-indole-2-carboxylate (A. Guy, J.-P. Guetté, Synthesis 1980, 222–223) are added at RT and the mixture is stirred for 30 min. With ice-cooling, at an internal temperature of 5–10° C., 2,6-difluorobenzyl chloride (10.0 g, 61.5 mmol) is then added dropwise over a period of 15 min, and the mixture is stirred at RT for 16 h. For work-up, the mixture is poured into 500 ml of water and acidified with dil. hydrochloric acid and the precipitated solid is filtered off with suction and pre-purified chromatographically on silica gel 60 (mobile phase gradient dichloromethane→dichloromethane-methanol 3:1). The resulting product is recrystallized from ethanol. This gives 4.33 g (47% of theory) of a pale-yellow crystalline solid.

MS (ESIpos): m/z=333 (M+H)$^+$.

$^1$H-NMR (300 MHz, DMSO-d$_6$): δ=13.41 (br. s, 1H), 8.72 (d, 1H), 8.17 (dd, 1H), 7.71 (d, 1H, 7.54 (s, 114), 7.37 (m, 1H), 7.05 (t and m, 2H), 6.07 (s, 2H).

Example V 1-(2-Fluorobenzyl)-5-nitro-1H-indole-2-carboxylic acid

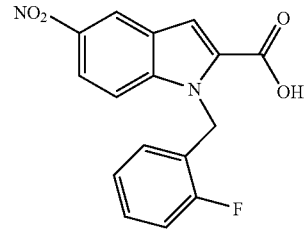

Preparation analogously to Example III using 877 mg (2.56 mmol) of the compound from Example II. Yield: 732 mg (91% of theory)

m.p.: 223° C.

MS (DCI): m/z=332 (M+NH$_4$)$^+$.

¹H-NMR (500 MHz, DMSO-d₆): δ=13.49 (br. s, 1H), 8.79 (d, 1H), 8.15 (dd, 1H), 7.78 (d, 1H), 7.61 (s, 1H), 7.29 (m, 1H), 7.23 (m, 1H), 7.03 (t, 1H), 6.52 (t, 1H), 620 (s, 2H).

Example VI 1-(2,7-Difluorobenzyl)-N-(3-methylphenyl)-5-nitro-1H-indole-2-carboxamide

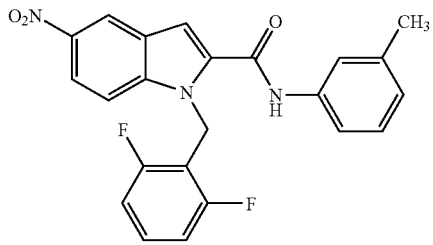

A little at a time, the compound from Example IV (1.40 g, 4.21 mmol) is introduced into 10 ml of thionyl chloride, and after the addition has ended, the mixture is stirred at the boil. After 60 min, the mixture is concentrated and the residue is mixed 3 times with about 50 ml of toluene each time and reconcentrated. The resulting indolecarbonyl chloride is taken up in 50 ml of dichloromethane and, at 0° C., 2.94 ml (21.1 mmol) of triethylamine and then 587 mg (5.48 mmol) of 3-methylaniline are added. The mixture is stirred at room temperature for 16 h. The reaction solution is poured into 200 ml of water, the organic solvent is removed from the mixture using a rotary evaporator and the precipitated solvent is filtered off with suction and dried. This gives 1.48 g (76% of theory) of product.

MS (DCI): m/z=439 (M+NH₄)⁺.

¹H-NMR (300 MHz, DMSO-d₆): δ=10.53 (s, 1H), 8.74 (d, 1H), 8.17 (dd, 1H), 7.75 (d, 1H), 7.60–7.47 (m, 3H), 7.36 (m, 1H), 7.24 (t, 1H), 7.05 (t, 2H); 6.95 (d, 1H), 6.05 (s, 2H), 2.32 (s, 3H).

Example VII 1-(2-Fluorobenzyl)-5-nitro-N-phenyl-1H-indole-2-carboxamide

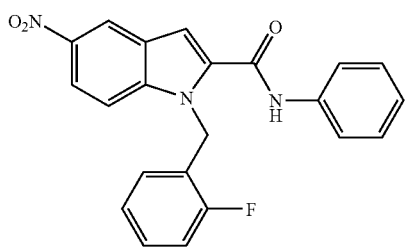

Reaction of 500 mg (1.59 mmol) of the compound from Example V and 163 mg (1.75 mmol) of aniline as described for Example VI. The reaction time is about 30 min. For work-up, the reaction mixture is poured into 100 ml of water and extracted with dichloromethane (4×50 ml), and the combined organic phases are dried over sodium sulphate and concentrated. Yield: 610 mg (98% of theory). For characterization, a sample of the resulting product is recrystallized from ethanol, the main quantity is directly used further.

MS (DCI): m/z=407 (M+NH)⁺.

H-NMR (400 MHz, DMSO-d₆): δ=10.62 (s, 1H), 8.81 (d, 1H), 8.16 (dd, 1H), 7.81 (d, 1H), 7.72 (d, 2H), 7.65 (s, 1H), 7.36 (t, 2H), 7.32–7.16 (m, 2H), 7.12 (t, 1H), 7.04 (dt, 1H), 6.75 (dt, 1H), 6.00 (s, 2H).

Example VIII 1-(2,6-Difluorobenzyl)-5-nitro-N-phenyl-1H-indole-2-carboxamide

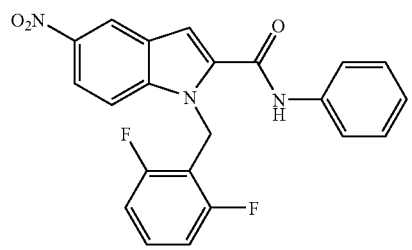

Preparation from the appropriate starting materials as described for Example VI.

MS (ESIpos): m/z=408 (M+H)⁺.

Example IX 1-(2-Fluorobenzyl)-5-nitro-N-(3-pyridinyl)-1H-indole-2-carboxamide

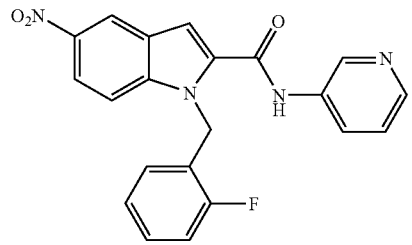

Preparation from the appropriate starting materials as described for Example VII. The product obtained after work-up is suspended in diethyl ether, filtered off with suction and dried.

m.p.: 234° C. (decomp.)

MS (ESIpos): m/z=391(M+H)⁺.

Example X 1-(2-Fluorobenzyl)-N-(4-methoxyphenyl)-5-nitro-1H-indole-2-carboxamide

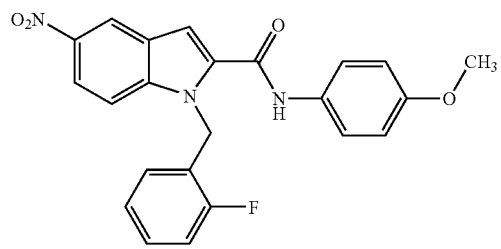

Preparation from the appropriate starting materials as described for Example VII. The product obtained after work-up is suspended in diethyl ether, filtered off with suction and dried.

m.p.: 233° C.
MS (ESIpos): m/z=420 (M+H)⁺.

Example XI 1-(2-Fluorobenzyl)-N-(3-methoxyphenyl)-5-nitro-1H-indole-2-carboxamide

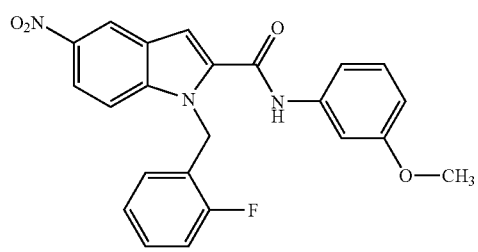

Preparation from the appropriate starting materials as described for Example VII. The product which precipitates from the reaction solution is suspended in diethyl ether, filtered off with suction and dried.

m.p.: 203° C.
MS (ESIpos): m/z=420 (M+H)⁺.

Example XII 1-(2-Fluorobenzyl)-N-(3-methylphenyl)-5-nitro-1H-indole-2-carboxamide

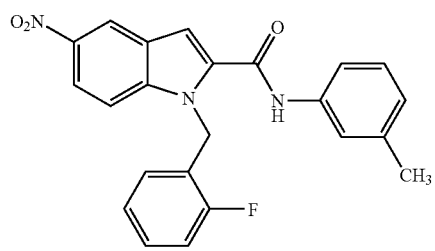

Preparation from the appropriate starting materials as described for Example VII. The product which precipitates from the reaction solution is suspended in diethyl ether, filtered off with suction and dried.

m.p.: 211° C.
MS (ESIpos): m/z=404 (M+H)⁺.

Example XIII

5-Nitro-N-phenyl-1-propyl-1H-indole-2-carboxamide

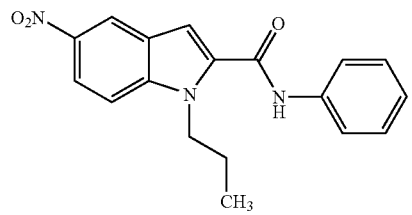

Preparation from the appropriate starting materials as described for Example VII. The product obtained after work-up is reacted further without further purification.

m.p.: 201–205° C.
MS (ESIpos): m/z=0.324 (M+H)⁺.

Example XIV

5-Amino-1-(2,6-difluorobenzyl)-N-(3-methylphenyl)-1H-indole-2-carboxamide

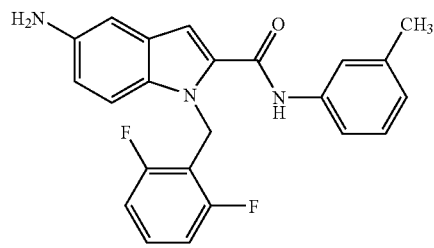

1.38 g (3.28 mmol) of the compound from Example VI are initially charged in 100 ml of ethanol. 3.70 g (16.4 mmol) of tin(II) chloride dihydrate are then added, and the mixture is stirred at the boil for 16 h. The reaction solution is poured into about 200 ml of water and made alkaline using dil. aqueous sodium hydroxide solution and extracted with ethyl acetate (5×50 ml). The combined org. phases are washed with 50 ml of sat. sodium chloride solution, dried over sodium sulphate and concentrated. For characterization, a sample of the resulting light-brown product (1.19 g, 85% of theory) is purified by prep. HPLC (GROM-SIL 120 OSD4 HE, 10 μm, mobile phase gradient acetonitrile-water 30:70→95:5), the main quantity is directly used further.

MS (ESIpos): m/z=392 (M+H)⁺.
$^1$H-NMR (200 MHz, DMSO-$d_6$): δ=10.20 (s, 1H), 7.64 (s, 1H), 7.56 (d, 1H), 7.43–7.13 (m, 3H), 7.12–6.85 (m, 4H), 6.73 (s, 1H), 6.65 (d, 1H), 5.89 (s, 2H), 4.70 (s, 2H), 2.31 (s, 3H).

The compounds listed in the table below are prepared analogously to Example XIV.

| Example | Structure | Analytical data |
|---------|-----------|-----------------|
| XV | 5-amino-1-(2,6-difluorobenzyl)-N-phenyl-1H-indole-2-carboxamide | MS(ESIpos): m/z = 378(M + H)⁺. |
| XVI | 5-amino-1-(2-fluorobenzyl)-N-phenyl-1H-indole-2-carboxamide | m.p.: 198° C.<br>MS(ESIpos): m/z = 360(M + H)⁺. |
| XVII | 5-amino-1-(2-fluorobenzyl)-N-(4-methoxyphenyl)-1H-indole-2-carboxamide | m.p. 222° C.(decomp.)<br>MS(ESIpos): m/z = 390(M + H)⁺. |
| XVIII | 5-amino-1-(2-fluorobenzyl)-N-(3-methoxyphenyl)-1H-indole-2-carboxamide | mp.: 185° C.(decomp.)<br>MS(ESIpos): m/z = 390(M + H)⁺. |
| XIX | 5-amino-1-(2-fluorobenzyl)-N-(3-methylphenyl)-1H-indole-2-carboxamide | LC-MS(method MHZ2Q):<br>$R_t$ = 3.19 min<br>MS(ESIpos): m/z = 374(M + H)⁺. |
| XX | 5-amino-N-phenyl-1-propyl-1H-indole-2-carboxamide | $^{1}$H-NMR(200 MHz, DMSO-d$_6$): δ = 10.16(s, 1H), 7.76 (d, 2H), 7.33(m, 3H), 7.16–6.93(m, 2H), 6.71(m, 2H), 4.72(br. s, 2H), 4.42 (t, 2H), 1.68(m, 2H), 0.81(t, 3H). |

Example XXI

Ethyl 1-(2,4-difluorobenzyl)-5-nitro-1H-indole-2-carboxylate

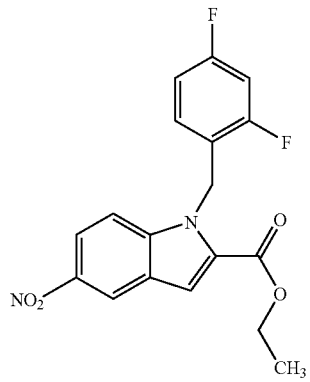

Under argon, 214 mg (0.81 mmol) of 1,4,7,10,13,16-hexaoxacyclooctadecane (18-crown-6) are initially charged in 43 ml of THF, and 9.73 ml (9.73 mmol) of 1-molar potassium tert-butoxide solution in THF and 2000 mg (8.11 mmol) of ethyl 5-nitro-1H-indole-2-carboxylate are added. The mixture is stirred at RT for 15 minutes and then cooled to 0° C. A solution of 1713 mg (8.11 mmol) of 2,4-difluorobenzyl bromide in 13 ml of TKF is slowly added dropwise. The ice-bath is removed and the mixture is stirred at RT for 1 hour. For work-up, the mixture is diluted with water and the THF is removed under reduced pressure using a rotary evaporator. The aqueous residue is extracted with ethyl acetate and the organic phase is washed with sat. sodium chloride solution, dried with sodium sulphate, filtered and dried under reduced pressure. The residue is purified by column chromatography (mobile phase: cyclohexane:ethyl acetate 5:1).

Yield: 888 mg (29% of theory)
LC/MS (method 3): $R_t$=3.07 min
MS (EI): m/z=361 (M+H)$^+$ $^1$H-NMR (200 MHz, DMSO-d$_6$): δ=1.27 (t, 3H), 4.29 (q, 2H), 5.94 (s, 2H), 6.57–6.73 (m, 1H), 6.87–7.01 (m, 1H), 7.21–7.37 (m, 1H), 7.68 (s, 1H), 7.85 (d, 1 H), 8.19 (dd, 1H), 8.81 (d, 1H).

Example XXII

1-(2,4-Difluorobenzyl)-5-nitro-1H-indole-2-carboxylic acid

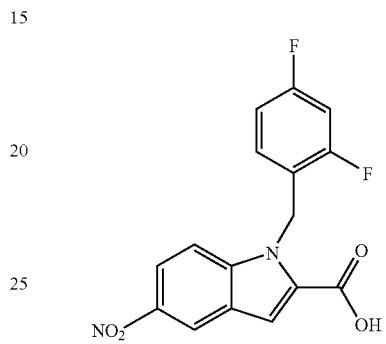

880 mg (2.44 mmol) of ethyl. 1-(2,4-difluorobenzyl)-5-nitro-1H-indole-2-carboxylate from Example XXI are initially charged in 11 ml of THF and 11 ml of methanol. 2.44 ml (4.88 mmol) of 2-molar lithium hydroxide solution are added, and the mixture is heated at 90° C. for 30 minutes. The mixture is cooled and diluted with aqueous hydrochloric acid and ethyl acetate. The organic phase is washed with sat. sodium chloride solution, dried with sodium sulphate, filtered and dried under reduced pressure.

Yield: 831 mg (100% of theory)
LC/MS (method 4): $R_t$=4.26 min
MS (EI): m/z=331 (M–H)$^+$ $^1$H-NMR (400 MHz, DMSO-d$_6$): δ=5.97 (s, 2H), 6.64 (dd, 1H), 6.90–6.98 (m, 1H), 7.24–7.32 (m, 1H), 7.59 (s, 1H), 7.78 (d, 1H), 8.15 (dd, 1H), 8.77 (dd, 1H), 13.47 (br. s, 1H).

The following compound is prepared analogously to the procedure described in Example VI:

| Example | Structure | Analytical data |
|---|---|---|
| XXIII | ![structure] | LC/MS(method 4): $R_t$ = 3.08 min<br>MS(EI): m/z = 391(M + H)$^+$ |

Example XXIV

1-(2,4-Difluorobenzyl)-N-(4-fluorophenyl)-5-nitro-1H-indole-2-carboxamide

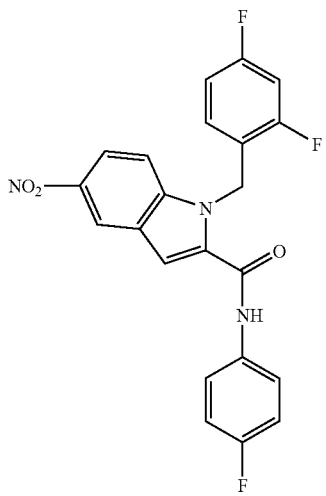

389 mg (1.17 mmol) of 1-(2,4-difluorobenzyl)-5-nitro-1H-indole-2-carboxylic acid from Example XXII, 336 mg (1.76 mmol) of N'-(3-dimethylaminopropyl)-N-ethyl-carbodiimide×HCl and 71.5 mg (0.59 mmol) of 4-dimethylaminopyridine are initially charged in 30 ml of a 10:1 dichloromethane:DMF mixture. 156 mg (0.13 ml, 1.40 mmol) of 4-fluoroaniline are added, and the mixture is stirred at RT for 4 hours. For work-up the mixture is diluted and extracted with aqueous hydrochloric acid and ethyl acetate. The organic phase is washed with sat. sodium chloride solution, dried with sodium sulphate, filtered and dried under reduced pressure.

Yield: 485 mg (62% of theory)
LC/MS (method 1): $R_t$=5.00 min
MS (EI): m/z=424 (M–H)$^+$
$^1$H-NMR (400 MHz, DMSO-$d_6$): δ=5.94 (s, 2H), 6.82–6.90 (m, 1H), 6.92–6.99 (m, 1H), 7.12–7.34 (m, 4H), 7.64 (s, 1H), 7.71–7.77 (m, 2H), 7.82 (d, 1H), 8.16 (dd,1H), 8.80 (d, 1H).

The following compounds are prepared analogously to the procedure described in Example XXIV:

| Example | Structure | Analytical data |
|---|---|---|
| XXV | 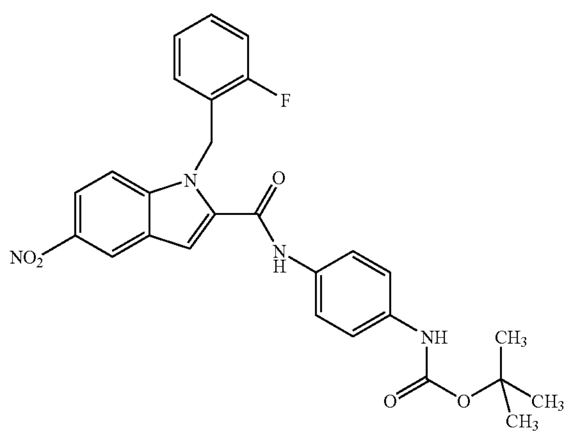 | LC/MS(method 1):<br>$R_t$ = 5.17 min<br>MS(EI): m/z = 503(M – H)$^+$ |
| XXVI | 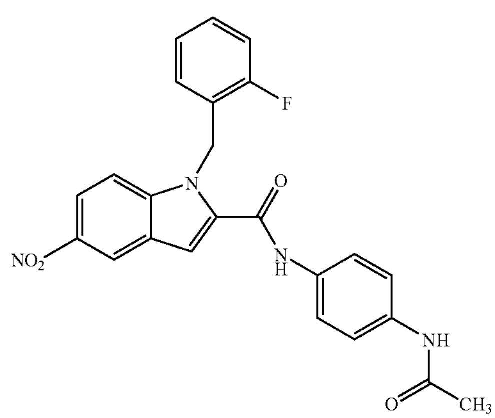 | LC/MS(method 1):<br>$R_t$ = 4.40 min<br>MS(EI): m/z = 447(M + H)$^+$ |

The following compound is prepared analogously to the procedure described in Example XIV:

| Example | Structure | Analytical data |
|---|---|---|
| XXVII | 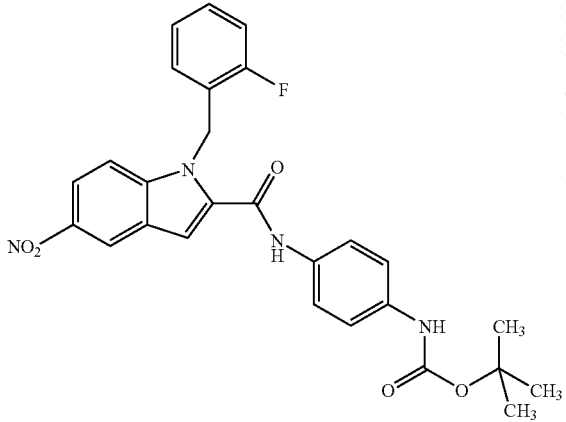 | HPLC(method 1): $R_t$ = 3.60 min<br>MS(EI): m/z = 361(M + H)$^+$<br>$^1$H-NMR(300 MHz, DMSO-$d_6$): δ = 4.78(br.s, 2H), 5.81(s, 2H), 6.58(t, 1H), 6.72(dd, 1H), 6.81(d, 1H), 6.99(t, 1H), 7.13–7.29(m, 4H), 7.72(dd, 2H), 8.42(d, 2H), 10.50(s, 1H). |

Example XXVIII

5-Amino-1-(2,4-difluorobenzyl)-N-(4-fluorophenyl)-1H-indole-2-carboxamide

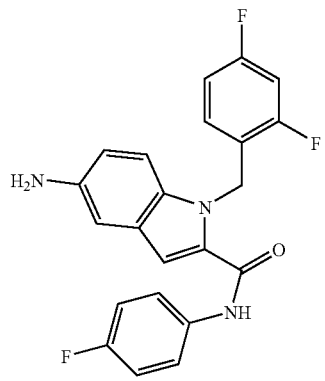

485 mg (1.14 mmol) of 1-(2,4-difluorobenzyl)-N-(4-fluorophenyl)-5-nitro-1H-indole-2-carboxamide from Example XXIV are initially charged in ethyl acetate and ethanol. 287 mg (4.56 mmol) of ammonium formate and 49 mg of palladium on activated carbon (10%) are added. The mixture is heated to reflux, and at 50° C. gas evolves. To bring the reaction to completion, the same amounts of ammonium formate and palladium as above are added. After a further 3 hours at reflux, the mixture is cooled and filtered off through kieselguhr, which is washed with 500 ml of ethanol. The solvent is removed under reduced pressure and the residue is dried.

Yield: 546 mg (100% of theory)

LC/MS (method 1): $R_t$=3.40 min

MS (EI): m/z=396 (M+H)$^+$ $^1$H-NMR (200 MHz, DMSO-$d_6$): δ=5.76 (s, 2H), 6.57–6.74 (m, 2H), 678 (s, 1H), 6.84–6.99 (m, 1H), 7.03–7.35 (m, 5H), 7.66–7.82 (m, 2H), 10.29 (s, 1H)NH$_2$ not detectable.

The following compounds are prepared analogously to the procedure described in Example XXVIII:

| Example | Structure | Analytical data |
|---|---|---|
| XXIX | 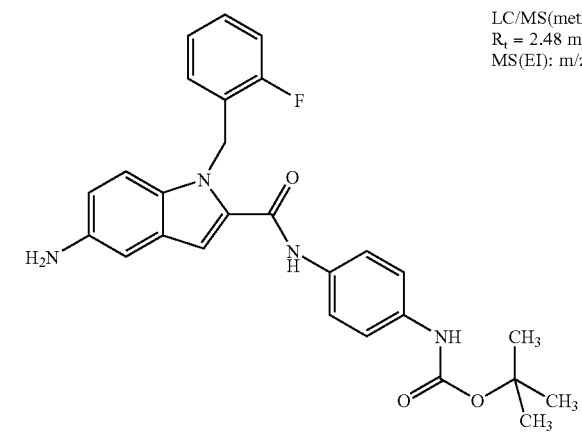 | LC/MS(method 2): $R_t$ = 2.48 min<br>MS(EI): m/z = 473(M − H)$^+$ |

| Example | Structure | Analytical data |
|---|---|---|
| XXX | 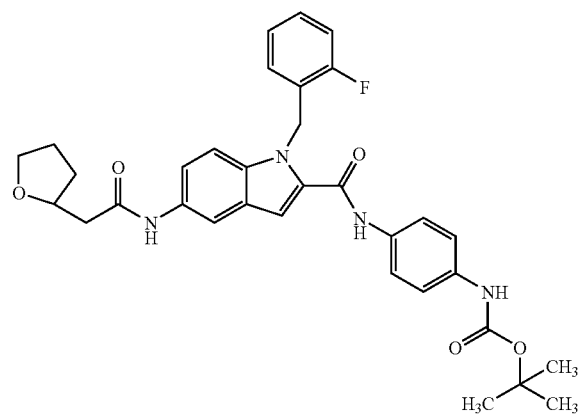 | LC/MS(method 2); $R_t$ = 1.52 and 1.67 min<br>MS(EI): m/z = 415(M − H)+ |

Example XXXI tert-Butyl 4-[({1-(2-fluorobenzyl)-5-[(tetrahydro-2-furanylacetyl)amino]-1H-indol-2-yl}carbonyl)amino]phenylcarbamate 49 mg (0.38 mmol) of tetrahydro-2-furanylacetic acid, 19.3 mg (0.16 mmol) of 4-dimethylaminopyridine and 91 mg (0.47 mmol) of N'-(3-dimethylaminopropyl)-N-ethylcarbodiimide×HCl are added to 3 ml of DMF. 150 mg (0.32 mmol) of tert-butyl 4-({[5-amino-1-(2-fluorobenzyl)-1H-indol-2-yl]carbonyl}amino)phenyl-carbamate from Example XXIX are added. The mixture is stirred at RT for 5 hours. For work-up, the mixture is diluted and extracted with dichloromethane and aqueous hydrochloric acid. The organic phase is washed with sat. sodium bicarbonate solution, dried with sodium sulphate, filtered and concentrated under reduced pressure using a rotary evaporator. The residue is purified by preparative HPLC.

Yield: 115 mg (62%0 of theory)
LC/MS (method 2): $R_t$=3.57 min
MS (EI): m/z=587 (M+H)+

The following compounds are prepared analogously to the procedure described in Example XXXI:

| Example | Structure | Analytical data |
|---|---|---|
| XXXII | 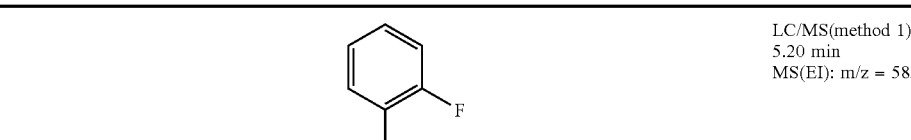 | LC/MS(method 1): $R_t$ = 5.20 min<br>MS(EI): m/z = 583(M − H)+ |

| Example | Structure | Analytical data |
|---|---|---|
| XXXIII | 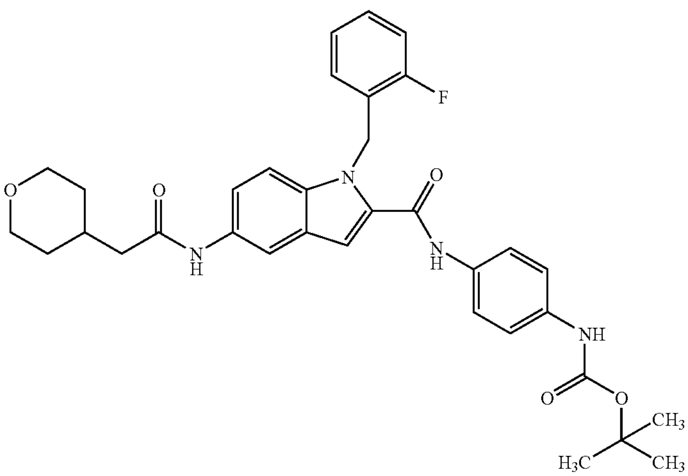 | LC/MS(method 2): R$_t$ = 3.50 min<br>MS(EI): m/z = 599(M − H)$^+$ |
| XXXIV | 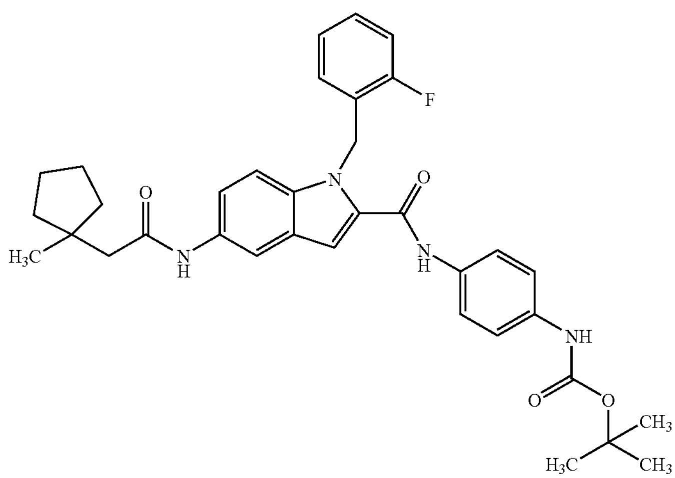 | LC/MS(method 1): R$_t$ = 5.42 min<br>MS(EI): m/z = 597(M − H)$^+$ |

Example XXXV

N-(4-Aminophenyl)-1-(2-fluorobenzyl)-5-[(tetrahydro-2H-pyran-4-yl acetyl)amino]-1H-indole-2-carboxamide hydrochloride 121 mg (0.20 mmol) of tert-butyl-4-[({1-(2-fluorobenzyl)-5-[(tetrahydro-2H-pyran-4-ylacetyl)amino]-1H-indol-2-yl}carbonyl)amino]phenylcarbamate from Example XXXIII, 1.40 ml of dioxane and 1.40 ml of conc. hydrochloric acid are combined and stirred at RT for one hour. The mixture is evaporated to dryness using a rotary evaporator.

Yield: 126 mg (64% of theory)
LC/MS (method 2): R$_t$=2.22 min
MS (EI): m/z=501 (M+H—HCl)$^+$

Example XXXVI

Ethyl 5-amino-1-(2-fluorobenzyl)-1H-indole-2-carboxylate

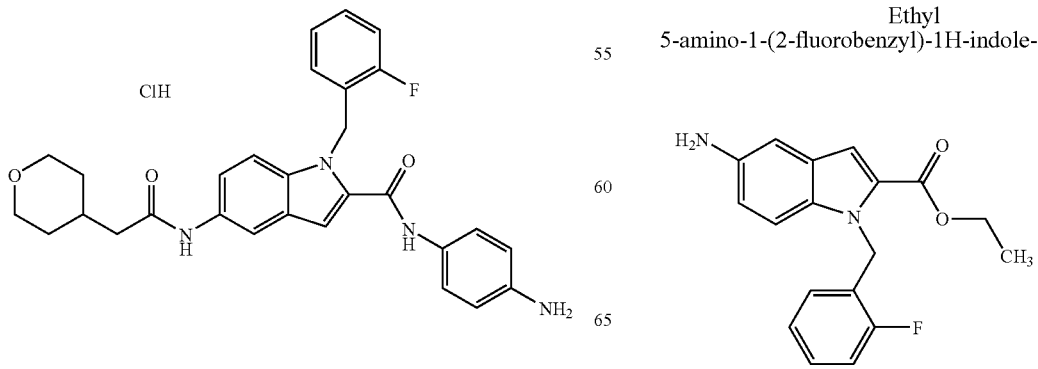

27.84 g (81.33 mmol) of ethyl 1-(2-fluorobenzyl)-5-nitro-1H-indole-2-carboxylate from Example II are initially charged in 750 ml of ethyl acetate and 750 ml of ethanol. 20.51 g (325.31 mmol) of ammonium formate and 2.78 g of palladium on activated carbon are added. The mixture is boiled at reflux and, after one hour, cooled and filtered off through kieselguhr. The filter cake is washed with ethyl acetate. The solvent is removed under reduced pressure and the residue is dried.

Yield: 23.2 g (86% of theory)
HPLC (method 6): $R_t$=4.15 min
MS (ESIpos): m/z=313 (M+H)$^+$ Example XXXVII Ethyl 5-[(3,3-dimethylbutanoyl)amino]-1-(2-fluorobenzyl)-1H-indole-2-carboxylate

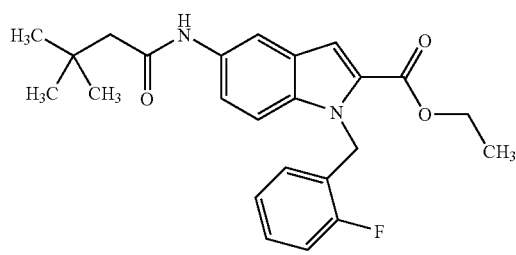

23.2 g (74.28 mmol) of ethyl 5-amino-1-(2-fluorobenzyl)-1H-indole-2-carboxylate from Example XXXVI and 15.03 g (20.71 ml, 148.56 mmol) of triethylamine are added to 300 ml of dichloromethane. The mixture is cooled to 0° C., and a solution of 11 g (11.35 ml, 81.71 mmol) of 3,3-dimethylbutyryl chloride in 300 ml of dichloromethane is added. The mixture is stirred at RT overnight and, for work-up, poured into water. The pH is adjusted to 7 and the mixture is extracted 3 times with ethyl acetate. The combined organic phases are dried over sodium sulphate, filtered and concentrated under reduced pressure.

Yield: 31.7 g (100% of theory)
HPLC (method 6): $R_t$=5.18 min
MS (ESIpos): m/z=411 (M+H)$^+$ Example XXXVIII Ethyl 1-(2-fluorobenzyl)-5-{[(2methyl-1,3-dioxolan-2-yl)acetyl]amino}-1H-indole-2-carboxylate

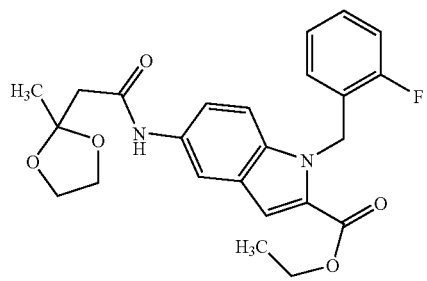

140 mg (0.96 mmol) of (2-methyl-1,3-dioxolan-2-yl)acetic acid are added to 5 ml of DMF, and 547 mg (1.44 mmol) of O-(7-azabenzotriazol-1-yl)-N,N,N',N'-tetramethyluronium hexafluorophosphate and 186 mg (0.25 ml, 1.44 mmol) of N,N-diisopropylethylamine are added. 300 mg (0.96 mmol) of ethyl 5-amino-1-(2-fluorobenzyl)-1H-indole-2-carboxylate from Example XXXVI are added. The mixture is stirred at RT for 3 hours. For work-up the DMF is removed using a rotary evaporator. The residue is taken up in dichloromethane and extracted with aqueous hydrochloric acid. The organic phase is dried with sodium sulphate, filtered and dried under reduced pressure.

Yield: 254 mg (44% of theory)
LC/MS (method 5): $R_t$=2.98 min
MS (EI): m/z=441 (M+H)$^+$ Example XXXIX 5-[(3,3-Dimethylbutanoyl)amino]-1-(2-fluorobenzyl)-1H-indole-2-carboxylic acid

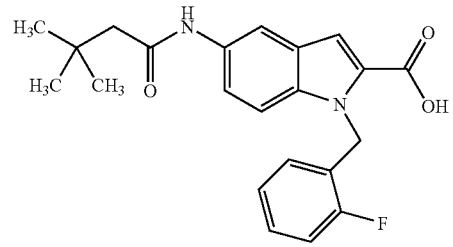

Preparation analogously to Example XXII using 12.50 g (31.53 mmol) of ethyl 5-[(3,3-dimethylbutanoyl)amino]-1-(2-fluorobenzyl)-1H-indole-2-carboxylate from Example XXXVII and 31.5 ml (63.0 mmol) of 2 M lithium hydroxide solution.

Yield: 9.93 g (81% of theory)
HPLC (method 6): $R_t$=4.57 min
MS (ESIpos): m/z=383 (M+H)$^+$ Example XL 1-(2-Fluorobenzyl)-5-{[(2-methyl-1,3-dioxolan-2-yl)acetyl]amino}-1H-indole-2-carboxylic acid

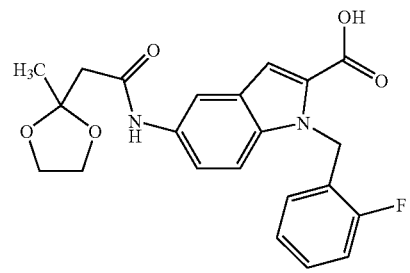

Preparation analogously to Example XXII using 234 mg (0.63 mmol) of ethyl 1-(2-fluorobenzyl)-5-{[(2-methyl-1,3-dioxolan-2-yl)acetyl]amino}-1H-indole-2-carboxylate from Example XXXVIII and 0.53 ml (1.06 mmol) of lithium hydroxide solution.

Yield: 198 mg (36% of theory)
LC/MS (method 1): $R_t$=4.00 min
MS (EI): m/z=413 (M+H)$^+$

Example XLI

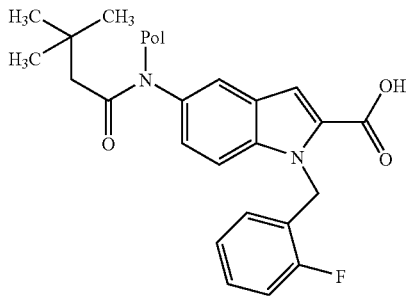

100 mg (0.08 mmol) of NovaCHO resin are initially charged in toluene/trimethyl orthoformate, and 130 mg (0.42 mmol) of ethyl 5-amino-1-(2-fluorobenzyl)-1H-indole-2-carboxylate from Example XXXVI are added. The mixture is shaken for 20 hours and then filtered off and washed with DMF. The resulting resin is initially charged in DMF, and 86 mg (0.33 mmol) of tetra-n-butylammonium borohydride are added. The mixture is shaken for 20 hours and then filtered off and washed with methanol, dichloromethane/acetic acid 10/1, methanol, dichloromethane/diethyl ether 10/1, methanol and dichloromethane.

To 1000 mg (0.85 mmol) of the resin described above, 30 ml of dichloromethane, 1.29 g (1.77 ml, 12.75 mmol) of triethylamine and 1.14 g (1.19 ml, 8.50 mmol) of dimethylbutyryl chloride are added. The mixture is then shaken for 20 hours, filtered off with suction and washed with DMF, methanol and dichloromethane.

To 1000 mg (2.61 mmol) of the resulting resin, 15 ml of dioxane and 7.5 ml of potassium hydroxide/methanol (100 mg/ml) are-added. The mixture is then shaken over the weekend, filtered off with suction and washed with DMF, 30% strength acetic acid, methanol and dichloromethane.

Example XLII

Di-(tert-butyl) 5-({{5-[(3,3-dimethylbutanoyl)amino]-1-(2-fluorobenzyl)-1H-indol-2-yl]carbonyl}amino)-2-pyridinylimidodicarbonate Di-(tert-butyl) 5-nitro-2-pyridinylimidodicarbonate: 5.0 g (35.94 mmol) of 2-amino-5-nitropyridine are dissolved in 200 ml of dichloromethane, and the mixture is cooled to 0° C. 9.29 g (12.52 ml, 71.88 mmol) of N,N-diisopropylethylamine, 19.61 g (89.86 mmol) of di-tert-butyl pyrocarbonate and 4.83 g (39.54 mmol) of 4-dimethylaminopyridine are added. The mixture is stirred at RT overnight and then diluted with ethyl acetate and washed three times with aqueous ammonium chloride solution, once with sat. sodium chloride solution, twice with aqueous sodium bicarbonate solution and once more with saturated sodium chloride solution. The organic phase is dried using sodium sulphate, filtered and concentrated under reduced pressure.

Yield: 10 g (82% of theory)

Di-(tert-butyl) 5-amino-2-pyridinylimidodicarbonate: 7.0 g (20.63 mmol) of di-(tert-butyl) 5-nitro-2-pyridinylimidodicarbonate are dissolved in 150 ml of ethanol and 50 ml of dichloromethane. The mixture is hydrogenated at atmospheric pressure. For work-up, the mixture is filtered through a Seitz filter and washed with THF. The filtrate is dried under reduced pressure.

Yield: 5.70 g (89% of theory)

Title Compound:

Under argon, 200 mg (0.52 mmol) of 5-[(3,3-dimethylbutanoyl)amino]-1-(2-fluorobenzyl)-1H-indole-2-carboxylic acid from Example XXXIX and 3.91 g (4 ml, 49.46 mmol) of pyridine are initially charged in 2 ml of DMF. 596 mg (1.57 mmol) of O-(7-azabenzotriazol-1-yl)-N,N,N',N'-tetramethyluronium hexafluorophosphate and 323 mg (1.05 mmol) of di-(tert-butyl) 5-amino-2-pyridinylimidodicarbonate are added. The mixture is stirred at RT overnight and the solvent is removed under reduced pressure. The residue is extracted with ethyl acetate and sat. sodium chloride solution. The organic phase is dried with sodium sulphate, filtered and dried under reduced pressure. The residue is purified by HPLC.

Yield: 111 mg (24% of theory)

LC/MS (method 2): $R_t$=4.30 min

MS (EI): m/z=672 (M−H)$^+$

The following compound is prepared analogously to the procedure described in Example XLII (amide coupling): with aqueous sodium bicarbonate solution and once more with saturated sodium chloride solution. The organic phase is dried using sodium sulphate, filtered and concentrated under reduce pressure.

Yield: 10 g (82% of theory)

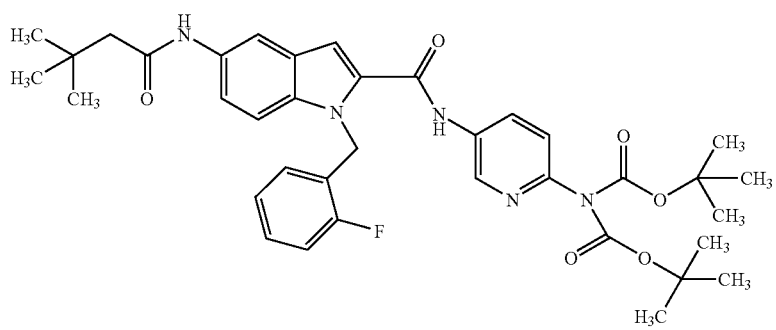

Di-(tert-butyl) 5-amino-2-pyridinylimidodicarbonate: 7.0 g (20.63 mmol) of di-(tert-butyl) 5-nitro-2-pyridinylimidicarbonate are dissolved in 150 ml of ethanol and 50 ml of dichloromethane. The mixture is hydrogenated at atmospheric pressure. For work-up, the mixture is filtrated through a Seitz filter and washed with THF. The filtrated is dried under reduced pressure.

Yield: 5.70 (89% of theory)

Title Compound: Under argon, 200 mg (052 mmol) of 5-[(3,3-dimethylbutanoyl)amino]1-(2-fluorobenzyl)-1H-indole-2 carboxylic acid from Example XXXIX and 3.91 g (4 ml, 49.46 mmol) of pyridine are initially charge in 2 ml of DMF. 596 mg (1.57 mmol) of O-(7azabenzotriazol-1-yl)-N,N,N',N'-tetramethyluronium hexafluorophosphate and 323 mg (1.05 mmol) of di-(tert-butyl) 5-amino-2pyridinylimidodicarbonate are added. The mixture is stirred at RT overnight and the solvent is removed under reduce pressure. The residue is extracted with ethyl acetate and sat. sodium chloride solution. The organic phase is dried with sodium sulphate, filtered and dried under reduce pressure. The residue is purified by HPLC.

Yield: 111 mg (24% of theory)
LC/MS (method 2): $R_t$=430 min
MS (EI): m/z=672 (M-H)$^+$ The following compound is prepared analogously to the procedure described in Example XLII (amide coupling):

Under argon, 400 mg (1.05 mmol) of 5-[(3,3-dimethylbutanoyl)amino]-1-(2-fluorobenzyl)-1H-indole-2-carboxylic acid from Example XXXIX are dissolved in 10 ml of DMF. The mixture is cooled to 0° C., and 202 mg (81.57 mmol) of N,N-diisopropylethylamine and 278 mg (1.26 mmol) of N,N-bis-(2-methoxyethyl)-N-(trifluoro-14-sulphanyl)amine are added. The mixture is stirred at this temperature for 15 minutes and immediately reacted further.

Half of the solution is cooled to 0° C., and 119 mg (0.86 mmol) of 5-nitro-2-pyridineamine are added. After 15 minutes, the mixture is allowed to warm to RT and stirred for another 24 hours. For work-up, the mixture is diluted with ethyl acetate and washed 3 times with aqueous sodium bicarbonate solution. The organic phase is washed once with sat. sodium chloride solution, dried with sodium sulphate, filtered and concentrated under reduced pressure using a rotary evaporator. The residue is purified by preparative HPLC.

Yield: 55 mg (25% of theory)
HPLC (method 1): $R_t$=5.20 min
MS (ESIpos): m/z=504 (M+H)$^+$

| Example | Structure | Analytical data |
|---|---|---|
| XLIII | 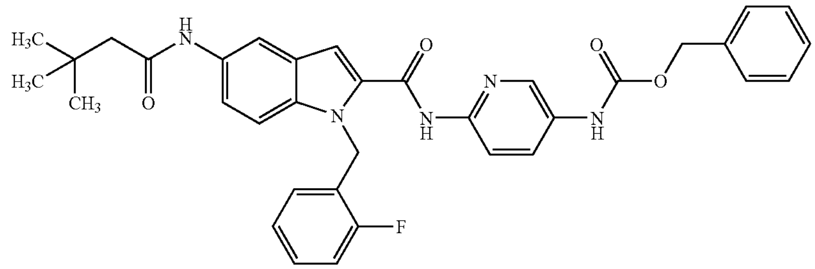 | HPLC(method 6):<br>$R_t$ = 4.97 min<br>MS(ESIpos): m/z = 608 (M + H)$^+$ |

Example XLIV

5-[(3,3-Dimethylbutanoyl)amino]-1-(2-fluorobenzyl)-N-(5-nitro-2-pyridinyl)-1H-indole-2-carboxamide

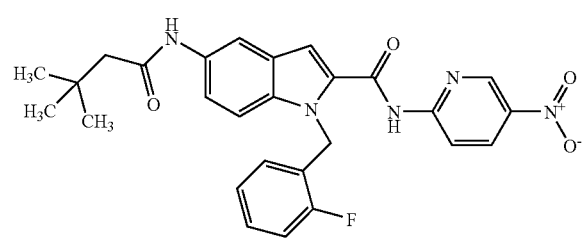

Example XLV tert-Butyl 4-({[5-[(3,3-dimethylbutanoyl)amino]-1-(2-fluorobenzyl)-1H-indol-2-yl]-carbonyl}amino)phenylcarbamate

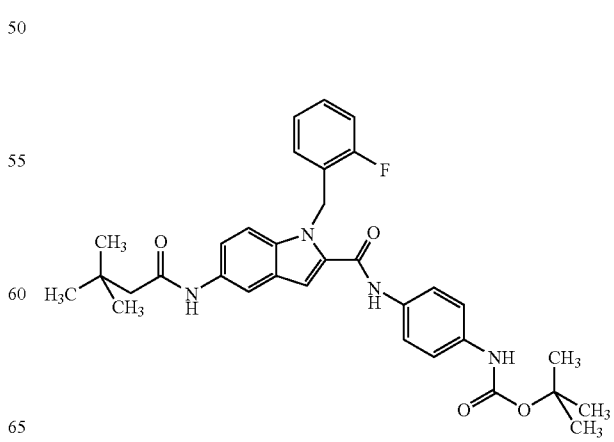

50 mg (0.13 mmol) of 5-[(3,3-dimethylbutanoyl)amino]-1-(2-fluorobenzyl)-1H-indole-2-carboxylic acid from Example XXXIX, 37.6 mg (0.20 mmol) of N'-(3-dimethylaminopropyl)-N-ethylcarbodiimide×HCl and 8 mg (0.07 mmol) of 4-dimethylaminopyridine are initially charged in DMF. 32.7 mg (0.16 mmol) of tert-butyl 4-aminophenylcarbamate are added, and the mixture is stirred at RT overnight. For work-up, the mixture is diluted and extracted with aqueous hydrochloric acid and dichloromethane. The organic phase is washed with sat. sodium chloride solution, dried with sodium sulphate, filtered and dried under reduced pressure.

Yield: 104 mg (82% of theory)
LC/MS (method 4): $R_t$=5.20 min
MS (EI): m/z=571 (M−H)$^+$ The following compound is prepared analogously to the procedure described in Example XLV:

| Example | Structure | Analytical data |
|---|---|---|
| XLVI | 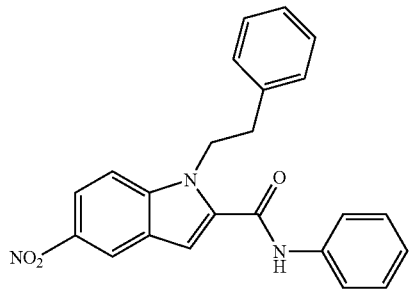 | HPLC(method 1):<br>$R_t$ = 5.09 min<br>MS(EI): m/z = 615<br>(M + H)$^+$ |

Example XLVII

5-Nitro-1H-indole-2-carboxylic acid

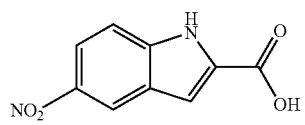

16.5 g (66.93 mmol) of ethyl 5-nitroindole-2-carboxylate are dissolved in 200 ml each of methanol and THF, and 67 ml (133.85 mmol) of lithium hydroxide solution are added. The mixture is heated at 90° C. for half an hour. After cooling, the mixture is, for work-up, diluted and extracted with aqueous hydrochloric acid and ethyl acetate. The organic phase is washed with sat. sodium chloride solution, dried with sodium sulphate, filtered and dried under reduced pressure.

Yield: 15 g (100% of theory)
LC/MS (method 4): $R_t$=3.18 min
MS (EI): m/z=205 (M−H)$^+$

Example XLVIII

5-Nitro-N-phenyl-1H-indole-2-carboxamide

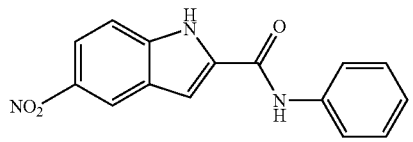

5.44 g (26.39 mmol) of 5-nitro-1H-indole-2-carboxylic acid from Example XLVII, 7.59 g (39.58 mmol) of N'-(3-dimethylaminopropyl)-N-ethylcarbodiimide×HCl and 1.61 g (13.19 mmol) of 4-dimethylaminopyridine are initially charged in 400 ml of a 10:1 dichloromethane:DMF mixture. 2.95 g (2.89 ml, 31.67 mmol) of aniline are added, and the mixture is stirred at RT overnight. For work-up, the mixture is diluted and extracted with aqueous hydrochloric acid and dichloromethane. The organic phase is washed with sat. sodium chloride solution, dried with sodium sulphate, filtered and dried under reduced pressure.

Yield: 5.83 g (75% of theory)
LC/MS (method 4): $R_t$=4.01 min
MS (EI): m/z=280 (M−H)$^+$

Example XLIX

5-Nitro-N-phenyl-1-(2-phenylethyl)-1H-indole-2-carboxamide

Under argon, 200 mg (0.71 mmol) of 5-nitro-N-phenyl-1H-indole-2-carboxamide from Example XLVIII are initially charged in 5 ml of dimethylformamide. 85.3 mg (2.13 mmol) of sodium hydroxide (60% dispersion in paraffin) are added a little at a time, and the mixture is stirred at RT for 30 min. 657 mg (3.56 mmol) of (2-bromoethyl)benzene are then added, and the mixture is stirred at 100° C. for another 5 h. To terminate the reaction, a further 3 eq. of sodium hydride and 5 eq. of bromide are added, and the mixture is stirred at 100° C. for 7 hours. The reaction mixture is poured into aqueous hydrochloric acid and extracted with ethyl acetate. The organic phase is dried over sodium sulphate and the solvent is removed using a rotary evaporator. The resulting crude product is purified by column chromatography (silica gel 60, mobile phase: cyclohexane/ethyl acetate 6:1).

Yield: 56 mg (20% of theory)
LC/MS (method 1): $R_t$=5.05 min
MS(EI): m/z=384 (M−H)$^+$ Example L tert-Butyl [2-(anilinecarbonyl)-5-nitro-1H-indol-1-yl]acetate

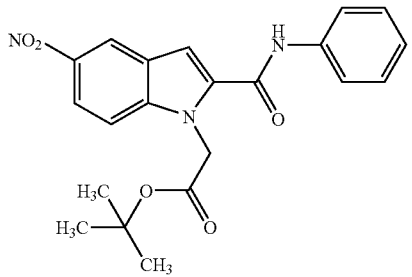

Under argon, 328 mg (1.24 mmol) of 1,4,7,10,13,16-hexaoxacyclooctadecane (18-crown-6) are initially charged in 61 ml of dichloromethane, and 15 ml (14.93 mmol) of a 1-molar potassium tert-butoxide solution in THF and 3.50 g (12.44 mmol) of 5-nitro-N-phenyl-1H-indole-2-carboxamide from Example XLVIII are added. The mixture is stirred at RT for 15 minutes and then cooled to 0° C. A solution of 3.64 g (18.67 mmol) of tert-butyl bromoacetate in 100 ml of THF is slowly added dropwise. The ice-bath is removed and the mixture is stirred at RT overnight. For work-up, the mixture is diluted with water and the THF is removed under reduced pressure using a rotary evaporator. The aqueous residue is extracted with ethyl acetate and the organic phase is washed with sat. sodium chloride solution, dried with sodium sulphate, filtered and dried under reduced pressure.

Yield: 4.35 g (69% of theory)
LC/MS (method 2):L $R_t$=3.90 min
MS (EI): m/z=418 (M+Na)$^+$ Example LI 5-Amino-N-phenyl-1-(2-phenylethyl)-1H-indole-2-carboxamide

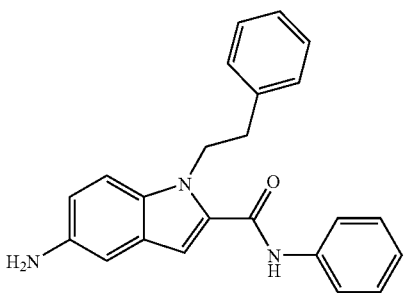

50 mg (0.13 mmol) of 5-nitro-N-phenyl-1-(2-phenylethyl)-1H-indole-2-carboxamide from Example XLIX are initially charged in 7 ml of ethyl acetate and 7 ml of ethanol. 49 mg (0.78 mmol) of ammonium formate and 14 mg of palladium on activated carbon are added. The mixture is heated to reflux, and at 50° C. gas evolves. After 4 hours at reflux, the mixture is cooled and filtered through kieselguhr, which is then washed with 500 ml of ethanol. The solvent is removed under reduced pressure and the residue is dried. This gives 115 mg of a white solid which still contains inorganic salts and which is reacted further without purification.

The following compound is prepared analogously to the procedure described in Example LI:

| Example | Structure | Analytical data |
|---|---|---|
| LII | ![structure] | LC/MS(method 4): $R_t$ = 2.60 min MS(EI): m/z = 366 (M + H)$^+$ |

Example LIII tert-Butyl {2-(anilinecarbonyl)-5-[(3,3-dimethylbutanoyl)amino]-1H-indol-1-yl}acetate

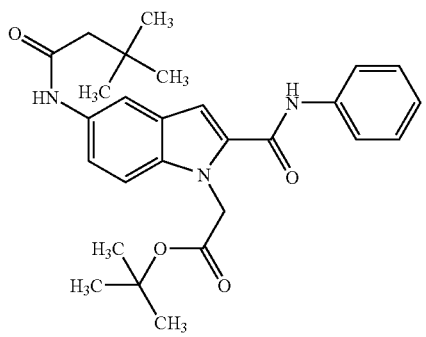

Under argon, 50 mg (0.14 mmol) of tert-butyl [5-amino-2-(anilinecarbonyl)-1H-indol-1-yl]acetate from Example LII and 15.23 mg (0.02 ml, 0.15 mmol) of triethylamine are added to 2 ml of THF. The mixture is cooled to 0° C., and a solution of 20.26 mg (0.02 ml, 0.15 mmol) of 3,3-dimethylbutyryl chloride in 0.2 ml of THF is added. The mixture is stirred at RT for 2 hours and, for work-up, added to dilute hydrochloric acid and ethyl acetate and extracted. The organic phase is washed with sat. sodium bicarbonate solution, dried with sodium sulphate, filtered and dried under reduced pressure. The resulting crude product is purified by column chromatography (silica gel 60, mobile phase: cyclohexane/ethyl acetate 2:1).

Yield: 80 mg (93% of theory)
LC/MS (method 1): $R_t$=4.78 min
MS (EI): m/z=464 (M+H)$^+$

Example LIV

{2-(Anilinecarbonyl)-5-[(3,3-dimethylbutanoyl)amino]-1H-indol-1-yl}acetic acid

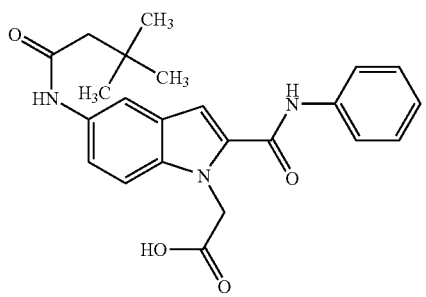

70 mg (0.15 mmol) of tert-butyl {2-(anilinecarbonyl)-5-[(3,3-dimethylbutanoyl)-amino]-1H-indol-1-yl}acetate from Example LIII, 0.50 ml of trifluoroacetic acid and 1 ml of dichloromethane are stirred together at RT for one hour. The solvent is removed under reduced pressure and the residue is dried in vacuo.

Yield: 86.7 mg (100% of theory)
LC/MS (method 1): $R_t$=4.43 min
MS (EI): m/z=408 (M+H)$^+$

Example LV

Ethyl {2-(anilinecarbonyl)-5-[(3,3-dimethylbutanoyl)amino]-1H-indol-1-yl}acetate

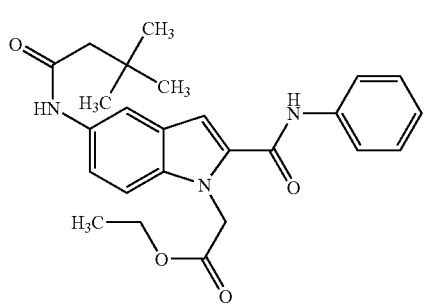

1.50 g (3.68 mmol) of {2-(anilinecarbonyl)-5-[(3,3-dimethylbutanoyl)amino]-1H-indol-1-yl}acetic acid from Example LIV, 225 mg (1.84 mmol) of 4-dimethylaminopyridine and 203.5 mg (4.42 mmol) of ethanol are initially charged in dichloromethane. The mixture is cooled to 0° C., and 776 mg (4.05 mmol) of N'-(3-dimethylaminopropyl)-N-ethylcarbodiimide×HCl are added. The mixture is stirred at RT for 4 hours. For work-up, the mixture is diluted and extracted with water and dichloromethane. The organic phase is dried with sodium sulphate, filtered and dried under reduced pressure. The resulting crude product is purified by column chromatography (silica gel 60, mobile phase: cyclohexane/ethyl acetate 2:1–1:1).

Yield: 227 mg (14% of theory)
LC/MS (method 4): $R_t$=4.60 min
MS (EI): m/z=436 (M+H)$^+$

Example LVI

Ethyl 5-nitro-1-phenyl-1H-indole-2-carboxylate

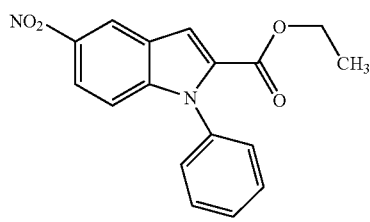

5.5 g (22.31 mmol) of ethyl 5-nitro-1H-indole-2-carboxylate, 6.16 g (44.62 mmol) of anhydrous potassium carbonate, 77.53 g (52 ml, 493.8 mmol) of bromobenzene and 1.6 g (11.15 mmol) of copper bromide are stirred under reflux (about 156° C.) for 5 days. The reaction mixture is then filtered, and the residue on the frit is washed with toluene. The collected filtrates are concentrated, dried under high vacuum and purified by flash chromatography on silica gel.

Yield: 5.71 g (82% of theory)
LC/MS (method 1): $R_t$=5.14 min
MS (EI): m/z=309 (M−H)$^+$

Example LVII

Ethyl 5-amino-1-phenyl-1H-indole-2-carboxylate

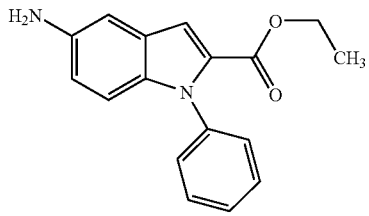

300 mg (0.97 mmol) of ethyl 5-nitro-1-phenyl-1H-indole-2-carboxylate from Example LVI are initially charged in 40 ml of ethyl acetate and 40 ml of ethanol. 365 mg (5.80 mmol) of ammonium formate and 102 mg of palladium on activated carbon (10%) are added. The mixture is heated to reflux, and at 50° C. gas evolves. After 4 hours at reflux, the mixture is cooled and filtered off through kieselguhr, which is washed with 500 ml of ethanol. The solvent is removed under reduced pressure and the residue is dried.

Yield: 355 mg (93% of theory)
LC/MS (method 5): $R_t$=2.17 min
MS (EI): m/z=281 (M+H)$^+$

Example LVIII

Ethyl 5-[(3,3-dimethylbutanoyl)amino]-1-phenyl-1H-indole-2-carboxylate

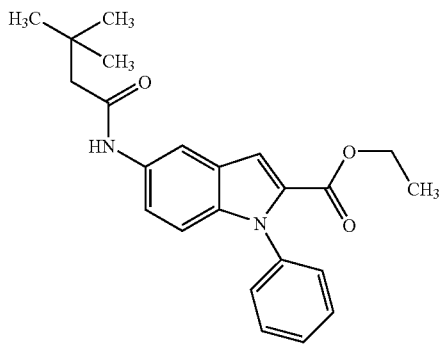

Under argon, 355 mg (1.27 mmol) of ethyl 5-amino-1-phenyl-1H-indole-2-carboxylate from Example LVII and 141 mg (0.19 ml, 1.39 mmol) of triethylamine are added to 4 ml of THF. The mixture is cooled to 0° C., and a solution of 170 mg (0.18 ml, 1.27 mmol) of 3,3-dimethylbutyryl chloride in 2 ml of THF is added. The mixture is stirred at RT for 2 hours. To bring the reaction to completion, a further 1 eq. of triethylamine and 1 eq. of acid chloride are added and the mixture is stirred at RT for 2 hours. For work-up, the mixture is added to dilute hydrochloric acid and ethyl acetate and extracted. The organic phase is washed with sat. sodium bicarbonate solution, dried with sodium sulphate, filtered and dried under reduced pressure. The resulting crude product is purified by column chromatography (silica gel 60, mobile phase: cyclohexane/ethyl acetate 3:1-1:1).

Yield: 118 mg (25% of theory)
LC/MS (method 5): $R_t$=3.54 min
MS (EI): m/z=379 (M+H)$^+$

Example LIX

5-[(3,3-Dimethylbutanoyl)amino]-1-phenyl-1H-indole-2-carboxylic acid

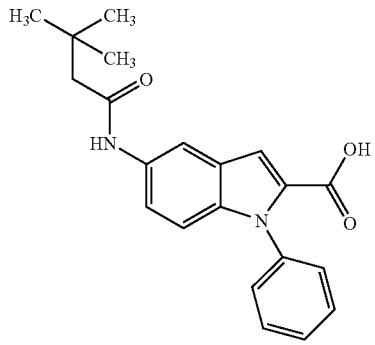

119 mg (0.31 mmol) of ethyl 5-[(3,3-dimethylbutanoyl)amino]-1-phenyl-1H-indole-2-carboxylate from Example LVIII are dissolved in each case in 2 ml of methanol and THF, and 0.31 ml (0.63 mmol) of a 2 M lithium hydroxide solution is added. The mixture is heated at 90° C. for one hour. After cooling, the mixture is, for work-up, diluted and extracted with aqueous hydrochloric acid and ethyl acetate. The organic phase is dried with sodium sulphate, filtered and dried under reduced pressure.

Yield: 151 mg (100% of theory)
$^1$H-NMR (200 MHz, DMSO-d$_6$): δ=1.03 (s, 9H), 2.18 (s, 2H), 6.96 (d, 1H), 7.31–7.40 (m, 3H), 7.46–7.59 (m, 4H), 8.15 (s, 1H), 9.77 (s, 1H), 12.73 (br. s, 1H).

Example LX tert-Butyl 4-[({5-[(3,3-dimethylbutanoyl)amino]-1-phenyl-1H-indol-2-yl}carbonyl)-amino]phenylcarbamate

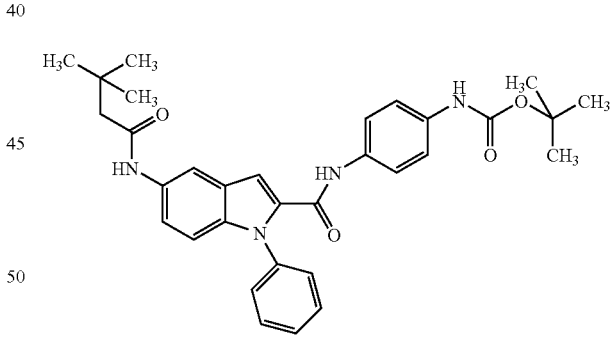

75 mg (0.21 mmol) of 5-[(3,3-dimethylbutanoyl)amino]-1-phenyl-1H-indole-2-carboxylic acid from Example LIX, 61.55 mg (0.32 mmol) of N'-(3-dimethylaminopropyl)-N-ethylcarbodiimide×HCl and 13.1 mg (0.11 mmol) of 4-dimethylaminopyridine are initially charged in 4 ml of dichloromethane. 44.6 mg (0.21 mmol) of tert-butyl 4-aminophenylcarbamate are added, and the mixture is stirred at RT for 3 hours. For work-up, the mixture is diluted and extracted with aqueous hydrochloric acid and dichloromethane. The organic phase is dried with sodium sulphate, filtered and dried under reduced pressure.

Yield: 87 mg (60% of theory)
LC/MS (method 4): $R_t$=5.02 min
MS (EI): m/z=539 (M−H)$^+$

Example LXI

Ethyl 5-amino-1H-indole-2-carboxylate

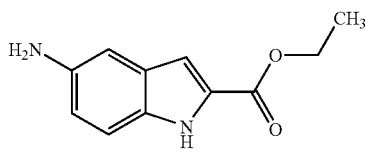

Under argon, 15 g (60.84 mmol) of ethyl 5-nitro-1H-indole-2-carboxylate are initially charged in 750 ml of ethyl acetate and 750 ml of ethanol. 15.82 g (15.82 mmol) of ammonium formate and 1.50 g of palladium on activated carbon (10%) are added. The mixture is stirred at 90° C. for 30 minutes and then cooled and filtered off through Celite, which is washed with ethyl acetate. The solvent is removed under reduced pressure and the residue is dissolved in chloroform and washed twice with water. The organic phase is dried with sodium sulphate, filtered and concentrated under reduced pressure using a rotary evaporator.

Yield: 12.81 g (100% of theory)
LC/MS (method 4): $R_t$=0.37 min
MS (EI): m/z=205 (M+H)$^+$
$^1$H-NMR (200 MHz, DMSO-$d_6$): δ=1.31 (t, 3H), 4.29 (q, 2H), 4.67 (s, 2H), 6.62–6.76 (m, 2H), 6.79–6.88 (m, 1H), 7.11–7.22 (m, 1H), 11.41 (br. s, 1H).

Example LXII

Ethyl 5-[(3,3-dimethylbutanoyl)amino]-1H-indole-2-carboxylate

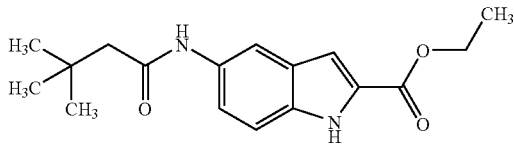

3.76 g (18.4 mmol) of ethyl 5-amino-1H-indole-2-carboxylate from Example LXI and 2.05 g (2.82 ml, 20.3 mmol) of triethylamine are added to 40 ml of THF. The mixture is cooled to 0° C., and a solution of 2.48 g (2.56 ml, 18.4 mmol) of 3,3-dimethylbutyryl chloride in 20 ml of THF are added. The mixture is stirred at RT for 2 h and, for work-up, poured into water. The pH is adjusted to 7 and the mixture is extracted 3 times with ethyl acetate. The combined organic phases are dried with sodium sulphate, filtered and dried under reduced pressure.

Yield: 5.49 g (98% of theory)
HPLC (method 4): $R_t$=4.20 min
MS (ESIpos): m/z=303 (M+H)$^+$

Example LXIII

Ethyl 5-[(3,3-dimethylbutanoyl)amino]-1-[2-(trifluoromethyl)benzyl]-1H-indole-2-carboxylate

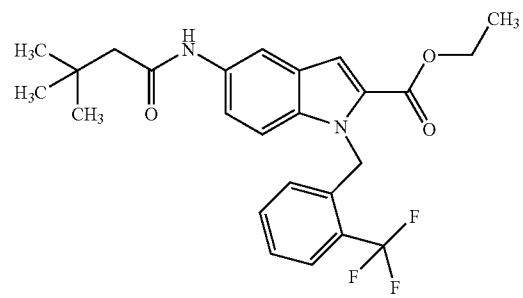

Under argon, 35 mg (0.13 mmol) of 1,4,7,10,13,16-hexaoxacyclooctadecane (18-crown-6) are initially charged in 7 ml of THF, and 1.98 ml (1.98 mmol) of a 1-molar potassium tert-butoxide solution in THF and 400 mg (1.32 mmol) of ethyl 5-[(3,3-dimethylbutanoyl)amino]-1H-indole-2-carboxylate from Example LXII are added. The mixture is stirred at RT for 15 minutes and cooled to 0° C. A solution of 474 mg (1.98 mmol) of 2-trifluoromethylbenzyl bromide in 12 ml of THF is slowly added dropwise. The ice-bath is removed and the mixture stirred at RT for 1 hour. For work-up, the mixture is diluted with water and the THF is removed under reduced pressure using a rotary evaporator. The aqueous residue is extracted with ethyl acetate and the organic phase is washed with sat. sodium chloride solution, dried with sodium sulphate, filtered and dried under reduced pressure. The residue is purified by column chromatography (mobile phase: cyclohexane:ethyl acetate 5:1).

Yield: 238 mg (39% of theory)
HPLC (method 5): $R_t$=360 min
MS (ESIpos): m/z=461 (M+H)$^+$ The following compounds are prepared analogously to the procedure described in Example LXIII:

| Example | Structure | Analytical data |
|---|---|---|
| LXIV | ![structure] | LC/MS(method 1): $R_t$ = 5.50 min<br>MS(EI): m/z = 399(M + H)$^+$ |

| Example | Structure | Analytical data |
|---|---|---|
| LXV | 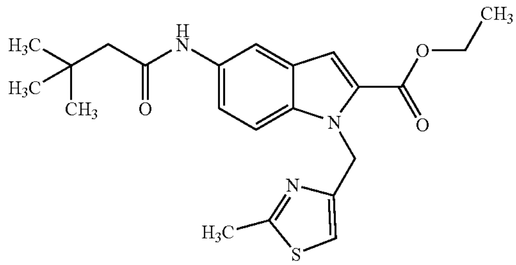 | LC/MS(method 2):<br>$R_t$ = 3.55 min<br>MS(EI): m/z = 414(M + H)$^+$ |
| LXVI | 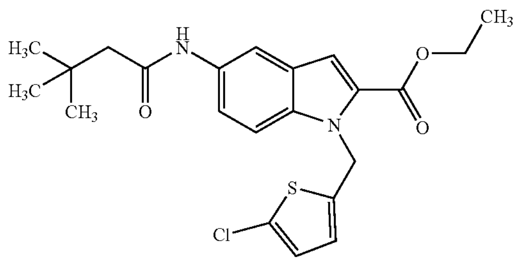 | LC/MS(method 2):<br>$R_t$ = 4.18 min<br>MS(EI): m/z = 433(M + H)$^+$ |

Example LXVII

5-[(3,3-Dimethylbutanoyl)amino]-1-[2-(trifluoromethyl)benzyl]-1H-indole-2-carboxylic acid

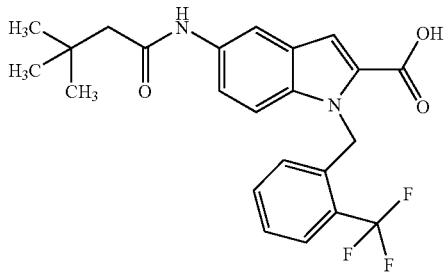

105 mg (0.26 mmol) of ethyl 5-[(3,3-dimethylbutanoyl)amino]-1-[2-(trifluoromethyl)benzyl]-1H-indole-2-carboxylate from Example LXIII are dissolved in 1 ml each of methanol and THF, and 0.26 ml (0.52 mmol) of 2M lithium hydroxide solution is added. The mixture is heated at 90° C. for one hour. After cooling, the mixture is, for work-up, diluted and extracted with aqueous hydrochloric acid and ethyl acetate. The organic phase is dried with sodium sulphate, filtered and dried under reduced pressure.

Yield: 89 mg (89% of theory)
HPLC (method 4): $R_t$=4.76 min
MS (ESIpos): m/z=433 (M+H)$^+$ The following compounds are prepared analogously to the procedure described in Example LXVII

| Example | Structure | Analytical data |
|---|---|---|
| LXVIII | 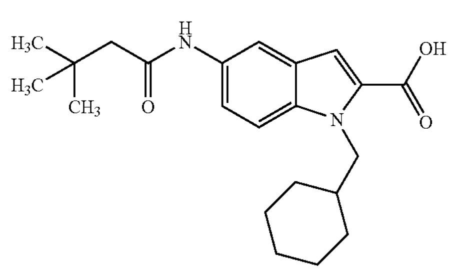 | LC/MS(method 1):<br>$R_t$ = 5.80 min<br>MS(EI): m/z = 371(M + H)$^+$ |

| Example | Structure | Analytical data |
|---|---|---|
| LXIX | 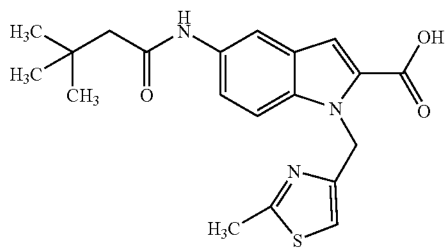 | LC/MS(method 4):<br>R_t = 3.95 min<br>MS(EI): m/z = 386(M + H)+ |
| LXX | 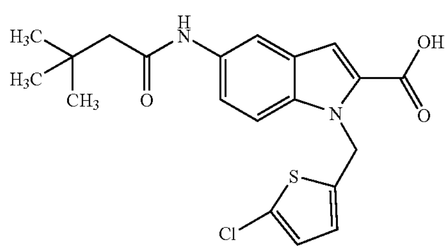 | ¹H-NMR(200 MHz, DMSO-d_6): δ = 1.05(s, 9H), 2.19(s, 2H), 5.89(s, 2H), 5.95(s, 2H), 6.98(d, 2H), 7.03(d, 1H), 7.22(s, 1H), 7.39(dd, 1H), 7.68(d, 1H), 8.06(dd, 1H), 9.78(s, 1H). |

Example LXXI tert-Butyl 4-[({5-[(3,3-dimethylbutanoyl)amino]-1-[2-trifluoromethyl)benzyl]-1H-indol-2-yl}carbonyl)amino]phenylcarbamate

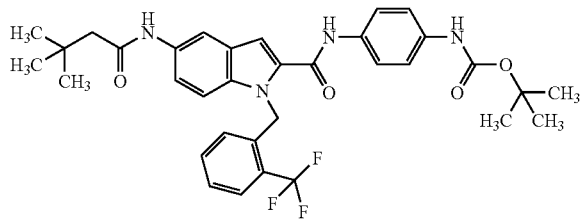

125 mg (0.29 mmol) of 5-[(3,3-dimethylbutanoyl)amino]-1-[2-(trifluoromethyl)-benzyl]-1H-indole-2-carboxylic acid from Example LXVII, 83 mg (0.43 mmol) of N'-(3-dimethylaminopropyl)-N-ethylcarbodiimide×HCl and 17.7 mg (0.14 mmol) of 4-dimethylaminopyridine are initially charged in 6 ml of dichloromethane. 60 mg (0.29 mmol) of tert-butyl 4-aminophenylcarbamate are added, and the mixture is stirred at RT for 4 hours. For work-up, the mixture is diluted and extracted with aqueous hydrochloric acid and ethyl acetate. The organic phase is washed with sat. sodium chloride solution, dried with sodium sulphate, filtered and dried under reduced pressure.

Yield: 158 mg (87% of theory)

LC/MS (method 1): R_t=5.40 min

MS (EI): m/z=645 (M+Na)+

The following compounds are prepared analogously to the procedure described in Example LXXI:

| Example | Structure | Analytical data |
|---|---|---|
| LXXII | 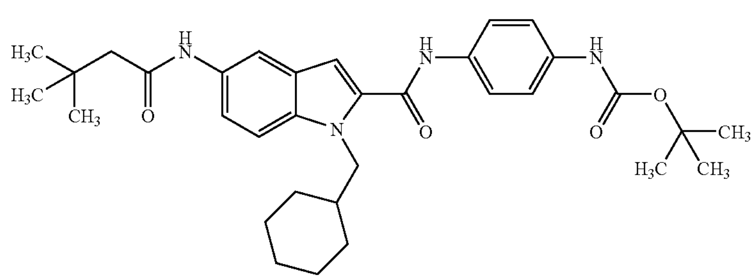 | LC/MS(method 1):<br>R_t = 5.50 min<br>MS(EI): m/z = 561(M + H)+ |

| Example | Structure | Analytical data |
|---|---|---|
| LXXIII | 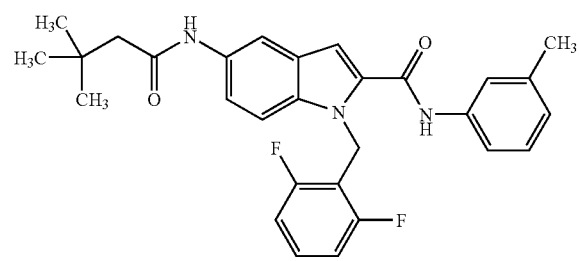 | LC/MS(method 1):<br>R$_t$ = 5.40 min<br>MS(EI): m/z =<br>595(M + H)$^+$ |

PREPARATION EXAMPLES

Example 1

1-(2,6-Difluorobenzyl)-5-[(3,3-dimethylbutanoyl) amino]-N-(3-methylphenyl)-1H-indole-2-carboxamide 59 mg (0.150 mmol) of the compound from Example XIV and 0.04 ml (0.30 mmol) of triethylamine are initially-charged in 5 ml of dichloromethane. At 0° C., a solution of 26 mg of 3,3-dimethylbutyryl chloride (0.195 mmol) in 1 ml of dichloromethane is added dropwise, and the mixture is stirred at RT for 30 min. The reaction solution is concentrated and the residue is purified chromatographically on silica gel 60 (mobile phase gradient cyclohexane→cyclohexane:ethyl acetate 2.5:1). The resulting product is taken up in a little ethyl acetate, precipitated by addition of n-pentane, filtered off with suction and dried. This gives 35 mg (45% of theory) of a light-beige solid.

MS (ESIpos): m/z=490 (M+H)$^+$ $^1$H-NMR (300 MHz, DMSO-d$_6$): δ=10.23 (s, 1H), 9.68 (s, 1H), 8.01 (d, 1H), 7.62 (s, 1H), 7.55 (d, 1H), 7.45–7.29 (m, 3H), 7.23 (t, 1H), 7.19 (s, 1H), 7.03 (t, 2H), 6.92 (d, 1H), 5.96 (s, 2H), 2.32 (s, 3H), 2.18 (s, 2H), 1.03 (s, 9H).

The examples below are prepared in a manner analogous to Example 1 using the appropriate starting materials:

Example 2

1-(2,6-Difluorobenzyl)-5-[(3,3-dimethylbutanoyl) amino]-N-phenyl-1H-indole-2-carboxamide

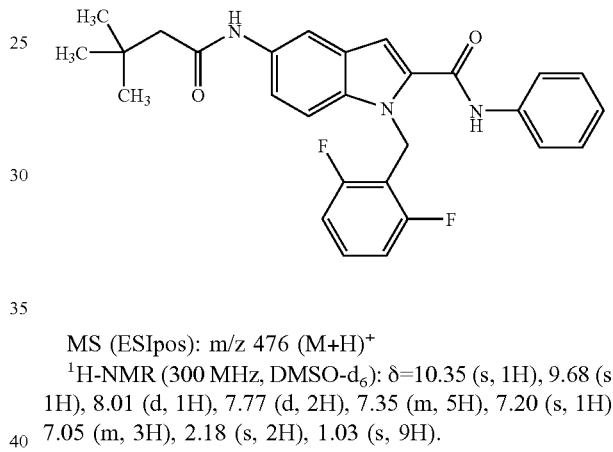

MS (ESIpos): m/z 476 (M+H)$^+$ $^1$H-NMR (300 MHz, DMSO-d$_6$): δ=10.35 (s, 1H), 9.68 (s, 1H), 8.01 (d, 1H), 7.77 (d, 2H), 7.35 (m, 5H), 7.20 (s, 1H), 7.05 (m, 3H), 2.18 (s, 2H), 1.03 (s, 9H).

Example 3

5-[(3,3-Dimethylbutanoyl)amino]-1-(2-fluorobenzyl)-N-(3-pyridinyl)-1H-indole-2-carboxamide

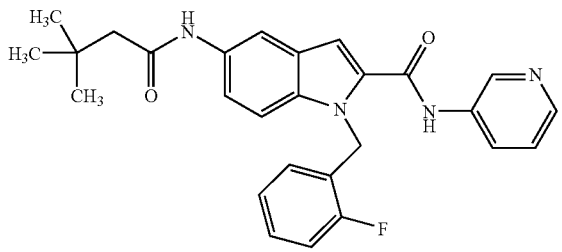

MS (ESIpos): m/z=459 (M+H)$^+$ $^1$H-NMR (200 MHz, DMSO-d$_6$): δ=10.57 (s, 1H), 9.77 (s, 1H), 8.88 (d, 1H), 8.30 (d, 1H), 8.20–8.09 (m, 2H), 7.53–7.12 (m, 6H), 7.01 (dt, 1H), 6.60 (t, 1H), 5.90 (s, 2H), 2.19 (s, 2H), 1.04 (s, 9H).

Example 4

5-[(3,3-Dimethylbutanoyl)amino]-1-(2-fluorobenzyl)-N-(3-methoxyphenyl)-1H-indole-2-carboxamide

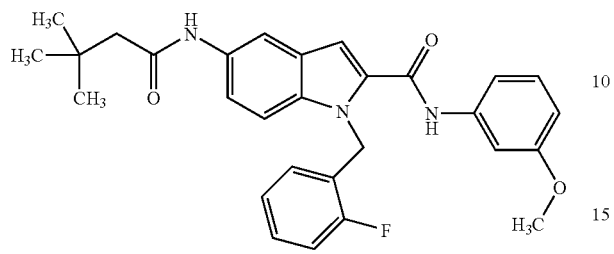

MS (ESIpos): m/z=488 (M+H)$^+$ $^1$H-NMR (300 MHz, DMSO-d$_6$): δ=10.30 (s, 1H), 9.71 (s, 1H), 8.08 (d, 1H), 7.48–7.14 (m, 8H), 7.00 (dt, 1H), 6.67 (ddd, 1H), 6.61 (dt, 1H), 5.89 (s, 2H), 3.74 (s, 3H), 2.19 (s, 2H), 1.04 (s, 9H).

Example 5

5-[(3,3-Dimethylbutanoyl)amino]-1-(2-fluorobenzyl)-N-(4-methoxyphenyl)-1H-indole-2-carboxamide

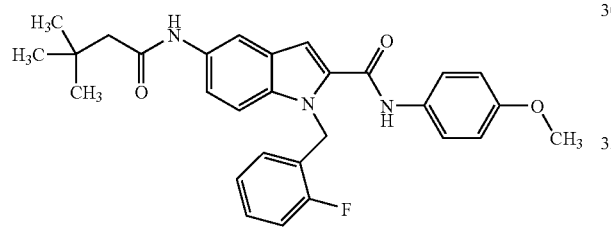

MS (ESIpos): m/z=488 (M+H)$^+$ $^1$H-NMR (300 MHz, DMSO-d$_6$): δ=10.21 (s, 1H), 9.70 (s, 1H), 8.07 (d, 1H), 7.61 (m, 2H), 7.43 (d, 1H), 7.33 (m, 2H), 7.21 (m, 2H), 7.00 (dt, 1H), 6.90 (m, 2H), 6.60 (dt, 1H), 5.89 (s, 2H), 3.74 (s, 3H), 2.19 (s, 2H), 1.04 (s, 9H).

Example 6

5-[(3,3-Dimethylbutanoyl)amino]-1-(2-fluorobenzyl)-N-(3-methylphenyl)-1H-indole-2-carboxamide

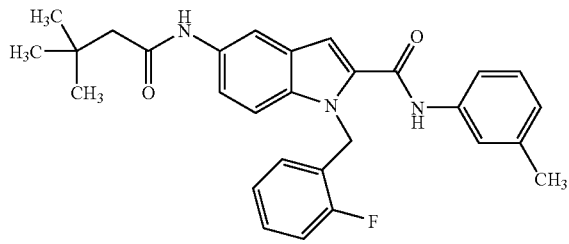

MS (ESIpos): m/z=472 (M+H)$^+$ $^1$H-NMR (300 MHz, DMSOd$_6$): s=10.24 (s, 1H), 9.70 (s, 1H), 8.08 (d, 1H), 7.58 (m, 1H), 7.50 (d, 1H), 7.44 (d, 1H), 7.38–7.14 (m, 5H), 7.00 (dt, 1H), 6.91 (d, 1), 6.60 (dt, 1H), 5.89 (s, 2H), 2.30 (s, 3H), 2.19 (s, 2H), 1.04 (s, 9H).

Example 7

5-[(3,3-Dimethylbutanoyl)amino]-1-(2-fluorobenzyl)-N-phenyl-1H-indole-2-carboxamide

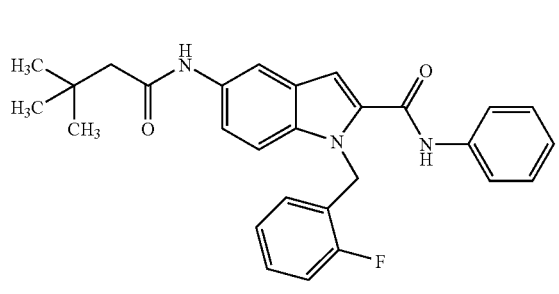

MS (ESIpos): m/z=458 (M+H)$^+$ $^1$H-NMR (300 MHz, DMSO-d$_6$): δ=10.31 (s, 1H), 9.71 (s, 1H), 8.08 (s, 1H), 7.77 (d, 2H), 7.47–7.14 (m, 7H), 7.09 (t, 1H), 7.00 (t, 1H), 6.61 (t, 1H), 5.90 (s, 2), 2.19 (s, 2H), 1.04 (s, 9H).

Example 8

5-[(Bicyclo[2.2.1]hept-2-ylacetyl)amino]-N-phenyl-1-propyl-1H-indole-2-carboxamide

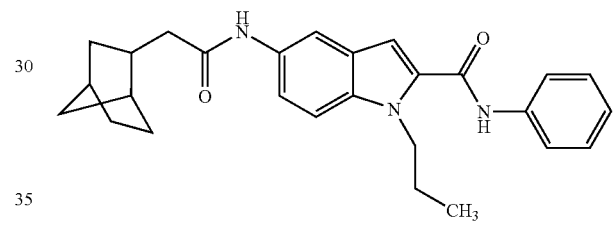

MS (ESIpos): m/z=430 (M+H)$^+$ $^1$H-NMR (300 MHz, DMSO-d$_6$): δ=10.25 (s, 1H), 9.75 (s, 1H), 8.03 (s, 1H), 7.7 (d, 2H), 7.52 (d, 1H), 7.42–7.30 (m, 3H), 7.23 (s, 1H), 7.10 (dd, 1H), 4.50 (t, 2H), 2.40–2.09 (m, 5H), 1.84–1.06 (m, 1H), 0.81 (t, 3H), 0.73 (m, 1H).

Example 9

5-[(Cyclohexylcarbonyl)amino]-1-(2-fluorobenzyl)-N-phenyl-1H-indole-2-carboxamide

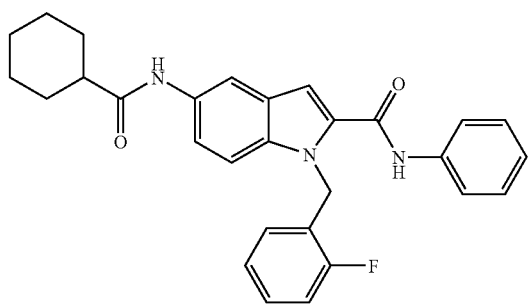

MS (ESIpos): m/z=470 (M+H)$^+$ $^1$H-NMR (300 MHz, DMSO-d$_6$): δ=10.32 (s, 1H), 9.71 (s, 1H), 8.11 (d, 1H), 7.72 (d, 2H), 7.47–7.13 (m, 7H), 7.08 (t, 1H), 6.98 (dt, 1H), 6.59 (dt, 1H), 5.90 (s,2H), 2.33 (m, 1H), 1.88–1.60 (m, 5H), 1.52–1.15 (m, 5H).

The examples listed in the table below can be prepared analogously to the procedure described above using the appropriate starting materials.

| Example | Structure | Analytical data |
|---|---|---|
| 10 | 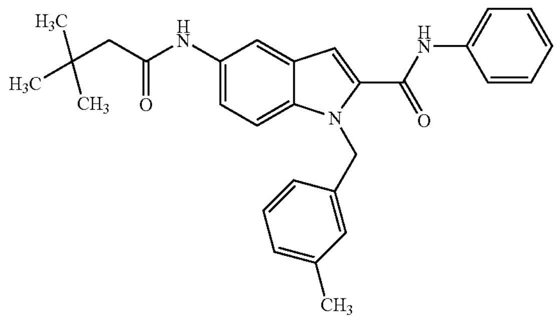 | LC-MS(method MHZ2Q):<br>R$_t$ = 4.93 min<br>m/z = 454(M + H)$^+$ |
| 11 | 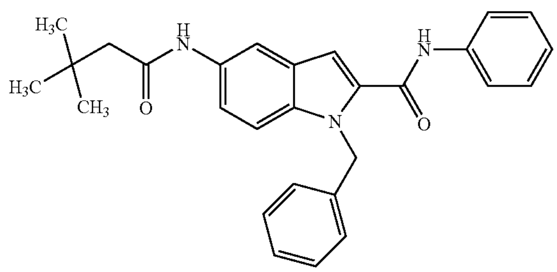 | |
| 12 | 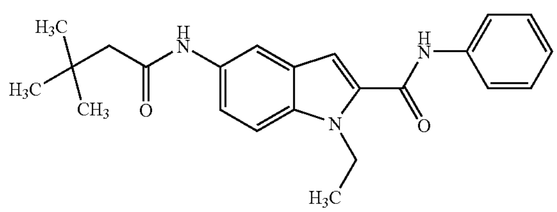 | LC-MS(method MHZ2Q):<br>R$_t$ = 4.51 min<br>m/z = 378(M + H)$^+$ |
| 13 | 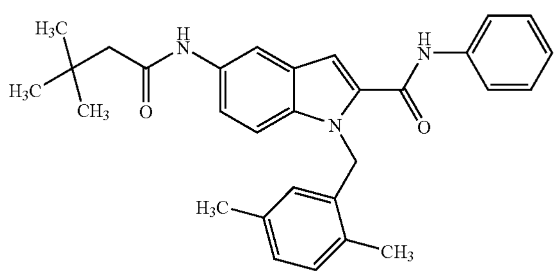 | |
| 14 | 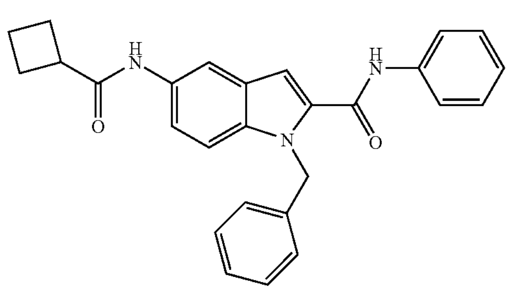 | |

-continued

| Example | Structure | Analytical data |
|---|---|---|
| 15 | 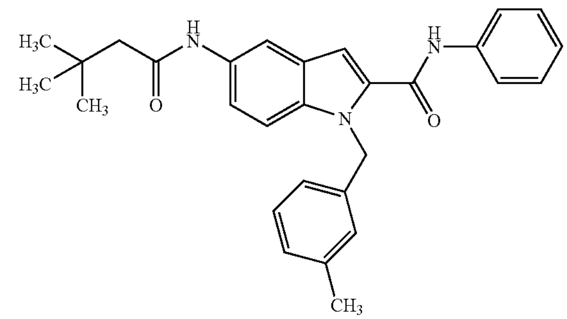 | |
| 16 | 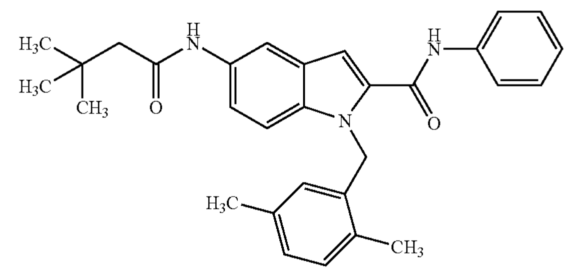 | |
| 17 | 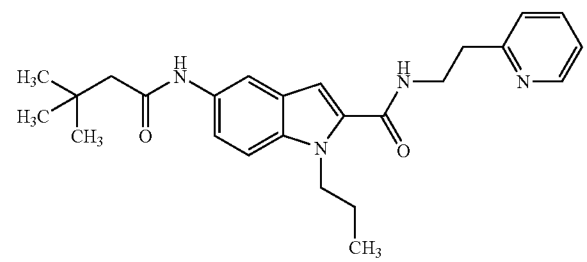 | LC-MS(method MHZ2Q):<br>$R_t$ = 2.96 min<br>m/z = 421(M + H)$^+$ |
| 18 | 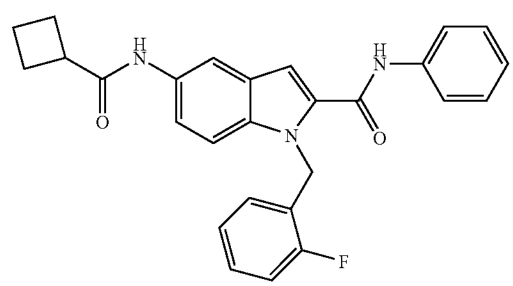 | |
| 19 | 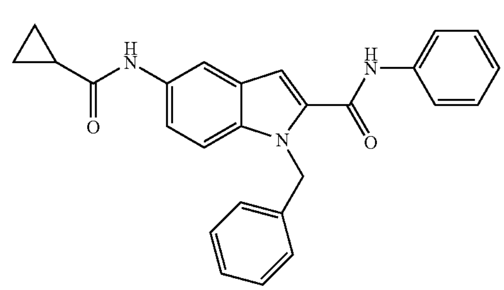 | LC-MS(method MHZ2Q):<br>$R_t$ = 4.42 min<br>m/z = 410(M + H)$^+$ |

| Example | Structure | Analytical data |
|---|---|---|
| 20 | 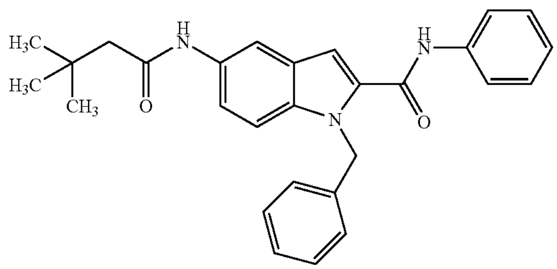 | LC-MS(method MHZ2Q): R$_t$ = 4.79 min m/z = 440(M + H)$^+$ |
| 21 | 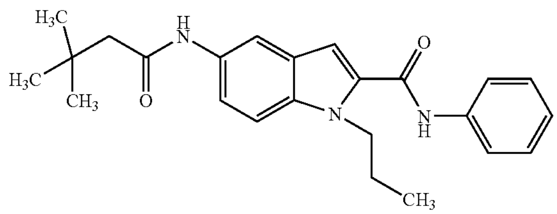 | MS(ESIpos): m/z = 392(M + H)$^+$. $^1$H-NMR(200 MHz, DMSO-d$_6$): δ = 10.30(s, 1H), 9.71 (s, 1H), 8.07(s, 1H), 7.78(d, 2H), 7.51(d, 1H), 7.33(m, 3H), 7.21(s, 1H), 7.09(dd, 1H), 4.50(t, 2H), 2.19(s, 2H), 1.70(sextet, 2H), 1.04 (s, 9H), 0.80(t, 3H). |
| 22 | 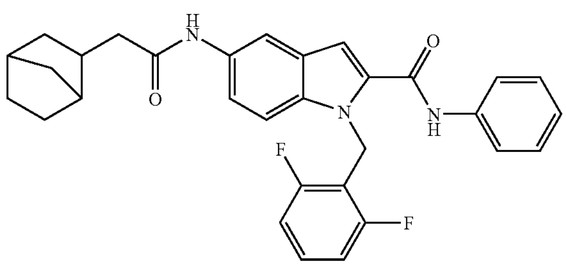 | MS(ESIpos): m/z = 514 (M + H)$^+$. $^1$H-NMR(200 MHz, DMSO-d$_6$): δ = 10.39(s, 1H), 9.81 (s, 1H), 8.03(d, 1H), 7.75(d, 2H), 7.51–6.95(m, 6H), 6.58 (t, 1H), 5.92(s, 2H), 2.45–2.05(m, 5H), 1.80–1.00(m, 8H), 0.71(m, 1H). |
| 23 | 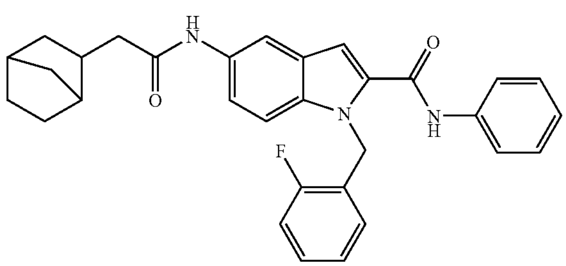 | MS(ESIpos): m/z = 496 (M + H)$^+$. $^1$H-NMR(200 MHz, CDCl$_3$): δ = 8.08(s, 1H), 7.92(s, 1H), 7.61(d, 2H), 7.48–6.85(m, 7H), 6.72(t, 1H), 5.89(s, 2H), 2.49–2.11 (m, 5H), 1.68–1.05(m, 8H), 0.73(m, 1H). |
| 24 | 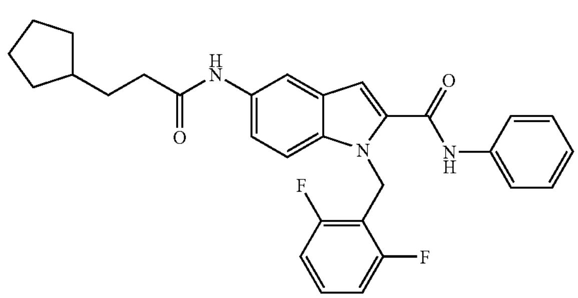 | MS(ESIpos): m/z = 502 (M + H)$^+$. $^1$H-NMR(200 MHz, DMSO-d$_6$): δ =10.39(s, 1H), 9.80 (s, 1H), 8.02(s, 1H), 7.77(d, 2H), 7.49–7.22(m, 5H), 7.21–6.91(m, 4H), 5.94(s, 2H), 2.29(t, 2H), 1.88–1.35 (m, 8H), 1.30–0.97(m, 2H). |

| Example | Structure | Analytical data |
|---|---|---|
| 25 | 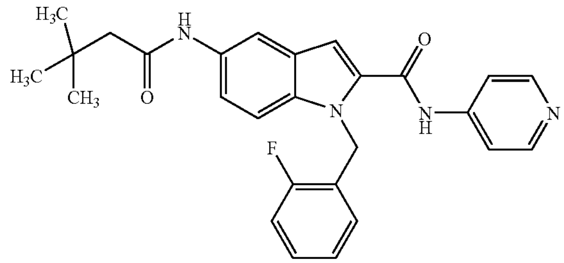 | HPLC(SYA-HPPSK2): R$_t$ = 4.43 min MS(ESIpos): m/z = 459.1(M + H)$^+$. $^1$H-NMR(200 MHz, DMSO-d$_6$): δ = 1.04(s, 9H), 2.19(s, 2H), 5.89(s, 2H), 6.59(t, 1H), 7.01(t, 1H), 7.15–7.54 (m, 5H), 7.73(d, 2H), 8.12 (s, 1H), 8.45(d, 2H), 9.78(s, 1H), 10.69(s, 1H). |

Example 26

1-(2-Fluorobenzyl)-5-{[(1-methylcyclopentyl)acetyl]amino}-N-phenyl-1H-indole-2-carboxamide

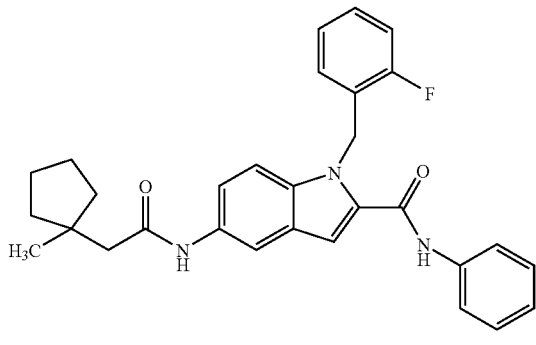

62 mg (0.20 mmol) of the compound from Example XXVI, 58 mg (0.30 mmol) of N'-(3-dimethylaminopropyl)-N-ethylcarbodiimide×HCl and 12 mg (0.1 mmol) of 4-dimethylaminopyridine are initially charged in DMF. 34 mg (0.24 mmol) of (1-methylcyclopentyl)acetic acid (synthesized according to K. Bott, Chem. Ber. 1967, 106, 978–983) are added, and the mixture is stirred at RT for 5 h. For work-up, the mixture is diluted and extracted with aqueous hydrochloric acid and dichloromethane. The organic phase is washed with sat. sodium chloride solution, dried with sodium sulphate, filtered and dried under reduced pressure. Purification is carried out by flash chromatography on silica gel.

Yield: 56 mg (57% of theory)

LC/MS (SMKL-ZQ-2A): R$_t$=4.15 min.

MS (ESIpos): m/z=484.1 (M+H)$^+$ $^1$H-NMR (200 MHz, DMSO-d$_6$): δ=1.05 (s, 3H), 1.63 (s, 8H), 2.29 (s, 2H), 5.90 (s, 2H), 6.60 (t, 1H), 6.91–7.39 (m, 9H), 7.44 (d, 1H), 7.72 (d, 2H), 8.10 (s, 9.79 (s, 1H), 10.37 (s, 1H).

The following compounds are prepared analogously to the procedure described in Example 26 using the appropriate starting materials:

| Example | Structure | Analytical data |
|---|---|---|
| 27 | 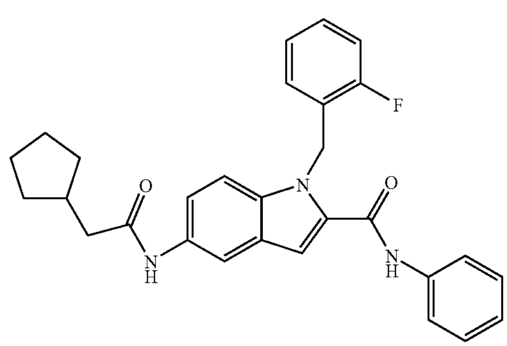 | LC/MS(method 2): R$_t$ = 3.90 min. MS(ESIpos): m/z = 470 (M + H)$^+$. $^1$H-NMR(400 MHz, DMSO-d$_6$): δ = 1.20(m, 2H), 1.52 (m, 2H), 1.59, (m, 2H), 1.77 (m, 2H), 2.20–2.37(m, 3H), 5.90(s, 2H), 6.59(t, 1H), 7.00(t, 1H), 7.09(t, 1H), 7.19(t, 1H), 7.25(q, 1H), 7.29–7.39(m, 4H), 7.45(d, 1H), 7.72(d, 2H), 8.10(s, 1H), 9.80(s, 1H), 10.34(s, 1H). |

| Example | Structure | Analytical data |
|---|---|---|
| 28 | 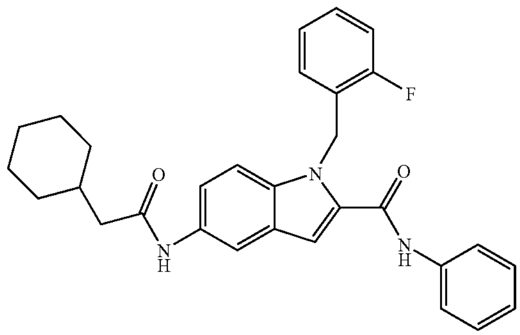 | LC/MS(method 2): R$_t$ = 4.07 min.<br>MS(ESIpos): m/z = 484 (M + H)$^+$.<br>$^1$H-NMR(400 MHz, DMSO-d$_6$): δ = 0.98(q, 2H), 1.11–1.31(m, 3H), 1.69(m, 6H), 2.18(d, 2H), 5.90(s, 2H), 6.59(t, 1H), 7.00(t, 1H), 7.09(t, 1H), 7.19(t, 1H), 7.25(q, 1H), 7.29–7.39(m, 4H), 7.45(d, 1H), 7.72(d, 2H), 8.10(s, 1H), 9.80(s, 1H), 10.34(s, 1H). |
| 29 | 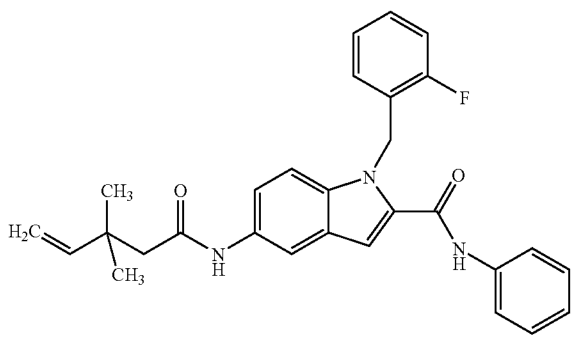 | LC/MS(SMKL-ZQ-2A): R$_t$ = 3.95 min.<br>MS(ESIpos): m/z = 470.2 (M + H)$^+$.<br>$^1$H-NMR(400 MHz, DMSO-d$_6$): δ = 1.14(s, 6H), 2.29(s, 2H), 4.94(dd, 2H), 5.90(s, 2H), 5.99(dd, 1H), 6.60(t, 1H), 7.00(t, 1H, 7.09(t, 1H), 7.21(dt, 2H), 7.33(t, 3H), 7.37(s, 1H), 7.45(d, 1H), 7.72(d, 2H0, 8.07(s, 1H), 9.74(s, 1H), 10.35(s, 1H). |
| 30 | 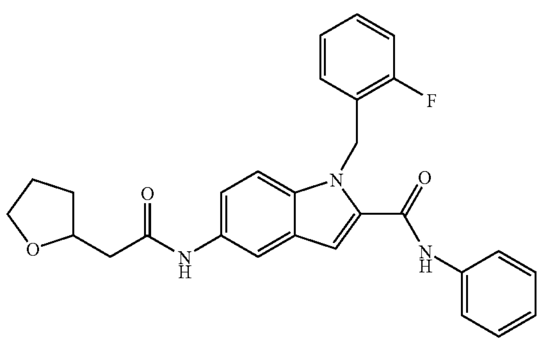 | LC/MS(SMKL-ZQ-2A): R$_t$ = 3.48 min.<br>MS(ESIpos): m/z = 472.1 (M + H)$^+$.<br>$^1$H-NMR(200 MHz, DMSO-d$_6$): δ = 1.49–1.65(m, 1H), 1.88(t, 2H), 1.92–2.10(m, 1H), 3.60(q, 1H), 3.78(q, 1H), 4.19(quintet, 1H), 5.90 (s, 2H), 6.59(t, 1H), 7.02(dt, 2H), 7.22–7.53(m, 9H), 7.73 (d, 2H), 8.11(d, 1H), 9.88(s, 1H), 10.37(s, 1H). |
| 31 | 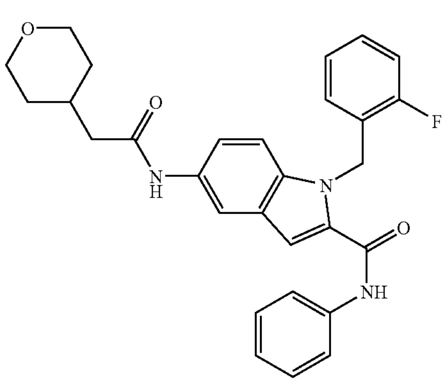 | LC/MS(SMKL-ZQ-2A): R$_t$ = 3.42 min.<br>MS(ESIpos): m/z = 486.1 (M + H)$^+$.<br>$^1$H-NMR(200 MHz, DMSO-d$_6$): δ = 1.19–1.28(dd, 2H), 1.61(d, 2H), 1.99(s, 1H), 2.25(d, 2H), 3.25(s, 2H), 3.83(d, 2H), 5.90(s, 2H), 6.59(t, 1H), 6.97(dt, 3H), 7.12–7.53(m, 9H), 7.72(d, 2H), 8.10(d, 1H), 9.87(s, 1H), 10.36(s, 1H). |

| Example | Structure | Analytical data |
|---|---|---|
| 32 | 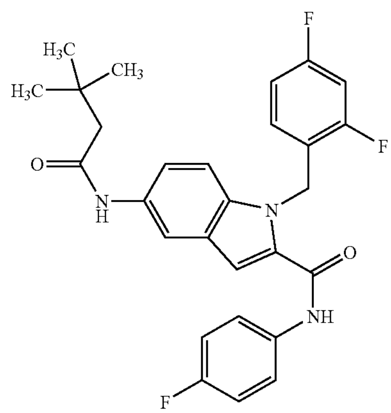 | $^1$H-NMR(200 MHz, DMSO-$d_6$): δ = 1.04(s, 9H), 2.19(s, 2H), 5.85(s, 2H), 6.70(q, 12H), 6.94(dt, 1H), 7.10–7.28(m, 3H), 7.28–7.42(m, 2H), 7.48(d, 1H), 7.75(dd, 2H), 8.09(s, 1H), 9.76(s, 1H), 10.43(s, 1H). |

Example 33

1-(2-Fluorobenzyl)-5-[(5-hydroxy-3,3-dimethylpentyl)amino]-N-phenyl-1H-indole-2-carboxamide

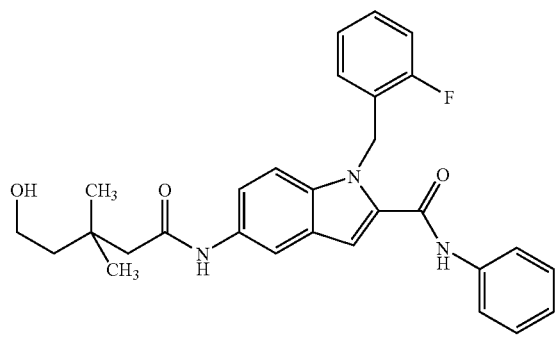

60 mg (0.13 mmol) of the compound from Example 29 are dissolved in 2 ml of THF and cooled to 0° C. Over a period of 3.5 hours, a total of 0.93 ml (0.46 mmol) of a 0.5-molar 9-borabicyclo[3.3.1]nonane solution in THF is added a little at a time to this solution, and during the addition, the temperature is allowed to warm to RT. The reaction mixture is stirred at RT for a further hour and then, at 0° C., 0.5 ml each of sodium carbonate solution and hydrogen peroxide solution are added slowly. After the exothermic reaction has ended, the mixture is stirred at RT for another 30 min. The reaction mixture is then diluted with ethyl acetate and extracted with dist. water and saturated sodium chloride solution. The organic phase is dried over sodium sulphate and filtered and the solvent is removed under reduced pressure. The residue is purified chromatographically on silica gel (mobile phase: cyclohexane/ethyl acetate 5:1 to 1:1). This gives 53 mg (85% of theory) of the product.

LC/MS (MHZ2P01): $R_t$=4.63 min.

MS (ESIpos): m/z=488.2 (M+H)$^+$.

The preparation of the following compounds is carried out analogously to the procedure described in Example XXXV:

| Example | Structure | Analytical data |
|---|---|---|
| 34 | ClH | LC/MS(method 2): $R_t$ = 2.25 min MS(EI): m/z = 487(M + H − HCl)$^+$ |

US 7,045,544 B2

| Example | Structure | Analytical data |
|---|---|---|
| 35 | 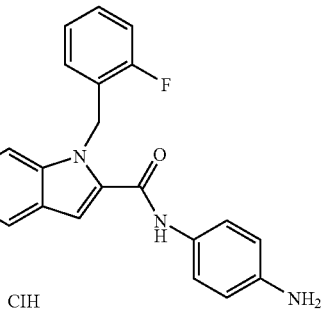 | LC/MS(SMKL-ZQ-2A-CC): R$_t$ = 2.84 min. MS(ESIpos): m/z = 485.4 (M + H)$^+$. $^1$H-NMR(400 MHz, DMSO-d$_6$): δ = 1.14(s, 6H), 2.30(s, 2H), 4.87–5.02(m, 3H), 5.89 (s, 2H), 5.95(s, 2H), 6.60(dt, 2H), 7.01(q, 2H), 7.13(br s, 1H), 7.34(t, 1H), 7.41(s, 1H), 7.46(d, 1H), 7.53(s, 1H), 7.69(d, 1H), 8.10(s, 1H), 9.78(s, 1H), 10.51(s, 1H), 10.63(s, 1H). |
| 36 | 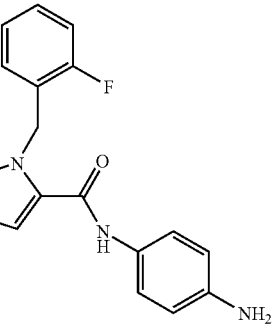 | LC/MS(SMKL-ZQ-2A-CC): R$_t$ = 2.25 min. MS(ESIpos): m/z = 487.1 (M + H)$^+$. $^1$H-NMR(400 MHz, DMSO-d$_6$): δ =1.55(quintet, 1H), 1.85(q, 2H), 2.00(quintet, 1H), 3.39(s, 1H), 3.61(q, 2H), 3.76(q, 2H), 4.18(q, 3H), 5.90(s, 2H), 6.58(t, 1H), 7.00(t, 1H), 7.22(dt, 2H), 7.36(d, 3H), 7.43(s, 1H), 7.47(d, 1H), 7.85(d, 2H), 8.14(s, 1H), 9.92(s, 1H), 10.56(s, 1H). |

Example 37

N-[4-(Acetylamino)phenyl]-1-(2-fluorobenzyl)-5-{[(1-ethylcyclopentyl)acetyl]-amino}-1H-indole-2-carboxamide

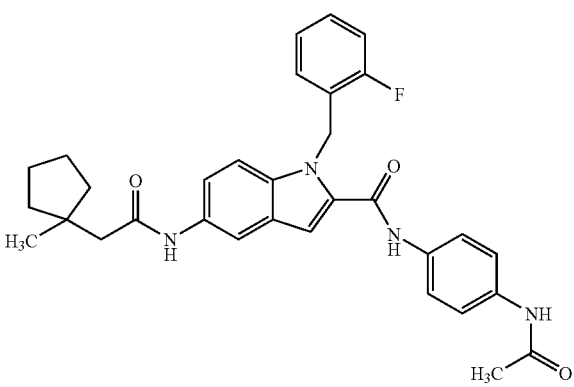

79 mg (0.15 mol) of the compound from Example 36 and 30 mg (0.29 mmol) of triethylamine are initially charged in 3 ml of dichloromethane, and the mixture is cooled to 0° C. 11.5 mg (0.15 mmol) of acetyl chloride are then added, and the mixture is stirred at RT overnight. The mixture is diluted with 10 ml of dichloromethane and washed successively with 1 N hydrochloric acid, aqueous sodium bicarbonate solution and water and dried over sodium sulphate, and the solvent is removed under reduced pressure. The residue is triturated with diisopropyl ether, isolated by filtration and dried.

Yield: 68 mg (63% of theory)

LC/MS (MHZ2P01): R$_t$=4.82 min.

MS (ESIpos): m/z=541.3 (M+H)$^+$.

$^1$H-NMR (200 MHz, DMSO-d$_6$): δ=1.07 (s, 3H), 1.63 (s, 8H), 2.02 (s, 3H), 2.29 (s, 2H), 5.90 (s, 2H), 6.57 (t, 1H), 7.00 (t, 1H), 7.13–7.72 (m, 7H), 8.09 (s, 1H), 9.77 (s, 1H), 9.91 (s, 1H), 10.31 (s, 1H)

The following compounds are prepared analogously to the procedure described in Example 37:

| Example | Structure | Analytical data |
|---|---|---|
| 38 | 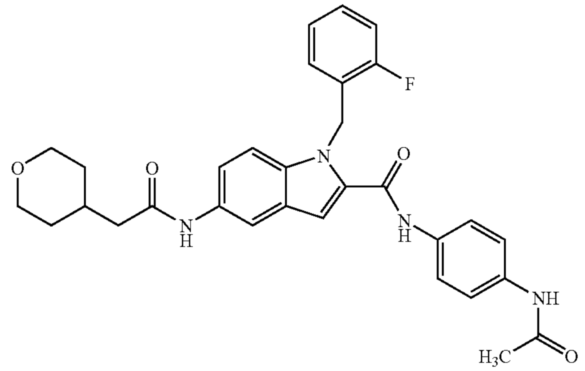 | LC/MS(MHZ2P01): R_t = 3.95 min. MS(ESIpos): m/z = 543.3 (M + H)+. $^1$H-NMR(200MHZ, DMSO-$d_6$): δ = 1.15(s, 1H), 2.03(d, 8H), 2.16(t, 1H), 2.43(s, 3H), 2.84(t, 2H), 5.89(s, 2H), 6.59(t, 1H), 7.01(t, 1H), 7.17–7.67(m, 9H), 8.07 (s, 1H), 9.90(d, 2H), 10.30 (s, 1H). |
| 39 | 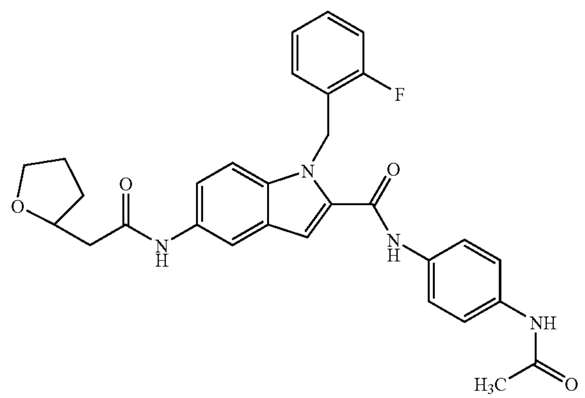 | LC/MS(MHZ2P01): R_t = 3.97 min. MS(ESIpos): m/z = 529.1 (M + H)+. |

Example 40

5-[(4,4-Dimethylpentanoyl)amino]-1-(2-fluorobenzyl)-N-phenyl-1H-indole-2-carboxamide

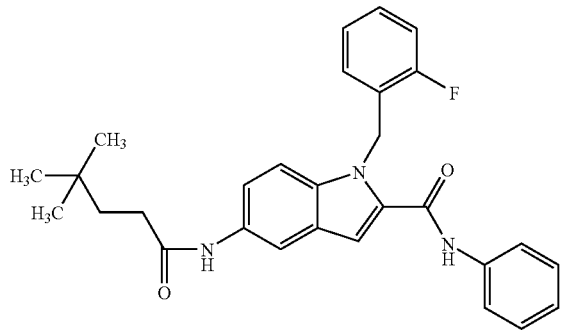

A solution of 300 mg (0.83 mmol) of the compound from Example XVI, 51 mg (0.42 mmol) of 4-dimethylaminopyridine and 240 mg (1.25 mmol) of N'-(3-dimethylaminopropyl)-N-ethylcarbodiimide×HCl in 10 ml of DMF is initially charged. 126 mg (1.0 mmol) of 4,4-dimethyl-2-pentinoic acid (prepared according to J. Chem. Soc. Perkin II 1990, 1997ff.) is added, and the mixture is stirred at RT overnight. For work-up, the mixture is diluted and extracted with dichloromethane and aqueous hydrochloric acid. The organic phase is washed with sat. sodium bicarbonate solution, dried with sodium sulphate, filtered and concentrated under reduced pressure, using a rotary evaporator. The residue is purified by preparative HPLC. 258 mg of a white solid (53% of theory) are obtained, 100 mg (0.21 mmol) of which are dissolved in 5 ml of ethanol and hydrogenated at atmospheric pressure in the presence of 50 mg of Pd/activated carbon (10%) for 3 h. The solution is then filtered through Celite, and the filter cake is washed thoroughly with ethyl acetate/ethanol. The solvent is removed under reduced pressure.

Yield: 101 mg (99% of theory)

$^1$H-NMR (200 MHz, DMSO-$d_6$): δ=0.91 (s, 9H), 1.53 (m, 2H), 2.29 (m, 2H), 5.90 (s, 2H), 6.59 (t, 1H), 7.06 (dt, 2H), 7.13–7.40 (m, 6H), 7.46 (d, 1H), 7.73 (d, 2H), 8.10 (s, 1H), 9.86 (s, 1H), 10.35 (s, 1H).

Example 41

N-{4-[(Dimethylamino)carbonyl]phenyl}-5-[(3,3-dimethylbutanoyl)amino]-1-(2-fluorobenzyl)-1H-indole-2-carboxamide

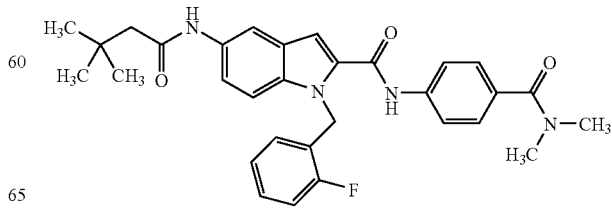

Under argon, 200 mg (0.43 mmol) of 5-[(3,3-dimethylbutanoyl)amino]-1-(2-fluorobenzyl)-1H-indole-2-carboxylic acid (Example XXXIX) are dissolved in 2 ml of DMF, and 4 ml of pyridine are added. 489.2 mg (1.29 mmol) of HATU are added to this solution, 140.8 mg (0.86 mmol) of 4-amino-N,N-dimethylbenzamide are then slowly added dropwise and the reaction mixture is stirred at RT overnight. For work-up, water is added and the mixture is extracted repeatedly with ethyl acetate. The combined organic phases are dried over sodium sulphate and filtered, and the solvent is removed under reduced pressure. The residue is purified by preparative HPLC. This gives 47.4 mg (15% of theory) of product.

HPLC (SYA-HPPSK2): $R_t$=4.69 min.

MS (ESIpos): m/z=529 (M+H)$^+$.

$^1$H-NMR (400 MHz, DMSO-d$_6$): δ=1.04 (s, 9H), 2.19 (s, 2H), 2.96 (s, 6H), 5.90 (s, 2H), 6.60 (t, 1H), 7.19 (t, 1H), 7.25 (q, 1H), 7.27–7.50 (m, 3H), 7.79 (d, 2H), 781 (s, 1H), 8.10 (s, 1H), 9.75 (s, 1H), 10.51 (d, 1H).

The following compounds are prepared analogously to the procedure described in Examples 26 and 41 using the appropriate starting materials:

| Example | Structure | Analytical data |
|---|---|---|
| 42 | 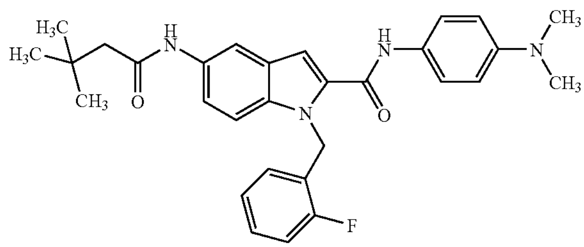 | LC/MS(MHZ2P01): $R_t$ = 4.68 min. MS(ESIpos): m/z = 501.4 (M + H)$^+$. $^1$H-NMR(300 MHz, DMSO-d$_6$): δ = 1.04(s, 9H), 2.19(s, 2H), 2.86(s, 6H), 5.90(s, 2H), 6.70(d, 2H), 7.00 (t, 1H), 7.20(dt, 2H), 7.30(s, 1H), 7.33(d, 1H), 7.41(d, 1H), 7.51(d, 2H), 8.05(d, 1H), 9.69(s, 1H), 10.06(s, 1H). |
| 43 | 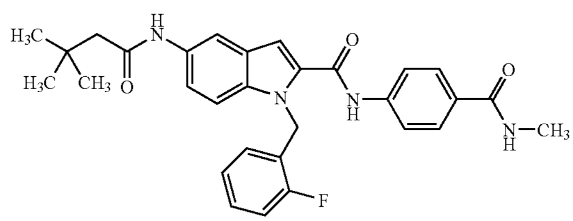 | LC/MS(SMKL-ZQ-2A-CC): $R_t$ = 3.22 min. MS(ESIpos): m/z = 515.2 (M + H)$^+$. |
| 44 | 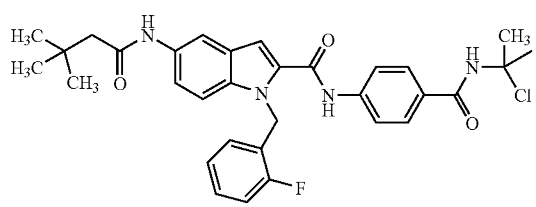 | HPLC(SYA-HPPSK2): $R_t$ = 5.09 min. $^1$H-NMR(300 MHz, CDCl$_3$): δ = 1.04(s, 9H), 1.38(s, 9H), 2.19(s, 2H), 5.90(s, 2H), 6.61(t, 1H), 7.00(t, 1H), 7.22(dt, 2H), 7.35(d, 1H), 7.42(d, 2H), 7.60(s, 1H), 7.79(s, 4H), 8.09(d, 1H), 9.72(s, 1H), 10.47(s, 1H). |
| 45 | 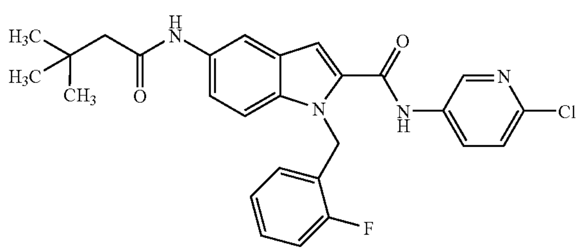 | HPLC(SYA-HPPSK2): $R_t$ = 5.07 min. MS(ESIpos): m/z = 493.2 (M + H)$^+$. $^1$H-NMR(300 MHz, DMSO-d$_6$): δ = 10.67(s, 1H), 9.76 (s, 1H), 8.74(d, 1H), 8.20 (dd, 1H), 8.12(d, 1H), 7.5–7.45(m, 2H), 7.43(s, 1H), 7.38(d, 1H), 7.33–7.14(m, 3H), 7.00(dt, 1H), 5.89(s, 2H), 2.19(s, 2H), 1.04(s, 9H). |
| 46 | 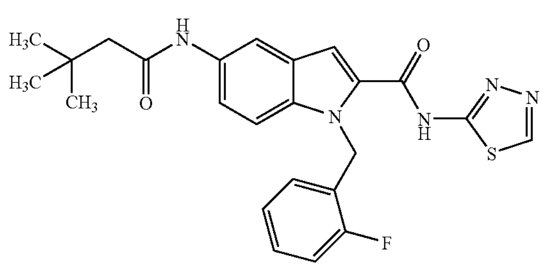 | HPLC(SYA-HPPSK2): $R_t$ = 4.67 min. MS(ESIpos): m/z = 466.1 (M + H)$^+$. $^1$H-NMR(300 MHz, DMSO-d$_6$): δ = 1.04(s, 9H), 2.20(s, 2H), 5.93(s, 2H), 6.55(t, 1H), 7.00(t, 1H), 7.23(dt, 2H), 7.35(dd, 1H), 7.49(d, 1H), 7.77(s, 1H), 8.16(d, 1H), 9.19(s, 1H), 9.75(s, 1H), 13.07(s, 1H). |

| Example | Structure | Analytical data |
|---|---|---|
| 47 | 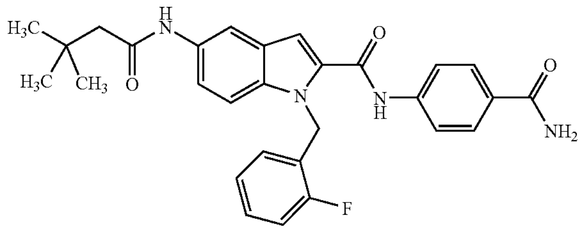 | HPLC(SYA-HPPSK2):<br>R$_t$ = 4.56 min.<br>MS(ESIpos): m/z = 501.0<br>(M + H)$^+$.<br>$^1$H-NMR(300 MHz, DMSO-d$_6$): δ = 1.04(s, 9H), 2.20(s, 2H), 5.90(s, 2H), 6.62(t, 1H), 7.01(t, 1H), 7.22(dt, 3H), 7.36(dd, 1H), 7.43(d, 2H), 7.83(q, 5H), 8.09(d, 1H), 9.73(s, 1H), 10.52(s, 1H). |
| 50 | 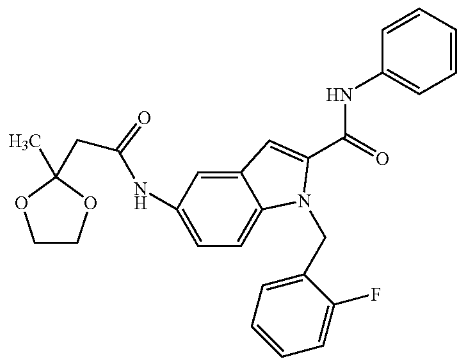 | LC/MS(SMKL-ZQ-2A):<br>R$_t$ = 3.43 min.<br>MS(ESIpos): m/z = 488.3<br>(M + H)$^+$.<br>$^1$H-NMR(200 MHz, DMSO-d$_6$): δ 1.45(s, 3H), 2.62(s, 2H), 3.92(d, 4H), 5.90(s, 2H), 6.60(t, 1H), 6.96–7.41 (m, 8H), 7.46(d, 1H), 7.73 (d, 2H), 8.10(d, 1H), 9.77(s, 1H), 10.37(s, 1H). |
| 51 | 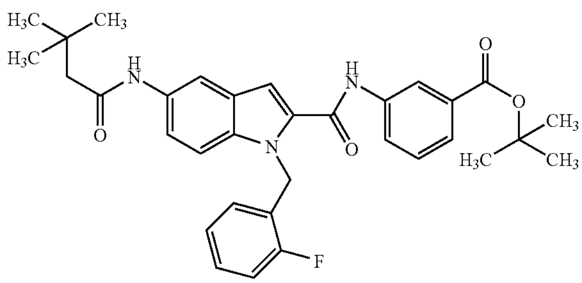 | LC/MS(method 2):<br>R$_t$ = 4.82 min.<br>MS(ESIpos): m/z = 558<br>(M + H)$^+$.<br>$^1$H-NMR(400 MHz, DMSO-d$_6$): δ = 1.05(s, 9H), 1.56(s, 9H), 2.19(s, 2H), 5.90(s, 2H), 6.60(t, 1H), 7.02(t, 1H), 7.22(m, 2H), 7.36(d, 1H), 7.44(m, 3H), 7.63(d, 1H), 8.00(d, 1H), 8.10(s, 1H), 8.28(s, 1H), 9.77(s, 1H), 10.54(s, 1H). |
| 52 | 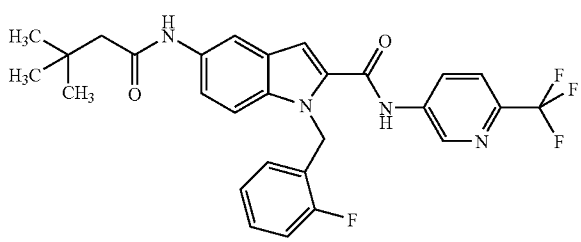 | HPLC(SYA-HPPSK2):<br>R$_t$ = 5.01 min.<br>MS(ESIpos): m/z = 526.9<br>(M + H)$^+$.<br>$^1$H-NMR(300 MHz, DMSO-d$_6$): δ = 1.04(s, 9H), 2.20(s, 2H), 5.90(s, 2H), 6.62(t, 1H), 7.01(t, 1H), 7.16–7.29 (m, 2H), 7.38(dd, 1H), 7.48 (t, 2H), 7.88(d, 1H), 8.12(d, 1H), 8.44(dd, 1H), 9.04(d, 1H), 9.74(s, 1H), 10.87(s, 1H). |
| 53 | 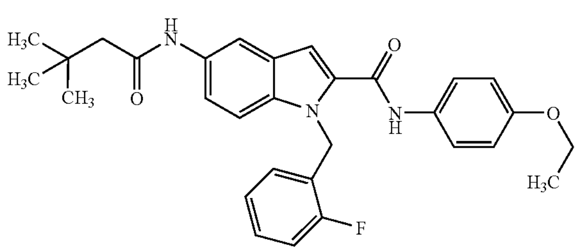 | HPLC(SYA-HPPSK2):<br>R$_t$ = 5.06 min.<br>MS(ESIpos): m/z = 502<br>(M + H)$^+$.<br>$^1$H-NMR(300 MHz, DMSO-d$_6$): δ = 1.04(s, 9H), 1.31(t, 3H), 2.19(s, 2H), 3.99(q, 2H), 5.89(s, 2H), 6.60(t, 1H), 6.88(d, 2H), 7.0(t, 1H), 7.14–7.28(m, 2H), 7.32(s, 1H), 7.34(d, 1H), 7.43(d, 1H), 7.60(d, 2H), 8.06(d, 1H), 9.70(s, 1H), 10.20(s, 1H). |

-continued

| Example | Structure | Analytical data |
|---|---|---|
| 54 | 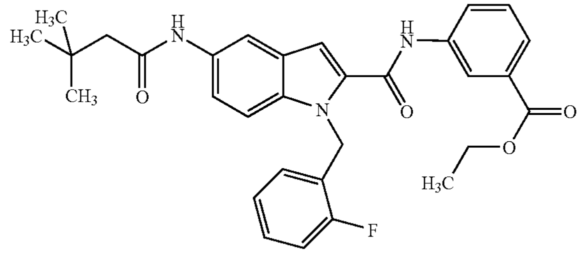 | HPLC(method 1):<br>$R_t$ = 5.376 min.<br>MS(ESIpos): m/z = 530 (M + H)⁺.<br>¹H-NMR(200 MHz, DMSO-$d_6$): δ = 1.04(s, 9H), 1.33(t, 3H), 2.19(s, 2H), 4.33(q, 2H), 5.92(s, 2H), 6.61(t, 1H), 7.0(t, 1H), 7.15–7.40 (m, 3H), 7.49(m, 3H), 7.68 (d, 1H), 8.04(d, 1H), 8.12 (d, 1H), 9.70(s, 1H), 10.58 (s, 1H). |
| 55 | 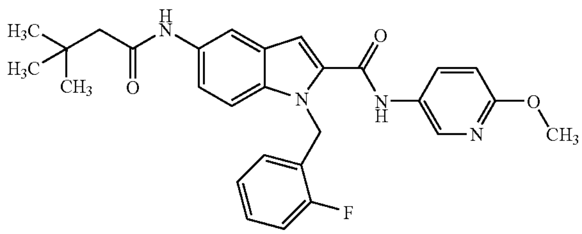 | HPLC(SYA-HPPSK2):<br>$R_t$ = 4.71 min.<br>MS(ESIpos): m/z = 488.9 (M + H)⁺.<br>¹H-NMR(300 MHz, DMSO-$d_6$): δ = 1.04(s, 9H), 2.19(s, 2H), 3.83(s, 3H), 5.89(s, 2H), 6.61(t, 1H), 6.82(s, 1H), 7.0(t, 1H), 7.15–7.32(m, 3H), 7.36(s, 1H), 7.44(d, 1H), 7.99(dd, 1H), 8.09(s, 1H), 8.45(d, 1H), 9.71(s, 1H), 10.37(s, 1H). |
| 56 | 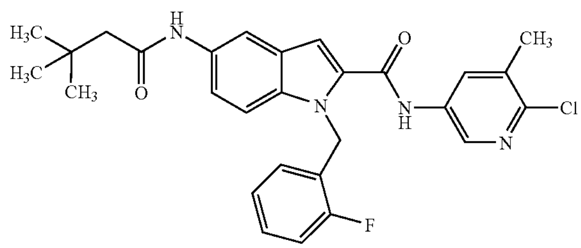 | HPLC(SYA-HPPSK2):<br>$R_t$ = 5.14 min.<br>MS(ESIpos): m/z = 507 (M + H)⁺.<br>¹H-NMR(300 MHz, DMSO-$d_6$): δ = 1.04(s, 9H), 2.14(s, 2H), 2.34(s, 3H), 5.89(s, 2H), 6.59(t, 1H), 7.0(t, 1H), 7.13–7.29(m, 2H), 7.35(dd, 1H), 7.42(s, 1H), 7.45(d, 1H), 8.10(d, 1H), 8.18(d, 1H), 8.56(d, 1H), 9.72(s, 1H), 10.59(s, 1H). |

Example 57

N-(4-Aminophenyl)-5-[(3,3-dimethylbutanoyl)amino]-1-(2-fluorobenzyl)-1H-indole-2-carboxamide hydrochloride

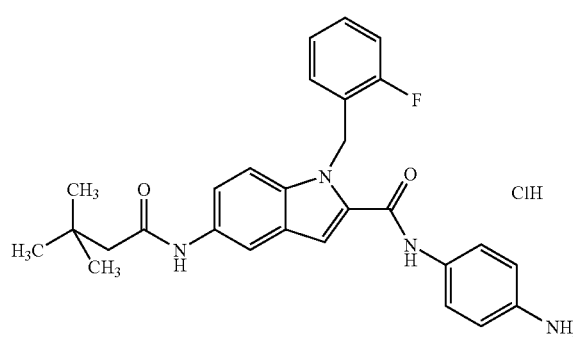

104 mg (0.18 mmol) of tert-butyl 4-({[5-[3,3-dimethylbutanoyl)amino]-1-(2-fluoro-benzyl)-1H-indol-2-yl]carbonyl}amino)phenylcarbamate (Example XLV) are taken up in 1 ml of dioxane and 1 ml of concentrated hydrochloric acid, and the mixture is stirred at RT for 1 h. The solvent is removed under reduced pressure and the crystals that remain are filtered off and dried. This gives 92.5 mg (75%) of the product.

LC/MS (SMKL-ZQ-2): $R_t$=3.09 min.
MS (ESIpos): m/z=473 (M+H)⁺
¹H-NMR (200 MHz, DMSO-$d_6$): δ=1.04 (s, 9H), 1.47 (s, 9H), 2.19 (s; 2H), 5.90 (s, 2H), 6.56 (t, 1H), 7.00 (dt, 1H), –7.16–7.49 (m, 7H), 7.59 (d, 2H), 8.08 (s, 1H), 931 (s, 1H), 9.75 (s, 1H), 10.26 (s, 1H).

Example 58

5-[(3,3-Dimethylbutyl)amino]-1-(2-fluorobenzyl)-N-{4-[(methylsulphonyl)amino]-phenyl}-1H-indole-2-carboxamide

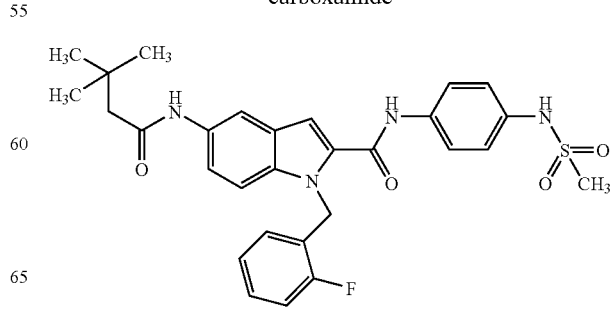

22.5 mg (0.20 mmol) of methanesulphonyl chloride are dissolved in 1 ml of dichloromethane, and 38.9 mg (0.49 mmol) of pyridine are added. A solution of 100 mg (0.20 mmol) of N-(4-aminophenyl)-5-[(3,3-dimethylbutyl)amino]-1-(2-fluorobenzyl)-1H-indole-2-carboxamide hydrochloride (Example 57) in 1 ml of dichloromethane is added dropwise to this mixture, and the reaction mixture is stirred at RT overnight. For work-up, 22 ml of 1-molar hydrochloric acid are added, and the mixture is extracted repeatedly with dichloromethane. The combined organic phases are washed in each case once with saturated copper sulphate solution, saturated sodium bicarbonate solution and water. They are then dried over sodium sulphate and filtered, and the solvent is removed under reduced pressure. This gives 96.2 mg (73%) of the product.

LC/MS (MHZ2P01): $R_t$=4.81 min.

MS (ESIpos): m/z=551 (M+H)$^+$.

$^1$H-NMR (400 MHz, DMSO-d$_6$): δ=1.04 (s, 9H), 2.19 (s, 2H), 2.94 (s, 3H), 5.89 (s, 2H), 6.58 (t, 1H), 7.00 (t, 1H), 7.14–7.29 (m, 4H), 7.34 (d, 2H), 7.45 (d, 1H), 768 (d, 2H), 8.09 (s, 1H), 9.58 (s, 1H), 9.73 (s, 1H), 10.35 (s, 1H).

The following compound is prepared analogously to the procedure described in Example 58:

| Example | Structure | Analytical data |
|---|---|---|
| 59 | 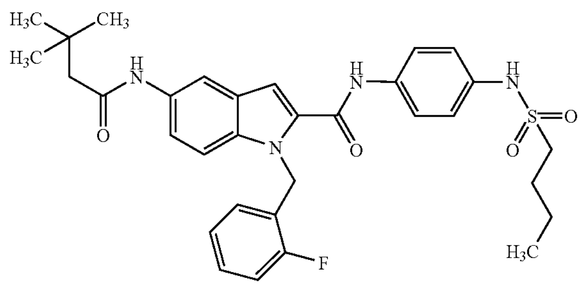 | LC/MS(MHZ2Q01): $R_t$ = 4.91 min. MS(ESIpos): m/z = 593 (M + H)$^+$. $^1$H-NMR(400 MHz, DMSO-d$_6$): δ = 0.83(t, 3H), 1.04(s, 9H), 1.33(m, 2H), 1.62(m, 2H), 2.19(s, 2H), 2.95(m, 2H), 5.89(s, 2H), 6.58(t, 1H), 7.00(t, 1H), 7.03–7.37(m, 5H), 7.43(d, 2H), 7.59(m, 2H), 8.08(s, 1H), 9.72(s, 1H), 10.26(s, 1H). |

The following compound is prepared analogously to the procedure described in Example 37 using Example 57 as starting material:

| Example | Structure | Analytical data |
|---|---|---|
| 60 | 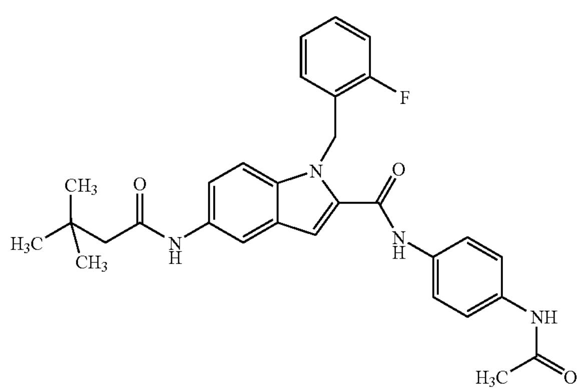 | LC/MS(MHZ2Q01): $R_t$ = 4.45 min. MS(ESIpos): m/z = 515 (M + H)$^+$. $^1$H-NMR(200 MHz, DMSO-d$_6$): δ = 1.04(s, 9H), 2.02(s, 3H), 2.19(s, 2H), 6.00(s, 2H), 6.58(dt, 1H), 7.00(dt, 1H), 2H), 7.64(d, 2H), 8.09(s, 1H), 9.75(s, 1H), 9.91(s, 1H), 10.31(s, 1H). |

Example 61

N-[4-(Butyrylamino)phenyl]-5-[(3,3-dimethylbutyl)amino]-1-(2-fluorobenzyl)-1H-indole-2-carboxamide

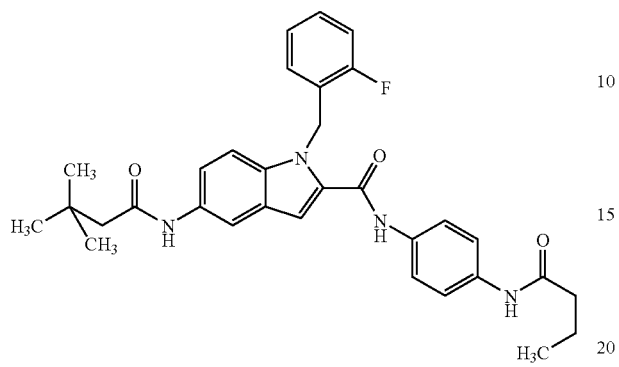

84 mg (0.14 mmol) of ethyl-2-({[4-({[5-(3,3-dimethylbutanoyl)amino[-1-(2-fluoro-benzyl]1H-indol-2-yl]carbonyl}amino)phenyl]amino}carbonyl)butanoate (Example XLVI) and 6.5 mg (0.27 mmol) of lithium hydroxide are taken up in 0.5 ml of methanol and 0.5 ml of THF, and the mixture is heated at 90° C. for 30 min. For work-up, the cold reaction mixture is diluted with ethyl acetate and extracted in each case once with 1-molar hydrochloric acid and saturated sodium chloride solution. The organic phase is dried over sodium sulphate and filtered, and the solvent is removed under reduced pressure. The residue is triturated with diethyl ether/dichloromethane and the resulting solid is filtered off. The crude product is purified by preparative HPLC. This gives 4.9 mg (7% of theory) of the product.

LC/MS (SMKL-ZQ-2A-CC): $R_t$=3.54 min.
MS (ESIpos): m/z=543.2 (M+H)$^+$.

Example 62

N-(6-Amino-3-pyridinyl)-5-[(3,3-dimethylbutanoyl)amino]-1-(2-fluorobenzyl)-1H-indole-2-carboxamide

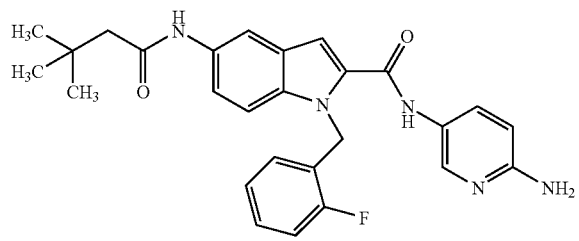

107 mg (0.12 mmol) of di-(tert-butyl) 5-({[5-[(3,3-dimethylbutanoyl)amino]-1-(2-fluorobenzyl)-1H-indol-2-yl]carbonyl}amino)-2-pyridinylimidedicarbonate (Example XLII) are suspended in 2 ml of dichloromethane/trifluoroacetic acid (1:1), and the mixture is stirred at RT overnight. The solvent is removed under reduced pressure, the residue is taken up in water and the pH is adjusted to 7–8 using 1-molar sodium hydroxide solution. The mixture is extracted repeatedly with ethyl acetate, the combined organic phases are dried over sodium sulphate and filtered and the solvent is removed under reduced pressure. The crude product is purified by preparative HPLC. This gives 48 mg (83%) of the product.

HPLC (SYA-HPPSK2): $R_t$=4.47 min.
MS (ESIpos): m/z=474.0 (M+H)$^+$.
$^1$H-NMR (200 MHz, DMSO-d$_6$): δ=1.04 (s, 9H), 2.19 (s, 2H), 5.81 (s, 2H), 5.89 (d, 2H), 6.43 (d, 1H), 6.56 (t, 1H), 7.00 (t, 1H), 7.12–7.48 (m, 5H), 7.65 (d, 1H), 8.12 (d, 2H), 9.74 (s, 1H), 10.10 (s, 1H).

Example 63

N-(5-Amino-2-pyridinyl)-5-[(3,3-dimethylbutanoyl)amino]-1-(2-fluorobenzyl)-1H-indole-2-carboxamide

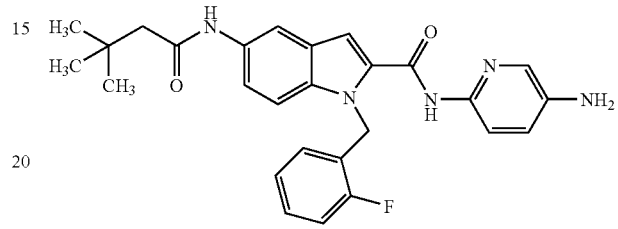

46.8 mg (0.19 mmol) of hydrogen bromide (33% strength solution in acetic acid) are added to 29 mg (0.05 mmol) of benzyl 6-({[5-[(3,3-dimethylbutanoyl)amino]-1-(2-fluorobenzyl)-1H-indol-2-yl]carbonyl}amino)-3-pyridinylcarbamate (Example XLI), and the mixture is stirred at RT overnight. The solvent is removed under reduced pressure and the residue is purified by preparative HPLC. This gives 6 mg (27%) of the product.

LC/MS (MHZ2P01): $R_t$=3.98 min.
MS (ESIpos): m/z=474.3 (M+H)$^+$.
$^1$H-NMR (300 MHz, DMSO-d$_6$): δ=1.04 (s, 9H), 2.19 (s, 2H), 5.14 (s, 2H), 5.91 (s, 2H), 6.52 (t, 1H), 6.99 (t, 1H), 7.14–7.29 (m, 3H), 7.30 (d, 1H), 7.49 (s, 7.69 (d, 1H), 7.73 (d, 1H), 8.08 (d, 1H), 9.69 (s, 1H), 10.32 (s, 1H).

Example 64

3-({[5-[(3,3-dimethylbutanoyl)amino]-1-(2-fluorobenzyl)-1H-indol-2-yl]carbonyl}-amino)benzoic acid

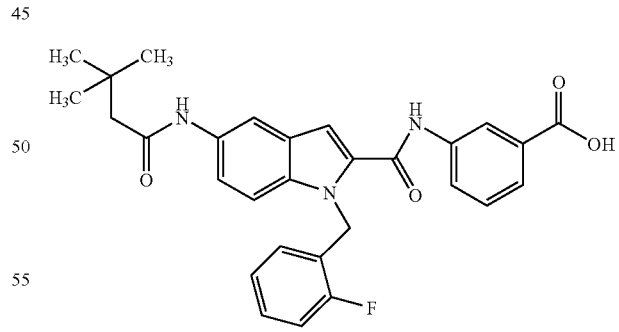

0.3 ml of trifluoroacetic acid is added to a solution of 182 mg (0.32 mmol) of the compound from Example 51 in 1 ml of dichloromethane. The mixture is stirred at RT for 1 h and concentrated under reduced pressure.

Yield: 163 mg (100% of theory).
LC/MS (MHZ2P01): $R_t$=4.60 min.
MS (ESIpos): m/z=502 (M+H)$^+$.
$^1$H-NMR (300 MHz, DMSO-d$_6$): δ=1.04 (s, 9H), 2.19 (s, 2H), 5.90 (s, 2H), 6.62 (t, 1H), 6.99 (t, 1H), 7.14–7.30 (m, 2H), 7.34 (dd, 1H), 7.44 (m, 3H), 7.65 (d, 1H), 797 (d, 1H), 8.09 (d, 1H), 8.38 (s, 1H), 9.71 (s, 1H), 10.48 (s, 1H).

Example 65

N-{3-[(tert-Butylamino)carbonyl]phenyl}-5-[(3,3-dimethylbutanoyl)amino]-1-(2-fluorobenzyl)-1H-indole-2-carboxamide

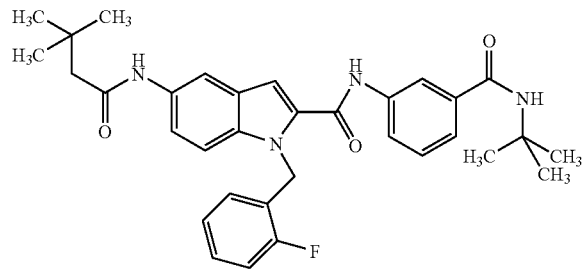

20 mg (0.04 mmol) of the compound from Example 64, 11.5 mg (0.06 mmol) of N'-(3-dimethylaminopropyl)-N-ethylcarbodiimide×HCl and 2.5 mg (0.02 mmol) of 4-dimethylaminopyridine are initially charged in 1 ml of dichloromethane. 3.5 mg

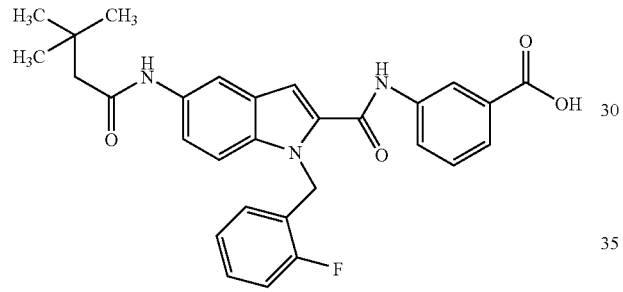

0.3 ml of trifluoroacetic acid is added to a solution of 182 mg (0.32 mmol) of the compound from Example 51 in 1 ml of dichloromethane. The mixture is stirred at RT for 1 h and concentrated under reduced pressure.
Yield: 163 mg (100% of theory).
LC/MS (MHZ2P01): $R_t$=4.60 min.
MS (ESIpos): m/z=502 (M+H)$^+$.
$^1$H-NMR (300 MHz, DMSO-d$_6$): δ=1.04 (s, 9H), 2.19 (s, 2H), 5.90 (s, 2H), 6.62 (t, 1H), 6.99 (t, 1H), 7.14–7.30 (m, 2H), 7.34 (dd, 1H), 7.44 (m, 3H), 7.65 (d, 1H), 7.97 (d, 1H), 8.09 (d, 1H), 8.38 (s, 1H), 9.71 (s, 1H), 10.48 (s, 1H).

Example 65

N-{3-[(tert-Butylamino)carbonyl]phenyl}-5-[(3,3-dimethylbutanoyl)amino]-1-(2-fluorobenzyl)-1H-indole-2-carboxamide

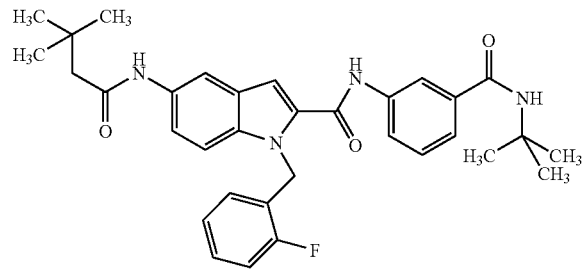

20 mg (0.04 mmol) of the compound from Example 64, 11.5 mg (0.06 mmol) of N'-(3-dimethylaminopropyl)-N-ethylcarbodiimide×HCl and 2.5 mg (0.02 mmol) of 4-dimethylaminopyridine are initially charged in 1 ml of dichloromethane. 3.5 mg (0.05 mmol) of tert-butylamine are added, and the mixture is stirred at RT overnight. For work-up, the mixture is diluted and extracted with aqueous hydrochloric acid and dichloromethane. The organic phase is washed with sat. sodium chloride solution, dried with sodium sulphate, filtered and dried under reduced pressure. Purification is carried out by chromatography on silica gel.

Yield: 10 mg (45% of theory)
LC/MS (method 2): $R_t$=3.82 min.
MS (ESIpos): m/z=557 (M+H)$^+$.
$^1$H-NMR (300 MHz, DMSO-d$_6$): δ=1.04 (s, 9H), 1.41 (s, 9H), 2.20 (s, 2H), 5.91 (s, 2H), 6.60 (t, 1H), 6.99 (t, 1H), 7.25 (m, 2H), 7.40 (m, 4H), 7.62 (s, 1H), 8.09 (d, 2H), 9.71 (s, 1H), 10.41 (s, 1H).

Example 66

4-({[5-[(3,3-Dimethylbutanoyl)amino]-1-(2-fluorobenzyl)-1H-indol-2-yl]carbonyl}-amino)benzoic acid

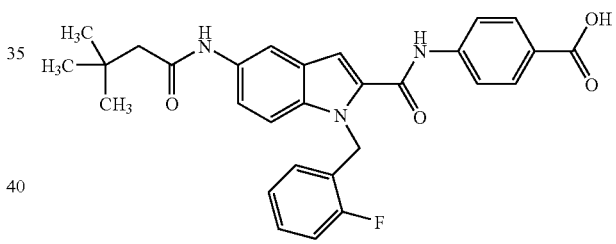

912.6 mg (2.4 mmol) of HATU and 1.24 g (6.4 mmol) of tert-butyl 4-aminobenzoate are added to a suspension of 1.0 g (0.8 mmol) of the substance from Example XLI in 21 ml of pyridine/DMF (2:1), and the reaction mixture is shaken at RT overnight. The resin is filtered off with suction and washed with DMF, ethanol (30%), water, DMF, methanol and dichloromethane. To remove the polymer, the bound product is suspended in dichloromethane/trifluoroacetic acid (1:1) and shaken at RT for 30 min. The free polymer is filtered off with suction and washed with dichloromethane, and the filtrate is freed from the solvent under reduced pressure. The residue is purified chromatographically on silica gel (mobile phase: dichloromethane/methanol 5:1). This gives 127 mg (32% of theory) of the product.

LC/MS (MHZ2P): $R_t$=4.39 min.
MS (ESIpos): m/z=502.3 (M+H)$^+$.

The following compound is prepared analogously to the procedure described in Example 66:

| Example | Structure | Analytical data |
|---|---|---|
| 67 | 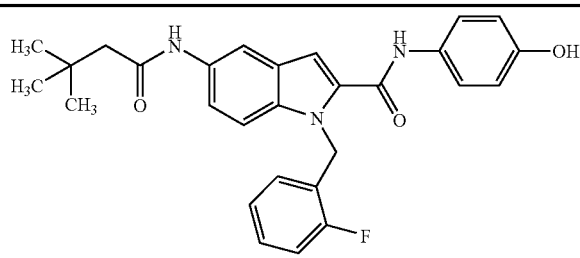 | LC/MS(MHZ2P01): R$_t$ = 4.86 min. MS(ESIpos): m/z = 474.3 (M + H)$^+$. $^1$H-NMR(300MHz, DMSO-d$_6$): δ = 1.04(s, 9H), 2.19(s, 2H), 5.89(s, 2H), 6.59(t, 1H), 6.71(d, 2H), 7.00(t, 1H), 7.18–7.38(m, 4H), 7.40(s, 1H), 7.47(d, 2H), 7.95(s, 1H), 8.07(d, 1H), 9.22(br s, 1H), 6.70(s, 1H), 10.11(s, 1H). |

Example 68

5-[(Bicyclo[2.2.1]hept-2-ylacetyl)amino]-N-phenyl-1-(2-phenylethyl)-1H-indole-2-carboxamide

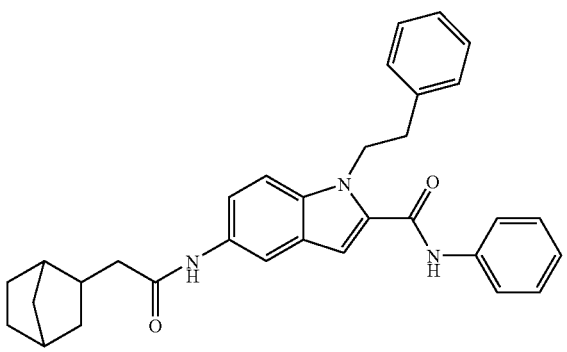

Under argon, 78 mg (0.22 mmol) of 5-amino-N-phenyl-1-(2-phenylethyl)-1H-indole-2-carboxamide (Example LI) are dissolved in 2 ml of THF, and 24.4 mg (0.24 mmol) of triethylamine are added. The solution is cooled to 0° C., and a solution of 37.9 mg (0.22 mmol) of bicyclo[2.2.1]hept-2-ylacetyl chloride in 0.2 ml of THF is added dropwise. The reaction mixture is stirred at RT for 2 h and then diluted with 1-molar hydrochloric acid and extracted repeatedly with ethyl acetate. The combined organic phases are washed twice with saturated sodium chloride solution and once with sodium bicarbonate solution, dried over sodium sulphate and filtered. The residue obtained after removal of the solvent under reduced pressure is purified chromatographically on silica gel (mobile phase: dichloromethane/ethyl acetate). 31.5 mg (29% of theory) of the product are obtained.

LC/MS (MHZ2P): R$_t$=5.17 min.

MS (ESIpos): m/z=492 (M+H)$^+$.

The following compound is prepared analogously to the procedure described in Example 68, using the starting material from Example LI:

| Example | Structure | Analytical data |
|---|---|---|
| 69 | 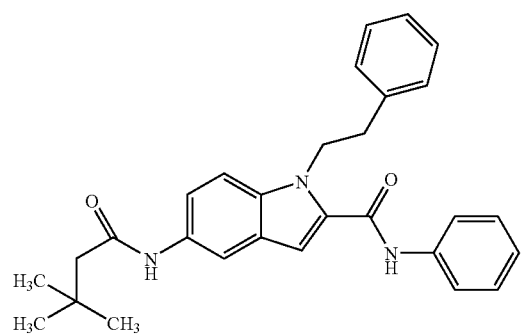 | LC/MS(MHZ2P): R$_t$ = 4.95 min MS(ESIpos): m/z = 454.5(M + H)$^+$ |

Example 70

5-[(3,3-Dimethylbutanoyl)amino]-1-(2-hydroxy-ethyl)-N-phenyl-1H-indole-2-carboxamide

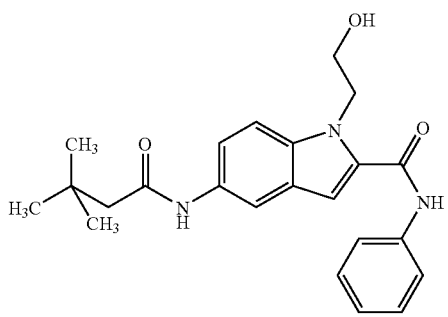

50 mg (0.12 mmol) of the compound from Example LV are dissolved in 5 ml of methanol. A total of 77.4 mg (2.05 mmol) of sodium borohydride are added a little at a time, over a period of several hours, at RT. The reaction mixture is stirred overnight at this temperature and then diluted with 1-molar hydrochloric acid and extracted repeatedly with ethyl acetate. The combined organic phases are dried over sodium sulphate and filtered and the solvent is removed under reduced pressure. This gives 38 mg (84% of theory) of the product.

LC/MS (MHZ2P01): $R_t$=4.14 min.

MS (ESIpos): m/z=394.3 (M+H)$^+$.

$^1$H-NMR (200 MHz, DMSO-d$_6$): δ=1.04 (s, 9H), 2.19 (s, 2H), 3.69 (q, 2H), 4.57 (t, 2H), 4.88 (t, 1H), 7.10 (t, 1H), 7.22 (s, 1H), 7.25–7.63 (m, 4H), 7.77 (d, 2h), 8.06 (d, 1H), 9.72 (s, 1H), 10.32 (s, 1H).

Example 71

5-[(3,3-Dimethylbutanoyl)amino]-N,1-diphenyl-1H-indole-2-carboxamide

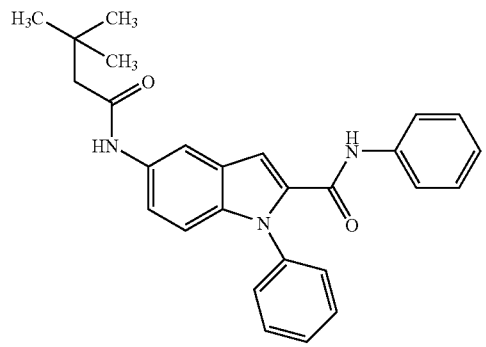

7.9 mg (0.09 mmol) of aniline are added to a solution of 27 mg (0.08 mmol) of 5-[(3,3-dimethylbutanoyl)amino]-1-phenyl-1H-indole-2-carboxylic acid (Example LIX), 4.7 mg (0.09 mmol) of DMAP and 22.2 mg (0.12 mmol) of EDC in 2 ml of dichloromethane, and the mixture is stirred at RT for 3 h. For work-up, 1-molar hydrochloric acid is added and the mixture is extracted repeatedly with dichloromethane. The combined organic phases are washed with saturated sodium bicarbonate solution and water, dried over sodium sulphate and filtered. Removal of the solvent under reduced pressure gives 35 mg (99% of theory) of the product.

LC/MS (MHZ2Q01): $R_t$=4.85 min.

MS (ESIpos): m/z=426.4 (M+H)$^+$.

$^1$H-NMR (200 MHz, DMSO-d$_6$): δ=1.04 (s, 9H), 2.20 (s, 2H), 7.05–7.15 (m, 2H), 7.29–7.41 (m, 6H), 7.44–7.60 (m, 3H), 7.65 (d, 2H), 8.15 (d, 1H), 9.79 (s, 1H), 1043 (s, 1H).

The following compound is prepared analogously to the procedure described in Preparation Example 57:

| Example | Structure | Analytical data |
|---|---|---|
| 72 | ![structure] | LC/MS(MHZ2Q01):$R_t$ = 3.78 min. MS(ESIpos): m/z = 441.4 (M + H)$^+$. $^1$H-NMR(200 MHz, DMSO-d$_6$): δ = 1.04(s, 9H), 2.20(s, 2H), 7.09 (d, 1H), 7.22(d, 3H), 7.29–7.56 (m, 8H), 7.73(d, 2H), 8.17(s, 1H), 9.81(s, 1H), 10.57(s, 1H). |

The following compounds are prepared analogously to the procedure described in Examples 26 and 41, using the appropriate starting materials:

| Example | Structure | Analytical data |
|---|---|---|
| 73 | (structure) | LC/MS(MHZ2P01):<br>R_t = 5.19 min.<br>MS(ESIpos): m/z = 508(M + H)+.<br>$^1$H-NMR(200 MHz, DMSO-d$_6$):<br>δ = 1.04(s, 9H), 2.19(s, 2H), 6.04 (s, 2H), 6.21(m, 1H), 7.07(t, 1H), 7.17–7.56(m, 8H), 7.69(d, 2H), 7.79(m, 1H), 8.17(s, 1H), 9.78(s, 1H), 10.38(s, 1H). |
| 74 | (structure) | LC/MS(MHZ2P01):<br>R_t = 5.47 min.<br>MS(ESIpos): m/z = 446.4 (M + H)+.<br>$^1$H-NMR(200 MHz, DMSO-d$_6$):<br>δ = 0.98–1.13(m, 13H), 1.32–1.49 (m, 2H), 1.50–1.69(m, 3H), 2.19 (s, 2H), 4.43(d, 2H), 7.10(t, 1H), 7.21(s, 1H), 7.31–7.42(m, 3H), 7.52(d, 1H), 7.76(d, 2H), 8.02(d, 1H), 9.72(s, 1H), 10.32(s, 1H). |
| 75 | (structure) | LC/MS(SMXL-ZQ-2A):<br>R_t = 3.53 min.<br>MS(ESIpos): m/z = 461.1 (M + H)+.<br>$^1$H-NMR(400 MHz, DMSO-d$_6$):<br>δ = 1.04(s, 9H), 2.19(s, 2H), 2.54 (s, 3H), 5.76(s, 1H), 6.96(s, 1H), 7.10(t, 1H), 7.28(s, 1H), 7.35(t, 4H), 7.57(d, 1H), 7.76(d, 2H), 8.03(s, 1H), 9.72(s, 1H), 10.36(s, 1H). |

The following compounds are prepared analogously to the procedure described in Example XXXV:

| Example | Structure | Analytical data |
|---|---|---|
| 76 | (structure) | LC/MS(MHZ2P01):<br>R_t = 5.19 min.<br>MS(ESIpos): m/z = 508(M + H)+.<br>$^1$H-NMR(200 MHz, DMSO-d$_6$):<br>δ = 1.04(s, 9H), 2.20(s, 2H), 6.03 (s, 2H), 6.13–6.28(m, 1H), 7.11(d, 2H), 7.19–7.47(m, 4H), 7.50(s, 1H), 7.69(d, 2H), 7.75–7.85(m, 1H), 8.18(s, 1H), 9.79(s, 1H), 10.43(s, 1H). |

| Example | Structure | Analytical data |
|---|---|---|
| 77 | 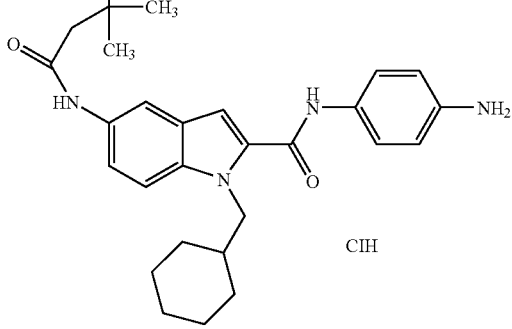 | LC/MS(MHZ2P01):<br>R$_t$ = 4.40 min.<br>MS(ESIpos): m/z = 461.4<br>(M + H)$^+$.<br>$^1$H-NMR(200 MHz, DMSO-d$_6$):<br>δ = 1.04(s, 14H), 1.42(br d, 2H),<br>1.51–1.73(m, 4H), 3.88(brs, 2H),<br>4.45(d, 2H), 7.25(s, 1H), 7.35(d,<br>4H), 7.53(d, 1H), 7.87(d, 2H),<br>8.05(s, 1H), 9.76(s, 1H), 10.50(s,<br>1H). |
| 78 | 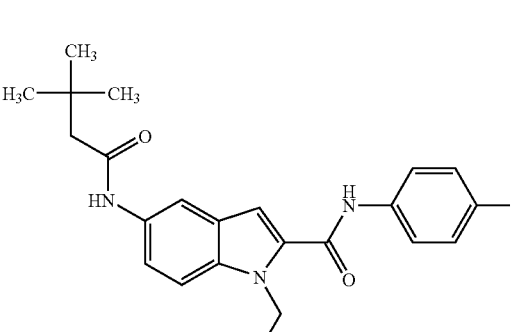 | LC/MS(SMKL-ZQ-2A):<br>R$_t$ = 3.09 min.<br>MS(ESIpos): m/z = 495.1<br>(M + H)$^+$.<br>$^1$H-NMR(400 MHz, DMSO-d$_6$):<br>δ = 1.04(s, 9H), 2.19(s, 2H), 4.97<br>(s, 2H), 5.89(s, 2H), 6.56(d, 2H),<br>6.90(d, 1H), 7.03(d, 1H), 7.24(s,<br>1H), 7.37(t, 3H), 7.65(d, 1H),<br>8.02(s, 1H), 9.72(s, 1H), 10.00(s,<br>1H). |

The following compound is prepared analogously to the procedure described in Example 37:

| Example | Structure | Analytical structure |
|---|---|---|
| 79 | 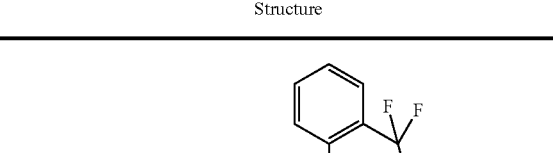 | LC/MS(SMKL-ZQ-2A):<br>R$_t$ = 3.60 min.<br>MS(ESIpos): m/z = 565(M + H)$^+$.<br>$^1$H-NMR(200 MHz, DMSO-d$_6$):<br>δ = 1.04(s, 9H), 2.01(s, 3H), 2.19<br>(s, 2H), 6.03(s, 2H), 6.19(d, 1H),<br>7.27(q, 4H), 7.39–7.63(m, 5H),<br>7.78(t, 1H), 8.16(s, 1H), 9.77(s,<br>1H), 9.90(s, 1H), 10.31(s, 1H). |

What the invention claimed is:

1. A compound of the formula (I)

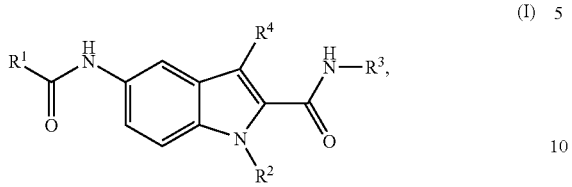

in which
R$^1$ represents (C$_5$–C$_{15}$)-alkyl, (C$_5$–C$_{15}$)-alkenyl or (CH$_2$)$_n$G,
in which
G represents cycloalkyl or represents a 5- or 6-membered heterocycle having one or two oxygen atoms,
n represents 0 to 4 and
alkyl, alkenyl and G are optionally substituted by 1 to 3 substituents, independently of one another selected from the group consisting of halogen, hydroxyl, trifluoromethyl, trifluoromethyl, cyano, nitro, alkyl, alkoxy, alkylthio, carboxyl, alkoxycarbonyl, amino, alkylamino, alkylcarbonylamino and alkylaminocarbonyl,
R$^2$ represents (C$_1$–C$_8$)-alkyl, (CH$_2$)$_m$cycloalkyl, (CH$_2$)$_m$heterocyclyl, (CH$_2$)$_m$aryl or (CH$_2$)$_m$heteroaryl,
in which
m represents 0 to 4 and
alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethyl, cyano, nitro, alkyl, alkoxy, alkylthio, alkoxycarbonyl, amino, alkylamino, alkylcarbonylamino, alkylaminocarbonyl, alkylaminosulphonyl and alkylsulphonylamino,
R$^3$ represents (CH$_2$)$_o$cycloalkyl, (CH$_2$)$_o$heterocyclyl, (CH$_2$)$_o$aryl or (CH$_2$)$_o$heteroaryl,
in which
o represents 0 to 4 and
cycloalkyl, heterocyclyl, aryl and heteroaryl are optionally substituted by 1 to 3 substituents, independently of one another selected from the group consisting of halogen, hydroxyl, trifluoromethyl, trifluoromethyl, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino,
R$^4$ represents hydrogen, (C$_1$–C$_4$)-alkyl, (CH$_2$)$_p$cycloalkyl, (CH$_2$)$_p$heterocyclyl, (CH$_2$)$_p$aryl or (CH$_2$)$_p$heteroaryl,
in which
p represents 0 to 4 and
alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethyl, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino,
or a salt, hydrate, hydrate of a salt or solvate thereof.

2. A compound of the formula (I) according to claim 1 in which
R$^1$ represents (C$_5$–C$_{15}$)-alkyl or (CH$_2$)$_n$cycloalkyl,
in which
n represents 0 to 4 and
alkyl and cycloalkyl are optionally substituted by 1 to 3 substituents, independently of one another selected from the group consisting of halogen, hydroxyl, trifluoromethyl, trifluoromethyl, cyano, nitro, alkyl, alkoxy, alkylthio, carboxyl, alkoxycarbonyl, alkylcarbonylamino and alkylaminocarbonyl,
R$^2$ represents (C$_1$–C$_8$)-alkyl, (CH$_2$)$_m$cycloalkyl, (CH$_2$)$_m$heterocyclyl, (CH$_2$)$_m$aryl or (CH$_2$)$_m$heteroaryl,
in which
m represents 0 to 4 and
alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethyl, cyano, nitro, alkyl, alkoxy, alkylthio, alkoxycarbonyl, amino, alkylamino, alkylcarbonylamino, alkylaminocarbonyl, alkylaminosulphonyl and alkylsulphonylamino,
R$^3$ represents (CH$_2$)$_o$cycloalkyl, (CH$_2$)$_o$heterocyclyl, (CH$_2$)$_o$aryl or (CH$_2$)$_o$heteroaryl,
in which
o represents 0 to 4 and
cycloalkyl, heterocyclyl, aryl and heteroaryl are optionally substituted by 1 to 3 substituents, independently of one another selected from the group consisting of halogen, hydroxyl, trifluoromethyl, trifluoromethyl, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino,
R$^4$ represents hydrogen, (C$_1$–C$_4$)-alkyl, (CH$_2$)$_p$cycloalkyl, (CH$_2$)$_p$heterocyclyl, (CH$_2$)$_p$aryl or (CH$_2$)$_p$heteroaryl,
in which
p represents 0 to 4 and
alkyl, cycloalkyl, heterocyclyl, aryl and heteroaryl are optionally substituted by 1 to 3 substituents, independently of one another selected from the group consisting of halogen, hydroxyl, trifluoromethyl, trifluoromethyl, cyano, nitro, alkyl, alkoxy, alkylthio, hydroxycarbonyl, alkoxycarbonyl, amino, alkylamino, alkylcarbonylamino, alkylaminocarbonyl, alkylaminosulphonyl and alkylsulphonylamino,
or a salt, hydrate, hydrate of a salt or solvate thereof.

3. A compound of the formula (I) according to claim 1, in which
R$^1$ represents neopentyl, (bicyclo[2.2.1]heptyl)methyl, cyclohexylmethyl, cyclobutylmethyl, cyclopentylmethyl, 2,2-dimethyl-1-butyl, 2-ethyl-2-methyl-1-butyl, (1-methylcyclopentyl)methyl), 1-methylcyclohexyl, 4-hydroxy-2,2-dimethyl-1-butyl or 2,2-dimethyl-1-but-3-enyl,
R$^2$ represents (C$_1$–C$_4$)-alkyl which may be substituted by hydroxyl or fluorine or represents benzyl which is optionally substituted by 1 or 2 substituents, independently of one another selected from the group consisting of fluorine, chlorine, bromine, methyl and trifluoromethyl, $R^3$ represents phenyl, pyridyl or pyrimidyl which for their part are optionally substituted by a substituent selected from the group consisting of fluorine, chlorine, trifluoromethyl, methyl, ethyl, methoxy, ethoxy, n-propoxy, isopropoxy, amino, hydroxyl, hydroxycarbonyl, ($C_1$–$C_3$)-alkylcarbonylamino and mono-($C_1$–$C_4$)-alkylaminocarbonyl, $R^4$ represents hydrogen or a salt, hydrate, hydrate of a salt or solvate thereof.

4. A process for preparing compounds of the formula (I) as defined in claim 1, characterized in that either (A) a compounds of the formula (II)

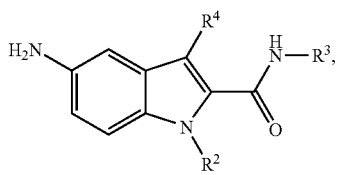

(II)

in which $R^2$, $R^3$ and $R^4$ are as defined in claim 1, is reacted with a compound of the formula (III)

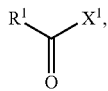

(III)

in which $R^1$ is as defined in claim 1 and $X^1$ represents halogen or hydroxyl, or (B) a compounds of the formula (XI)

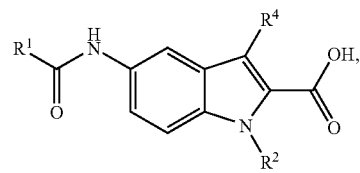

(XI)

in which $R^1$, $R^2$ and $R^4$ are as defined in claim 1, is reacted with a compound of the formula (VI)

$$R^3\text{---}NH_2 \quad (VI)$$

in which $R^3$ is as defined in claim 1.

5. A pharmaceutical composition, comprising at least one compound of the formula (I) as defined in claim 1 and at least one further auxiliary.

6. A pharmaceutical composition, comprising at least one compound of the formula (I) as defined in claim 1 and at least one further active compound.

7. A method for treating myocardial infarction, angina pectoris or cardiac insufficiency, comprising administering to a patient in need thereof an effective amount of a compound of the formula (I) as defined in claim 1.

* * * * *